(12) United States Patent
Brolén et al.

(10) Patent No.: US 9,394,522 B2
(45) Date of Patent: Jul. 19, 2016

(54) DIRECTED DIFFERENTIATION AND MATURATION OF PLURIPOTENT CELLS INTO HEPATOCYTE LIKE CELLS BY MODULATION OF WNT-SIGNALLING PATHWAY

(75) Inventors: Gabriella Brolén, Gothenburg (SE); Josefina Edsbagge, Torslanda (SE)

(73) Assignee: Takara Bio Europe AB, Gothenburg (SE)

( * ) Notice: Subject to any disclaimer, the term of this patent is extended or adjusted under 35 U.S.C. 154(b) by 0 days.

(21) Appl. No.: 13/636,543

(22) PCT Filed: Mar. 22, 2011

(86) PCT No.: PCT/EP2011/001411
§ 371 (c)(1),
(2), (4) Date: Jan. 2, 2013

(87) PCT Pub. No.: WO2011/116930
PCT Pub. Date: Sep. 29, 2011

(65) Prior Publication Data
US 2013/0095567 A1    Apr. 18, 2013

Related U.S. Application Data

(60) Provisional application No. 61/316,021, filed on Mar. 22, 2010.

(30) Foreign Application Priority Data

Mar. 22, 2010  (DK) ................................. 2010 00234

(51) Int. Cl.
*C12N 5/071*    (2010.01)

(52) U.S. Cl.
CPC .......... *C12N 5/067* (2013.01); *C12N 2501/113* (2013.01); *C12N 2501/115* (2013.01); *C12N 2501/12* (2013.01); *C12N 2501/155* (2013.01); *C12N 2501/16* (2013.01); *C12N 2501/415* (2013.01); *C12N 2502/45* (2013.01); *C12N 2506/02* (2013.01); *C12N 2506/03* (2013.01); *C12N 2506/45* (2013.01)

(58) Field of Classification Search
None
See application file for complete search history.

(56) References Cited

U.S. PATENT DOCUMENTS 8,278,105 B2 * 10/2012 Pera et al. .................... 435/377
2006/0003446 A1  1/2006 Keller et al.
2010/0062527 A1  3/2010 Pera et al.

FOREIGN PATENT DOCUMENTS

| EP | 1 674 563 | 6/2006 |
|---|---|---|
| WO | WO 2007/050043 | 5/2007 |
| WO | WO 2008/094597 | 8/2008 |
| WO | WO 2009/012428 | 1/2009 |
| WO | WO 2009/013254 | 1/2009 |

OTHER PUBLICATIONS

Bone, et al. (2011) "A novel chemically directed route for the generation of definitive endoderm from human embryonic stem cells based on inhibition of GSK-3", Journal of Cell Science, 124: 1992-2000.*

International Search Report mailed on May 20, 2011, issued in corresponding PCT Application PCT/EP2011/001411.

Sadhana Agarwal et al., *Efficient Differentiation of functional Hepatocytes from Human Embryonic Stem Cells*, 26 Stem Cells 1117-1127 (2008).

Yank Bi et al., *Wnt Antagonist SFRP3 Inhibits the Differentiation of Mouse Hepatic Progenitor Cells*, 108 Journal of Cellular Biochemistry 295-303 (2009).

David Hay et al., *Highly efficient differentiation of hESCs to functional hepatic endoderm requires ActivinA and Wnt3a signaling*, 105(34) PNAS 12301-12306 (Aug. 26, 2008).

Chung et al., *Human Embryonic Stem Cell Lines Generated without Embryo Destruction*, 2 Cell Stem Cell 113-117 (2008).

Cai et al., *Directed Differentiation of Human Embryonic Stem Cells into Functional Hepatic Cells*, 45(5) Hepatology 1229-1239 (2007).

European Communication mailed on Feb. 17, 2014, in corresponding European Patent Application No. 11714218.2-1402.

Bone et al., *A novel chemically directed route for the generation of definitive endoderm from human embryonic stem cells based on inhibition of GSK-3*, 124(12) Journal of Cell Science 1992-2000 (May 24, 2011).

(Continued)

*Primary Examiner* — Robert M Kelly
(74) *Attorney, Agent, or Firm* — Buchanan Ingersoll & Rooney PC

(57) ABSTRACT

Provided are improved methods using Glycogen synthase kinase 3 (GSK3) inhibitors by which endodermal cells, notably endodermal cells derived from human pluripotent stem cells (hPS), such as but not limited to hiPS-cells and hES-cells may be differentiated into hepatocyte like cells. The specific modulation of wingless integration gene (WNT)-signalling pathway and use of GSK3 inhibitors achieve direct differentiation and maturation of hepatocytes derived from human pluripotent stem (hPS) cells. GSK-3 inhibitors, when added to the growth medium at certain developmental stages, leads to more mature and functional features for the hepatocyte like cells as well as more pure and homogenous populations of hepatocyte like cells. Provided are also hepatocyte like cells obtained by these methods as well as compositions comprising them.

12 Claims, 79 Drawing Sheets

(56) References Cited

OTHER PUBLICATIONS

Ghodsizadeh et al., *Generation of Liver Disease-Specific Induced Pluripotent Stem Cells Along with Efficient Differentiation to Functional Hepatocyte-Like Cells*, 6 Stem Cell Rev and Rep 622-632 (2010).

Rashid et al., *Modeling inherited metabolic disorders of the liver using human induced pluripotent stem cells*, 120(9) The Journal of Clinical Investigation 3127-3136 (Sep. 2010).

Song et al., *Efficient generation of hepatocyte-like cells from human induced pluripotent stem cells*, Cell Research 1-10 (2009).

Sullivan et al., *Generation of Functional Human Hepatic Endoderm from Human Induced Pluripotent Stem Cells* 51(1) Hepatology 329-335 (2010).

Zhou et al., *Differentiation of mouse embryonic stem cells into hepatocytes induced by a combination of cytokines and sodium butyrate*, 109(3) Journal of Cellular Biochemistry 606-614 (Feb. 15, 2010).

Official Action issued in corresponding Japanese Patent Application No. 2013-500382, mailed on Jun. 17, 2015, with English translation.

* cited by examiner

Overview: Derivation of hepatocytes-like cells from hPS.

- ■ ID
- ☐ VH1
- ▨ Maturation Media I or II (MM I or II)
- ▨ GSK3 Inhibitor

Variants of protocol as depicted in figure 1 and described in example 2, to differentiate hPS to hepatocytes i.
Day  0   3   4          10                    30 ii.
Day  0   3   4          10                    30 iii.
Day  0   3   4          10                    30 iv.
Day  0   3   4          10                    30

■ • ID

□ • VH1

▨ • Maturation Media (MM) I or II

▨ • GSK3 Inhibitor

Media and stages in the protocol of inducing hPS to hepatocyte-like cells.

A)

B)

C)

■ • ID (Activin A supplemented media)
☐ • VH1 (PPI)
▦ • SM
▨ • BM2 or ModII / Maturation media (MM) I or II
▧ • GSK3 inhibitor

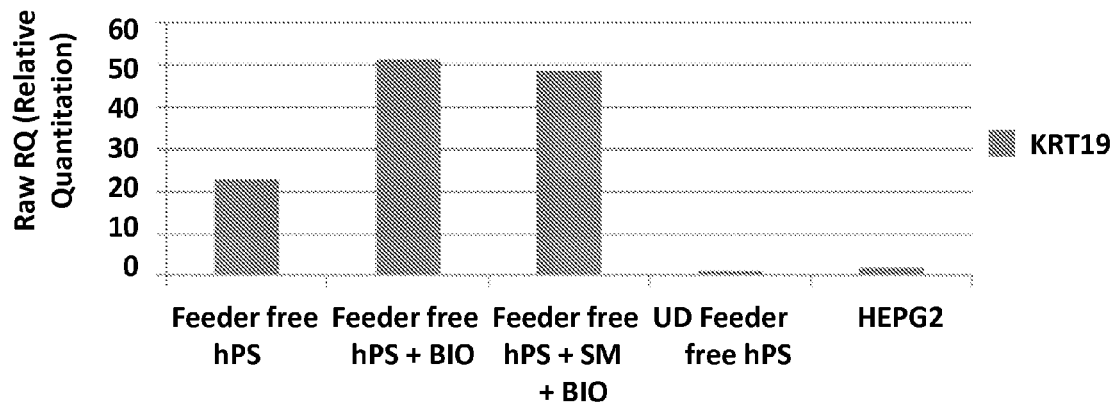
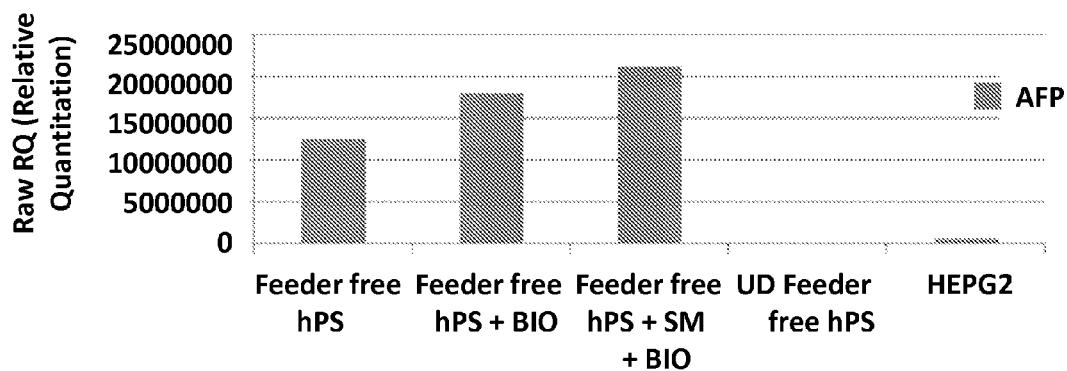
Fig. 4B (Con't)

Beta-catenin and Dapi staining of hES-HEP – BIO (A) and hES-HEP + BIO (B) Beta-catenin is localized at the cell membrane in hES-HEP cultures not treated and treated with BIO. Beta-catenin in the cytoplasm and nuclei is commonly observed in BIO treated hES-HEP cultures. Day21, 20x

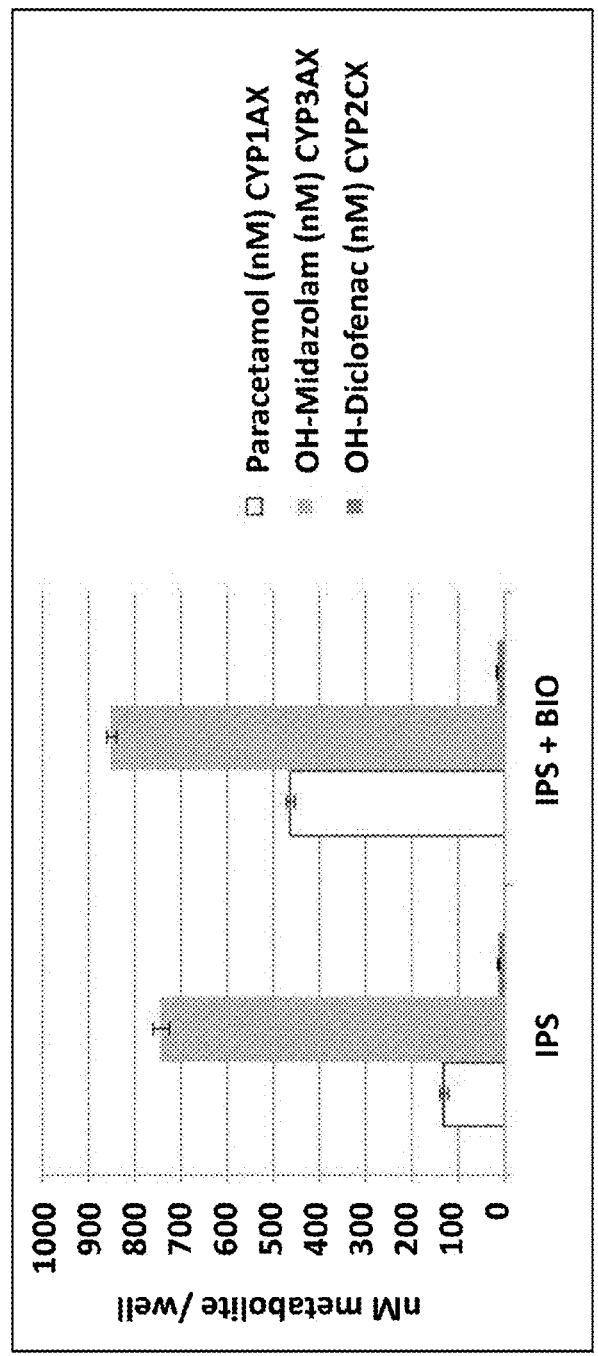

QrtPCR of hepatocyte-like cells derived from hiPS cells, HepG2 cells and undifferentiated cells (UD) are used as control"

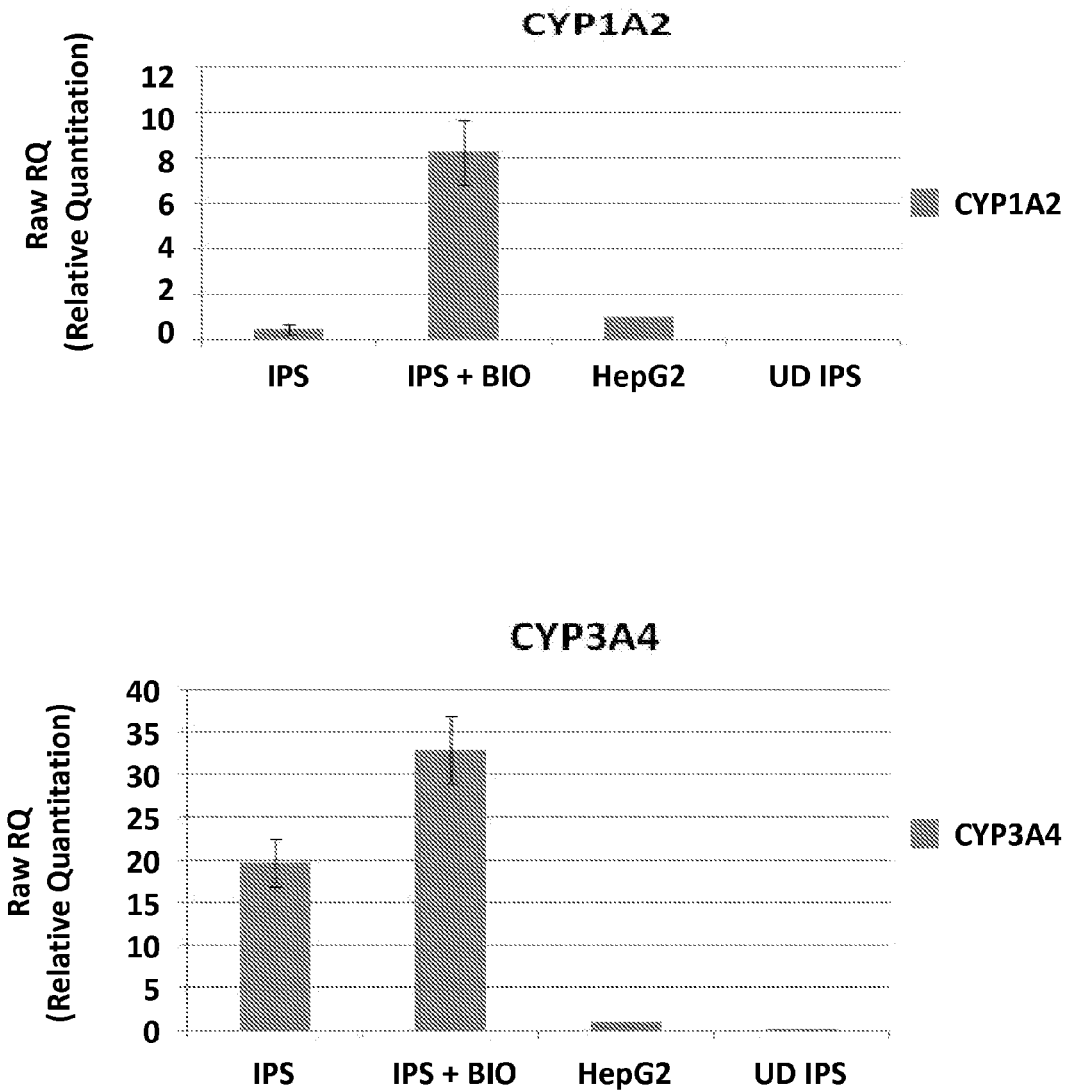
Fig. 5B (Con't)

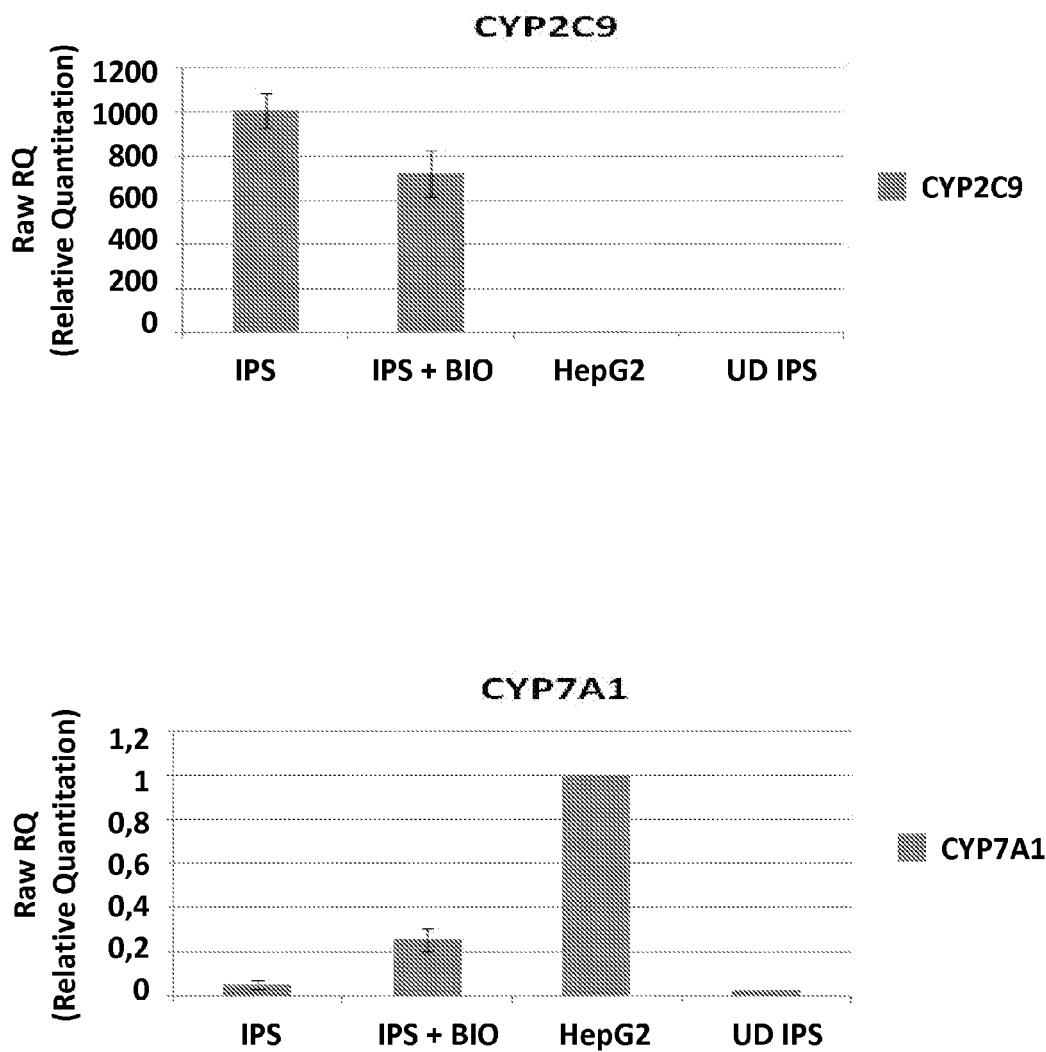
Fig. 5B (Con't)

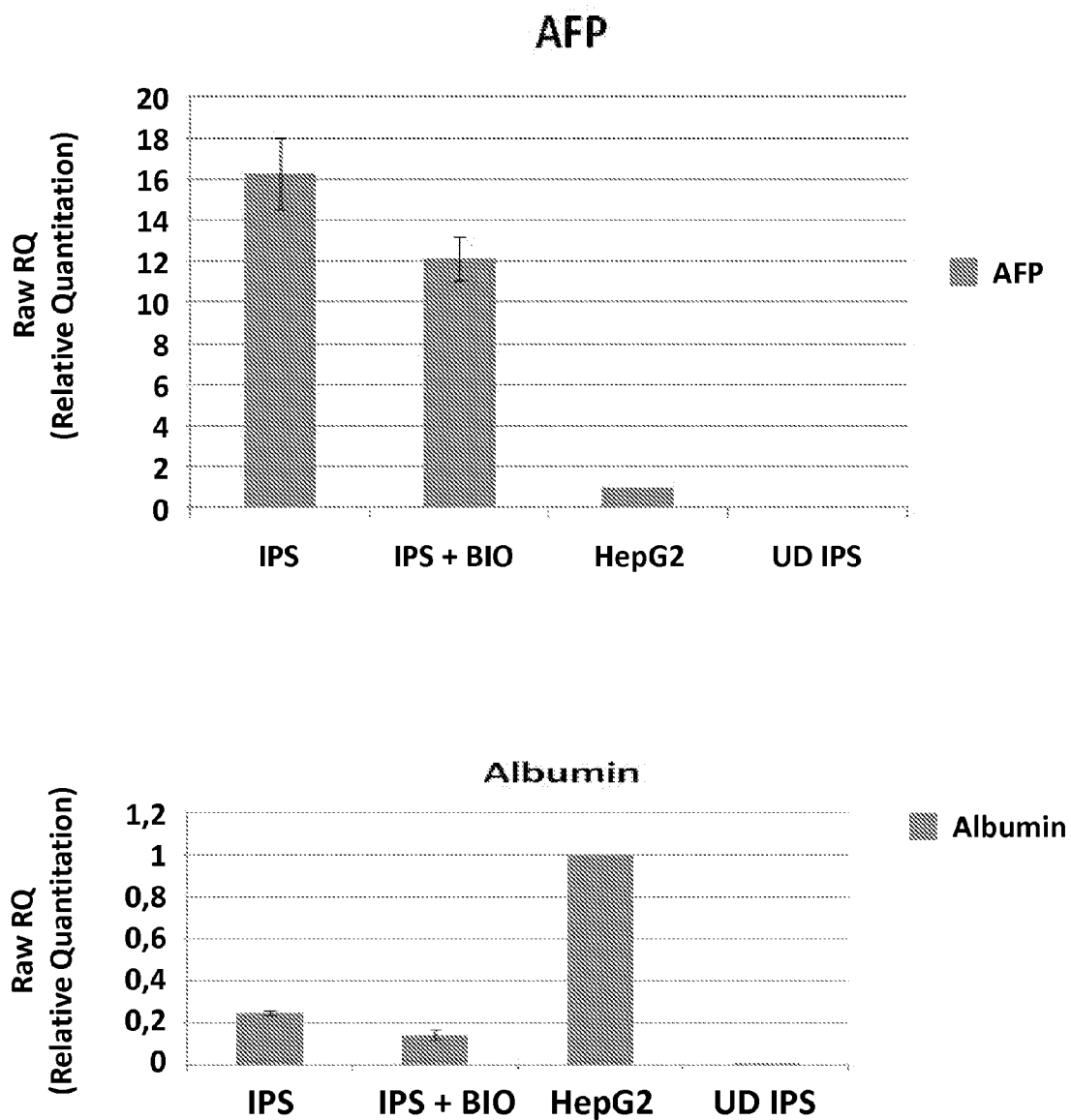
Fig. 5B (Con't)

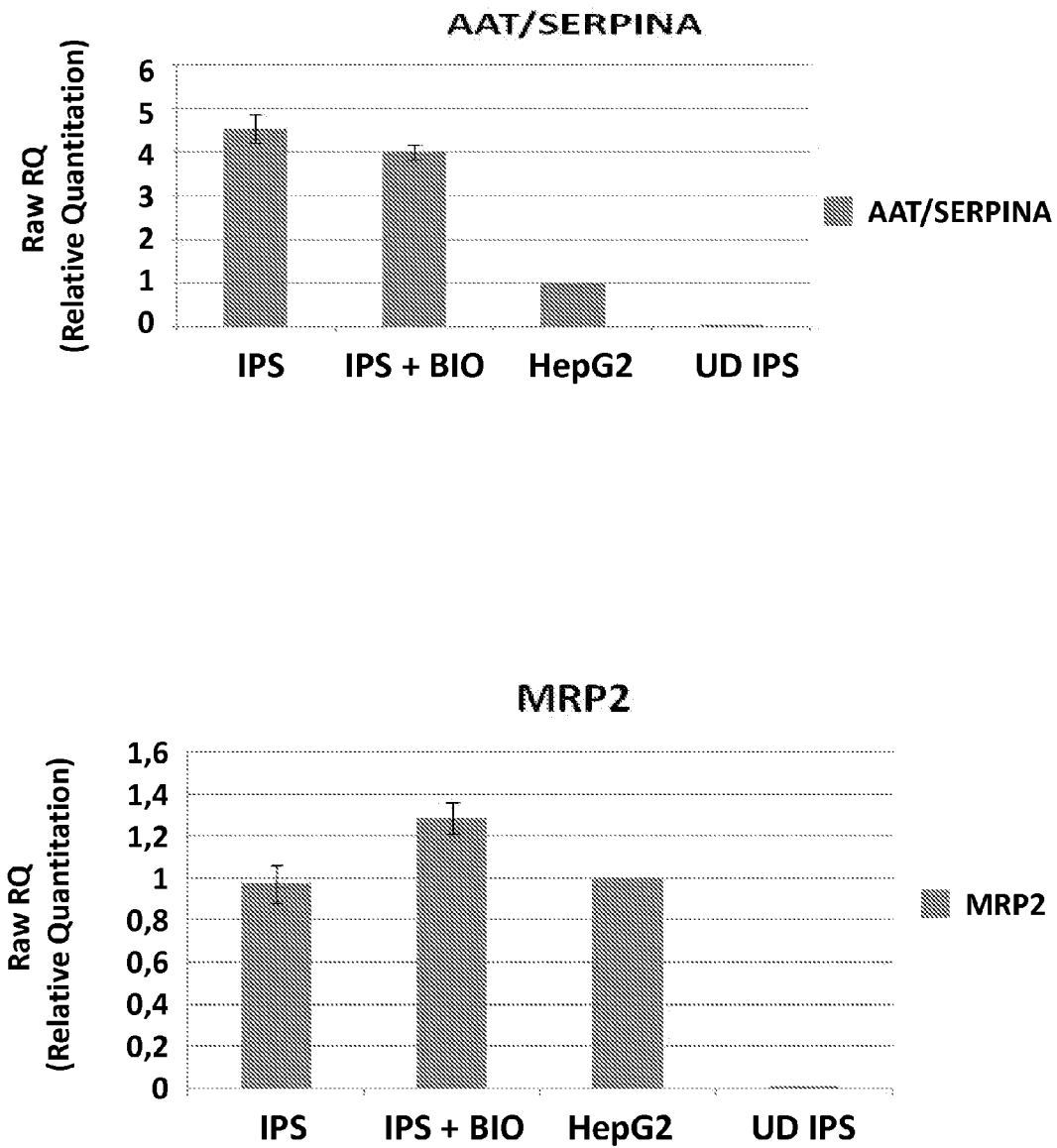
Fig. 5B (Con't)

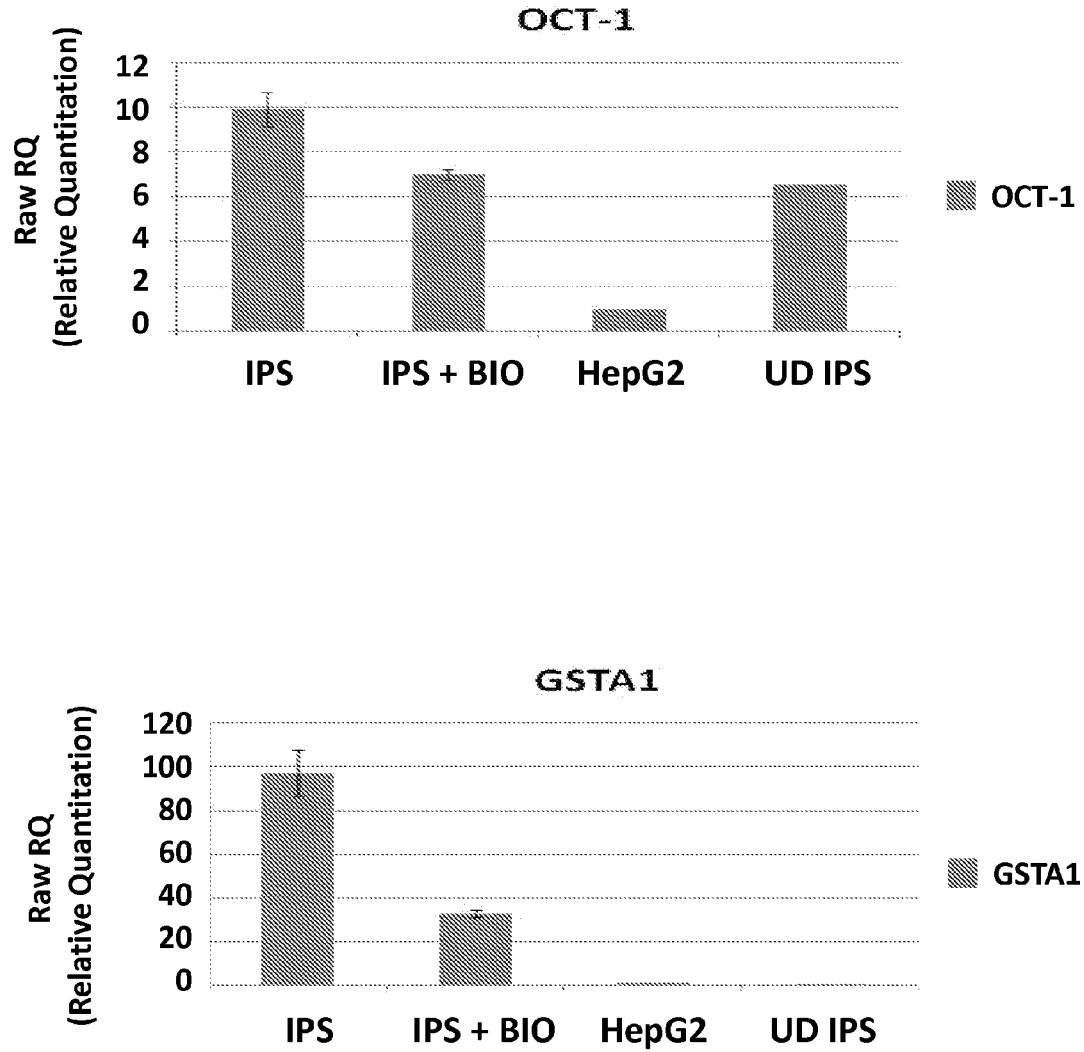
Fig. 5B (Con't)

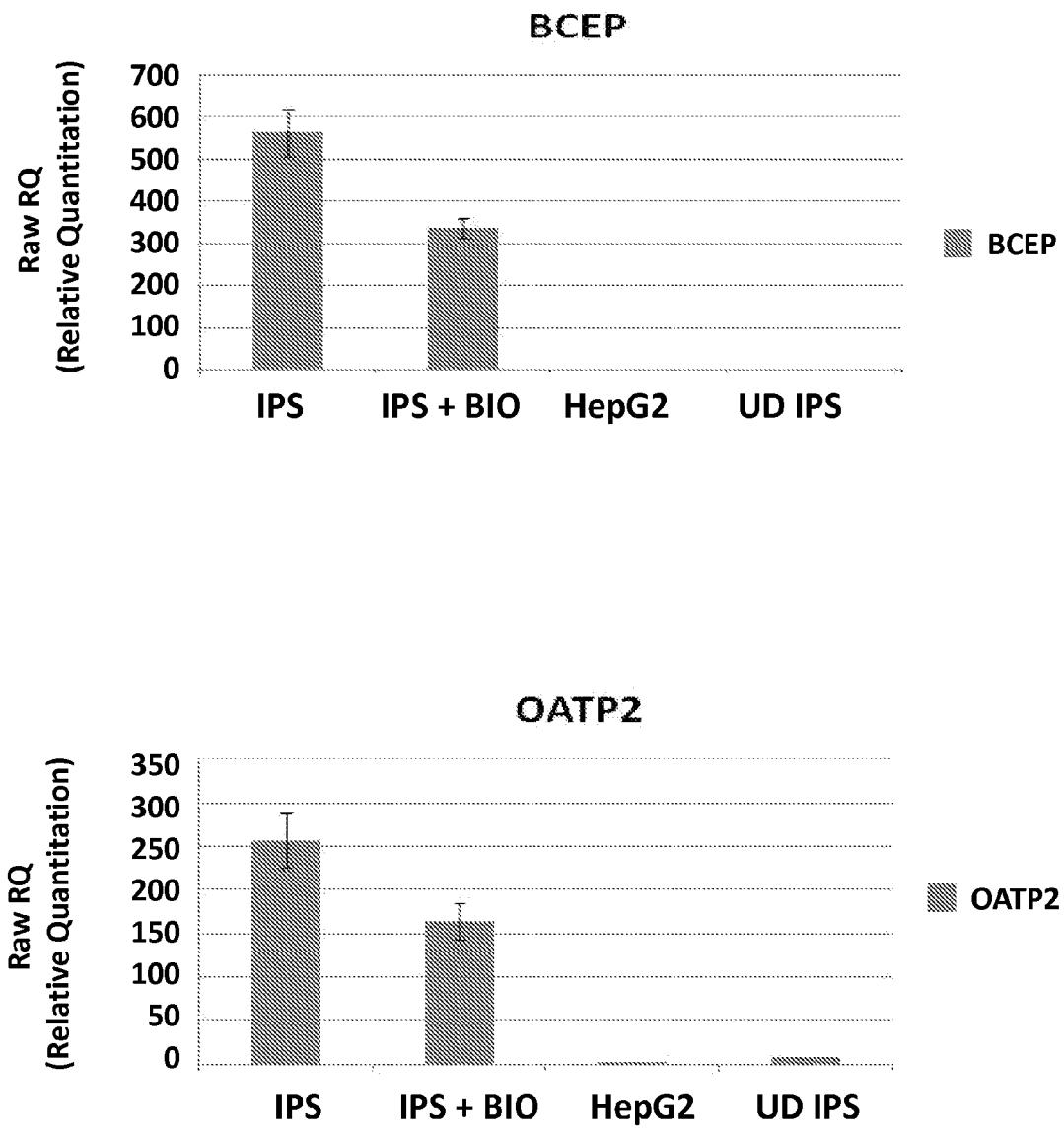
Fig. 5B (Con't)

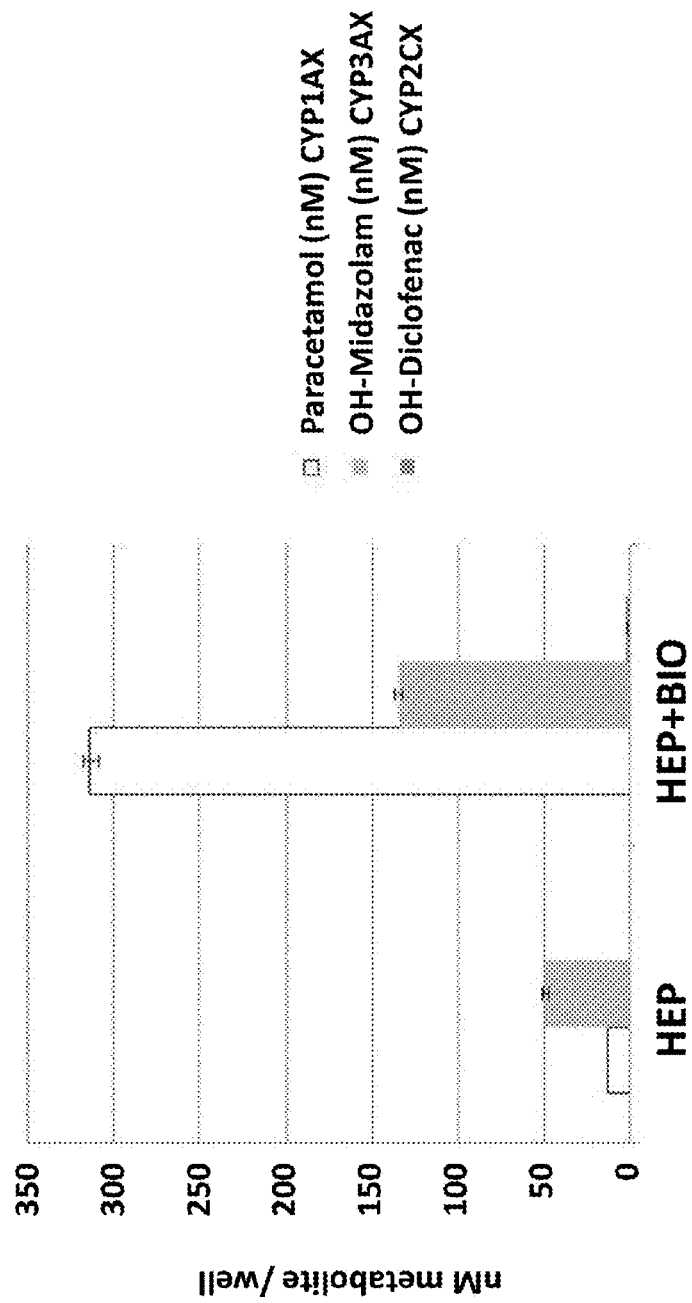

QPCR; hPS +/- BIO, N=4.

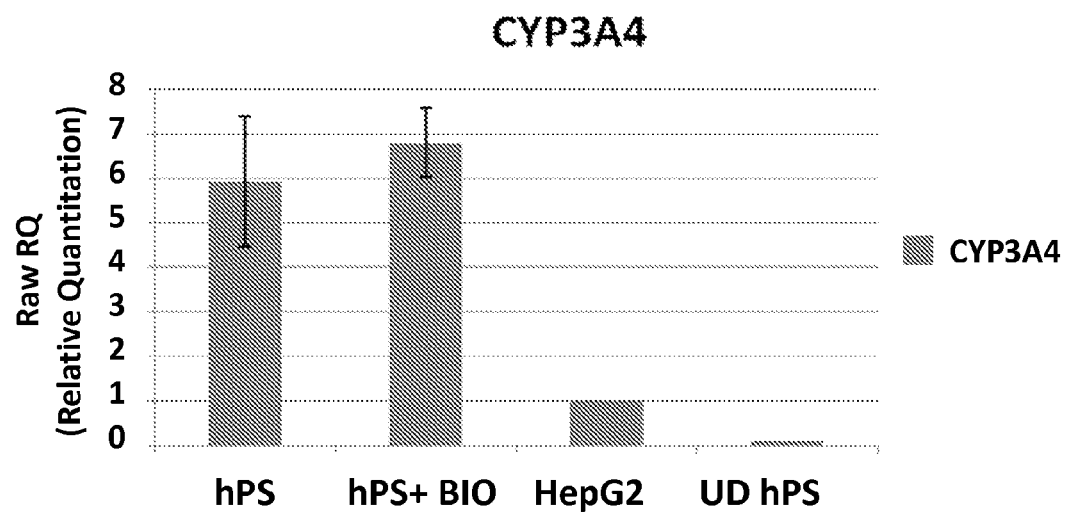
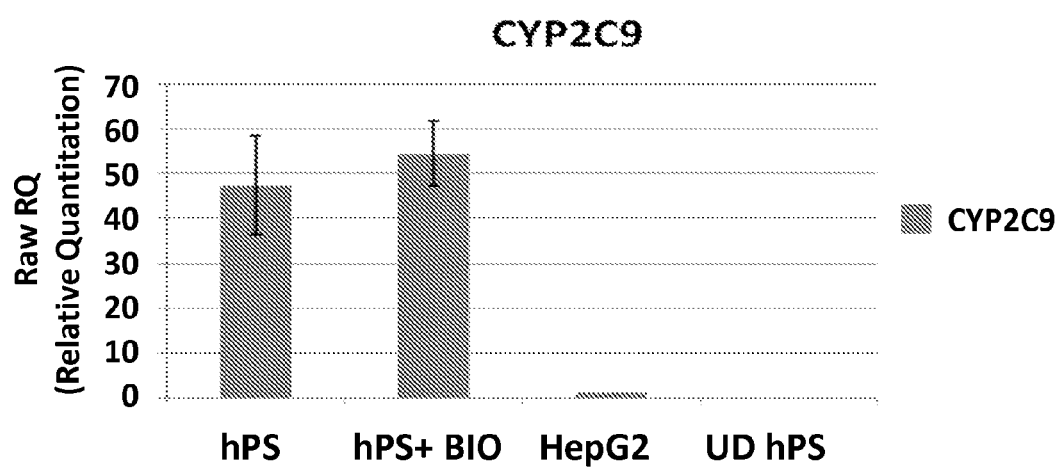
Fig. 6B (Con't)

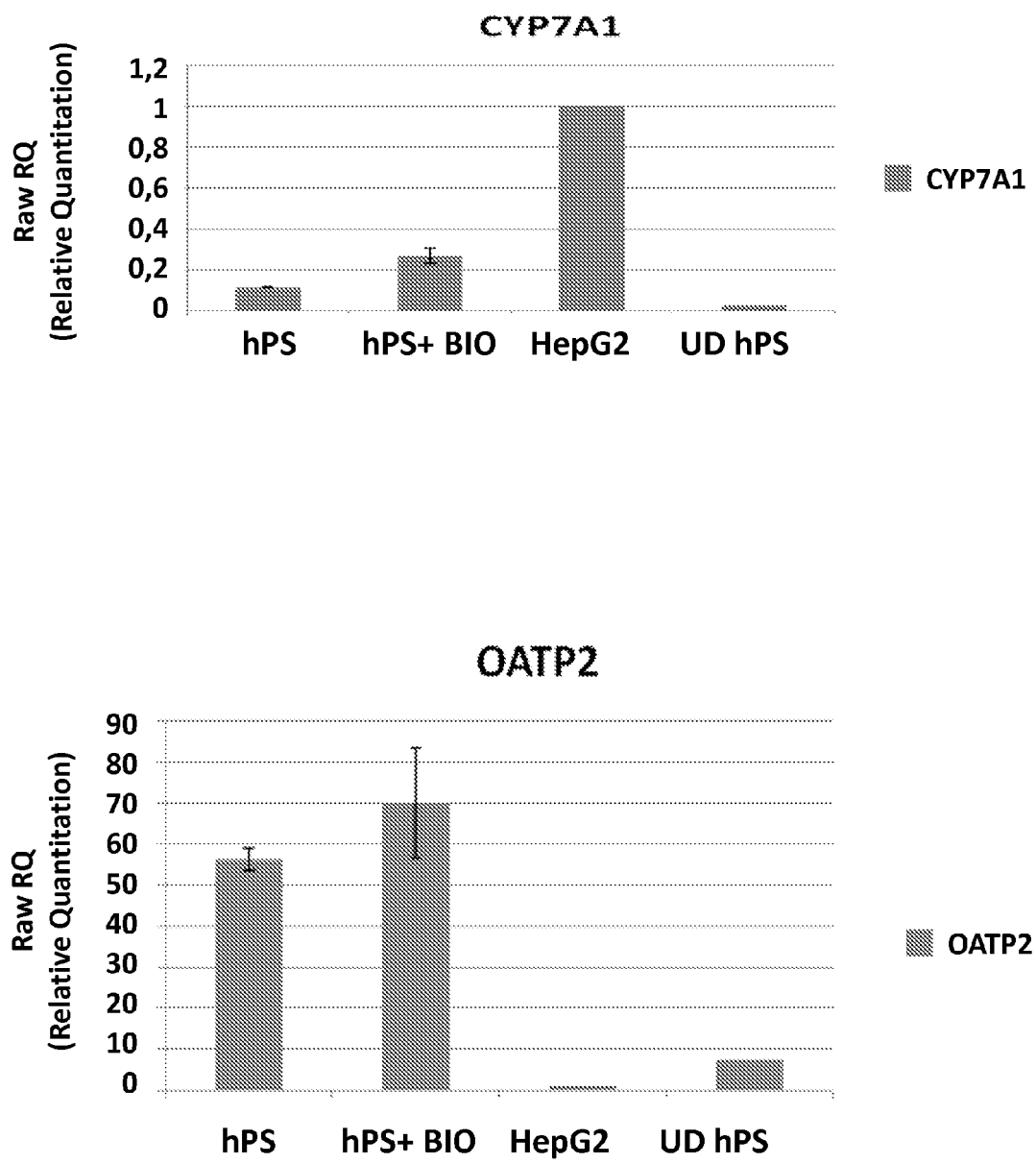
Fig. 6B (Con't)

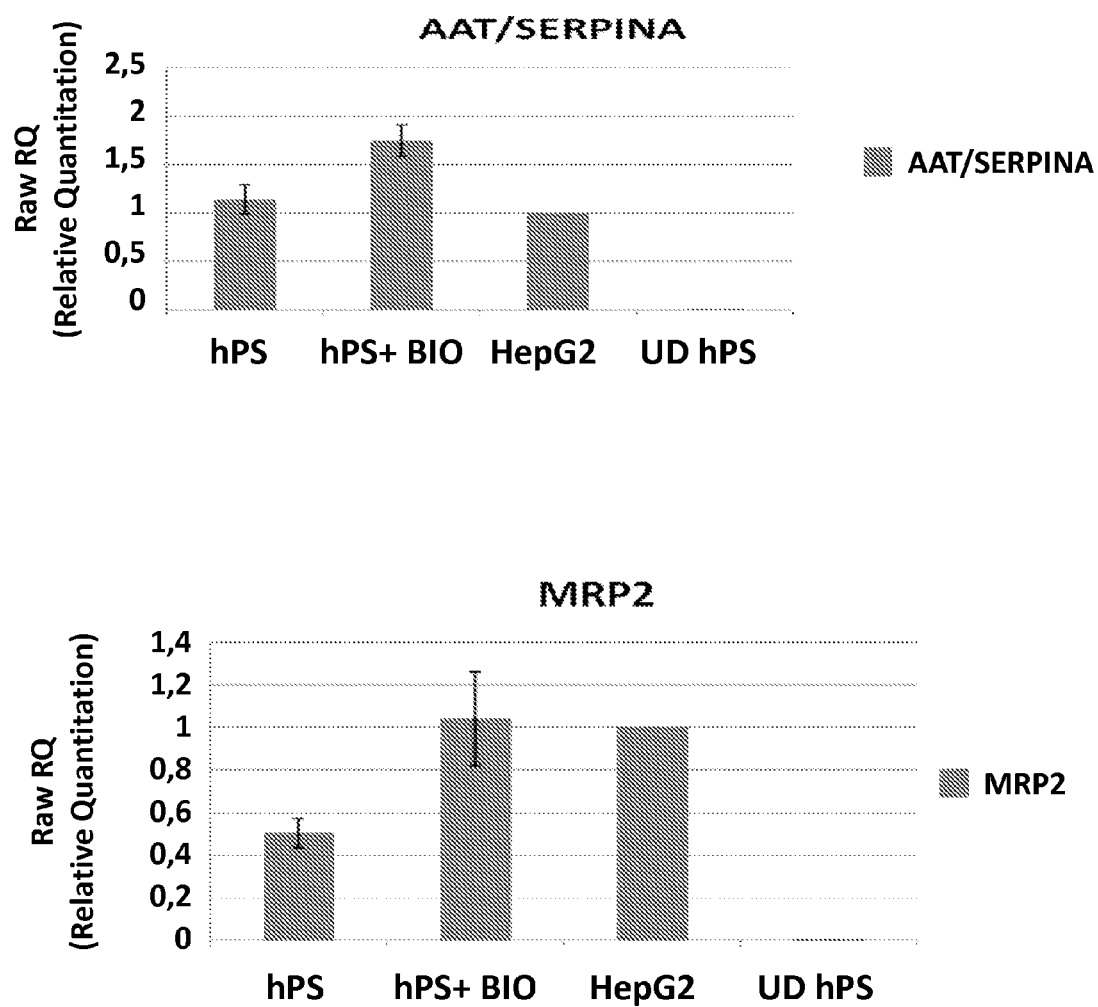
Fig. 6B (Con't)

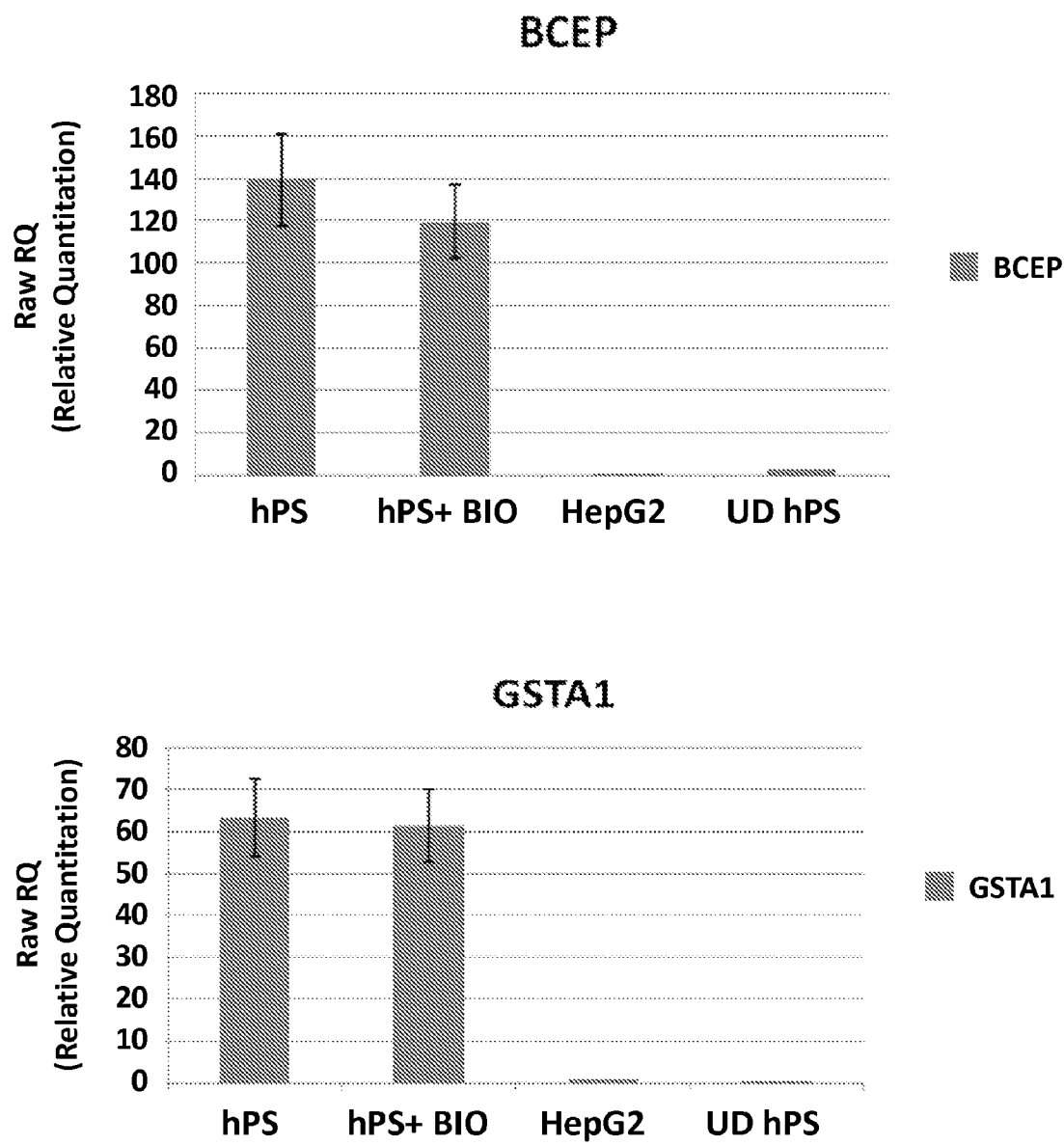
Fig. 6B (Con't)

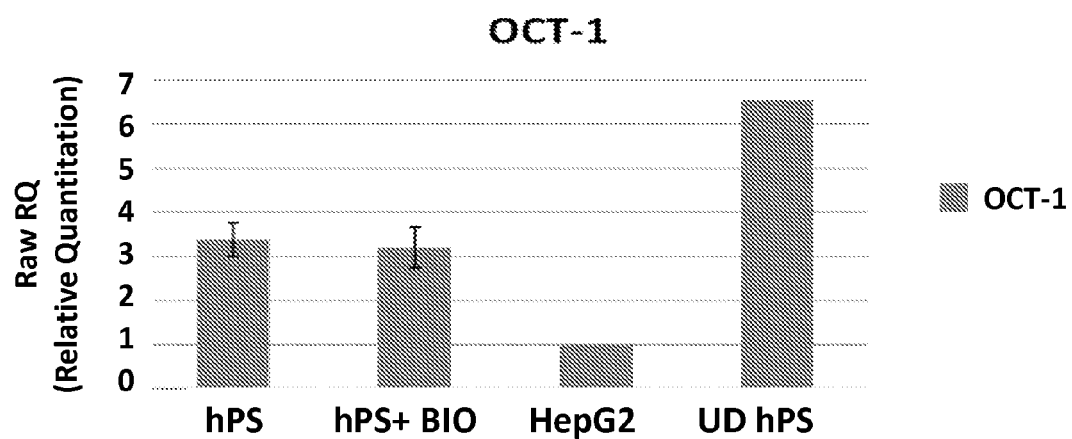
Fig. 6B (Con't)

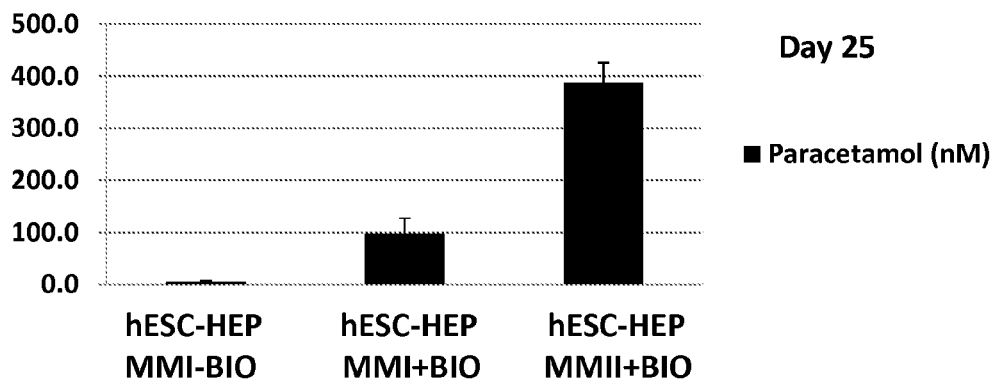
| Fold Change | MM I - BIO | MM I + BIO |
|---|---|---|
| Day 16-18 | 1 | 13 |
| Day 20-21 | 1 | 18 |
| Day 25 | 1 | 18 |
| Fold Change | MM I + BIO | MM II + BIO |
|---|---|---|
| Day 16-18 | 1 | 2.8 |
| Day 20-21 | 1 | 3.0 |
| Day 25 | 1 | 4.0 |
Fig. 7A (Con't)

Fold change of CYP1A1 and 1A2 gene expression levels in hESC-HEP MMII+BIO compare to HepG2.

CYP1A2 immunocytochemistry of in vitro derived hepatocyte-like cells, MMII + BIO, day 19

Differentiation of hESC derived hepatocytes in the presence of GSK3 inhibitor purifies hepatocytes from other cell types.

+ 1,5µM BIO

Modulation of Wnt-signalling at mid (days 3-9) and late (days 10-23)

| Treatment | Purity of hESC-HEP |
|---|---|
| hESC-HEP +BIO (3,5µM &1,5µM) | Ca 60% |
| hESC-HEP +SB216763 (25µM) | Ca 60% |
| hESC-HEP +Kenapaullone (25µM) | Ca 50% |
| hESC-HEP +Indirubin-3´-monoxime (25µM) | Ca 60% |
| hESC-HEP | Ca 25% |

Modulation of Wnt-signalling at late (day 10+)

| Treatment | Purity of hESC-HEP |
|---|---|
| hESC-HEP +BIO (3,5µM &1,5µM) | Ca 70% |
| hESC-HEP +SB216763 (25µM) | Ca 60% |
| hESC-HEP +Kenapaullone (25µM) | Ca 50% |
| hESC-HEP +Indirubin-3´-monoxime (25µM) | Ca 60% |
| hESC-HEP | Ca 25% |

Fig. 8B (Con't)

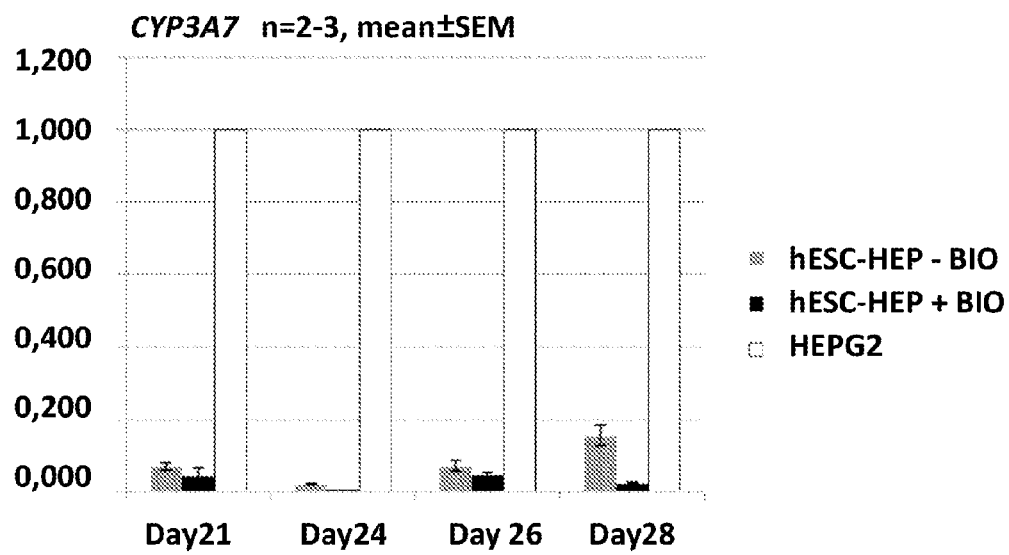
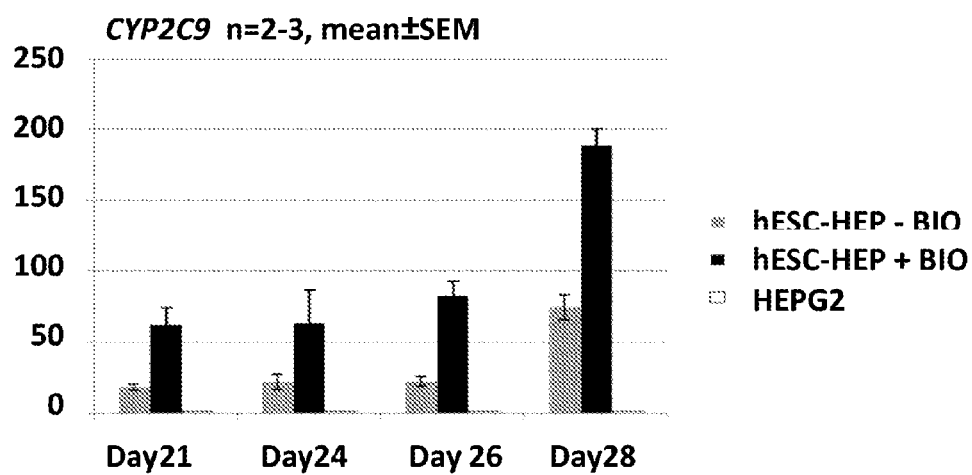
Fig. 10A (Con't)

General Liver Markers

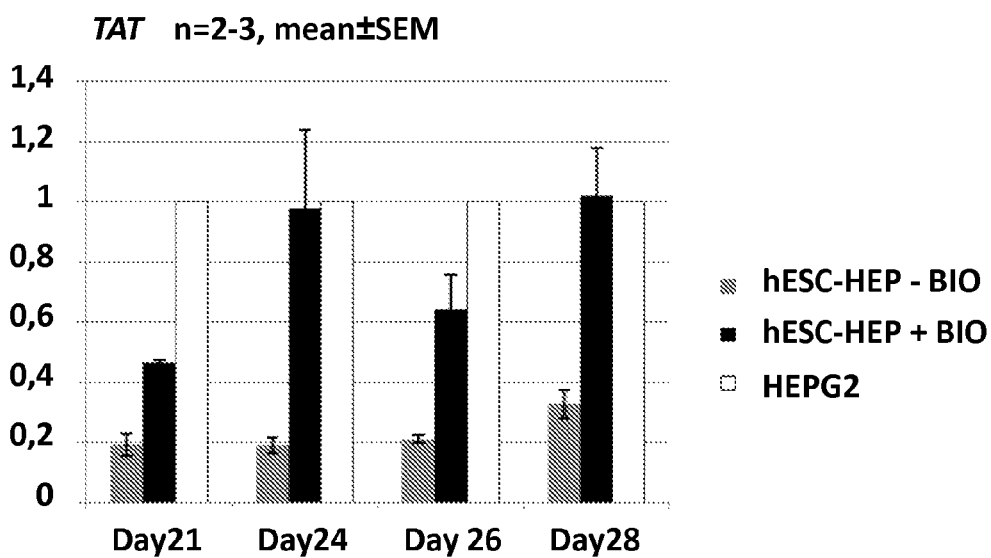
Fig. 10D (Con't)

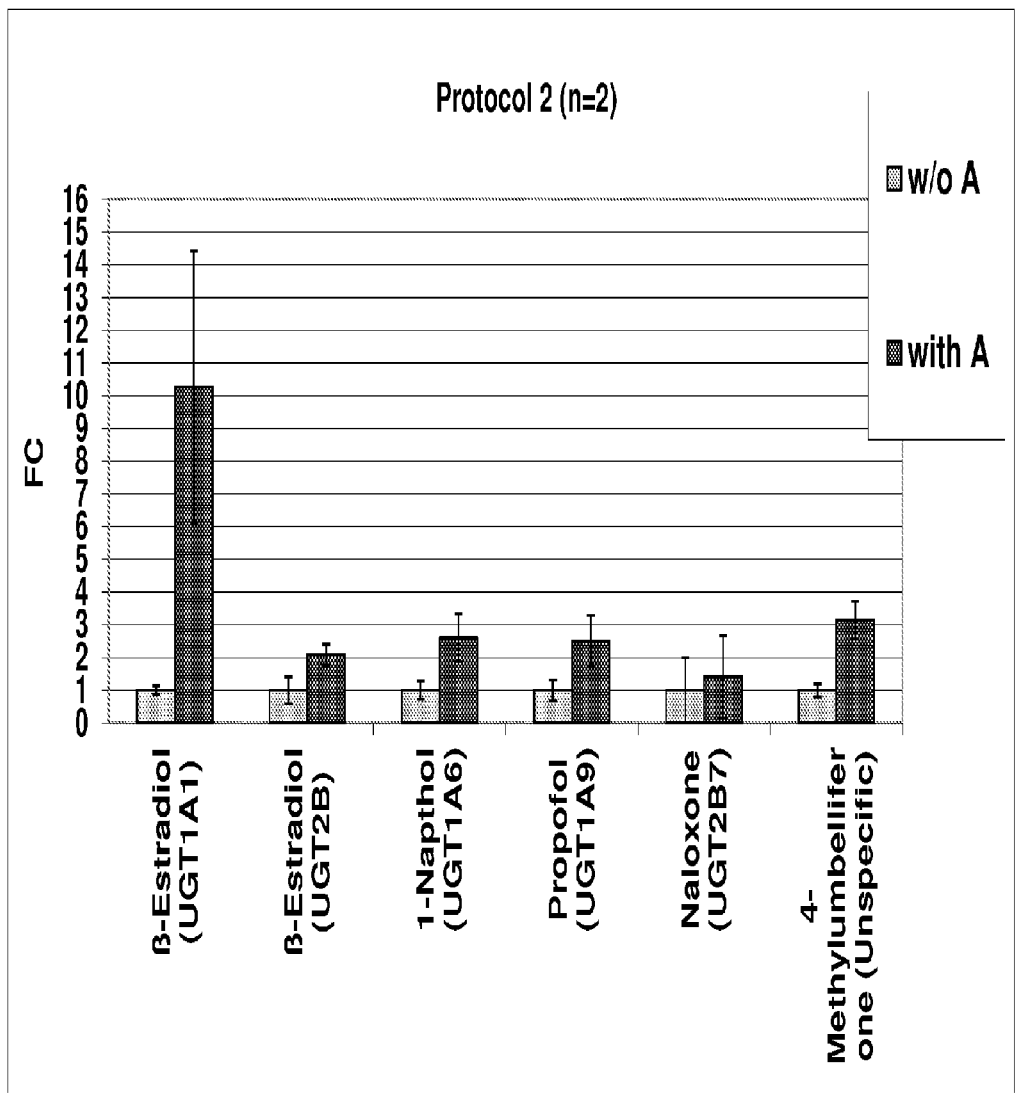
Fig. 11 (Con't)

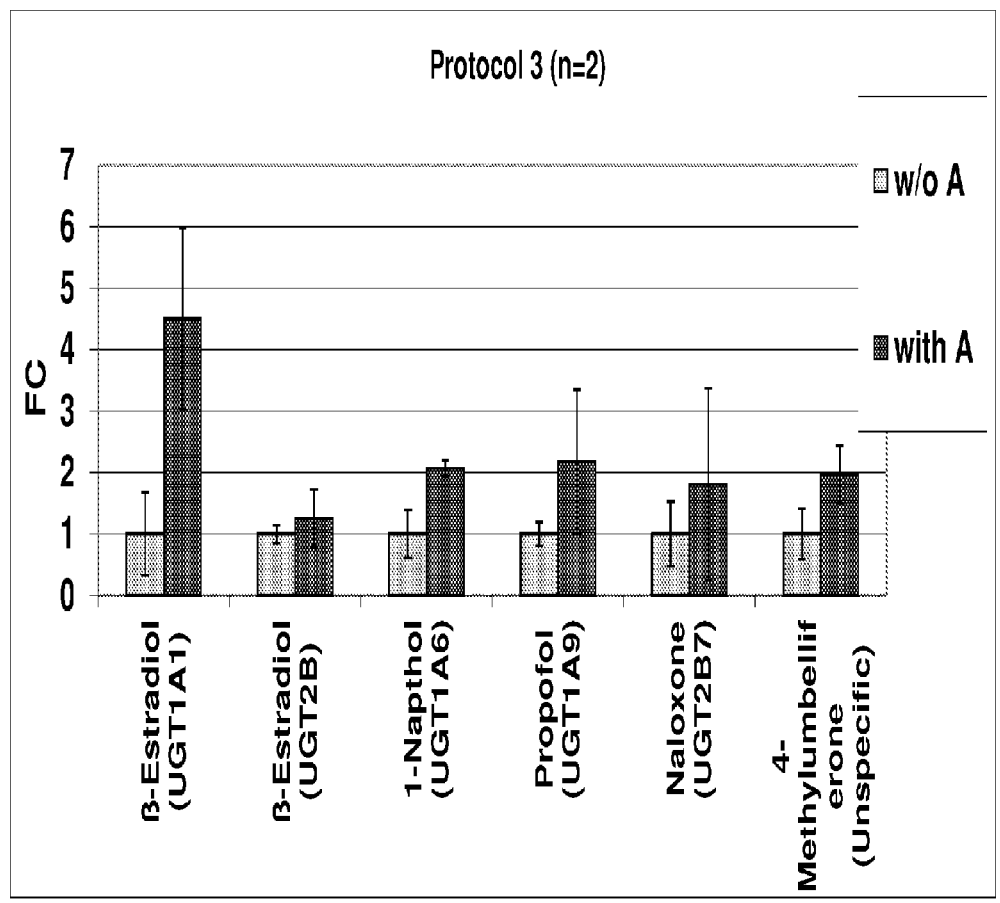
Fig. 11 (Con't)

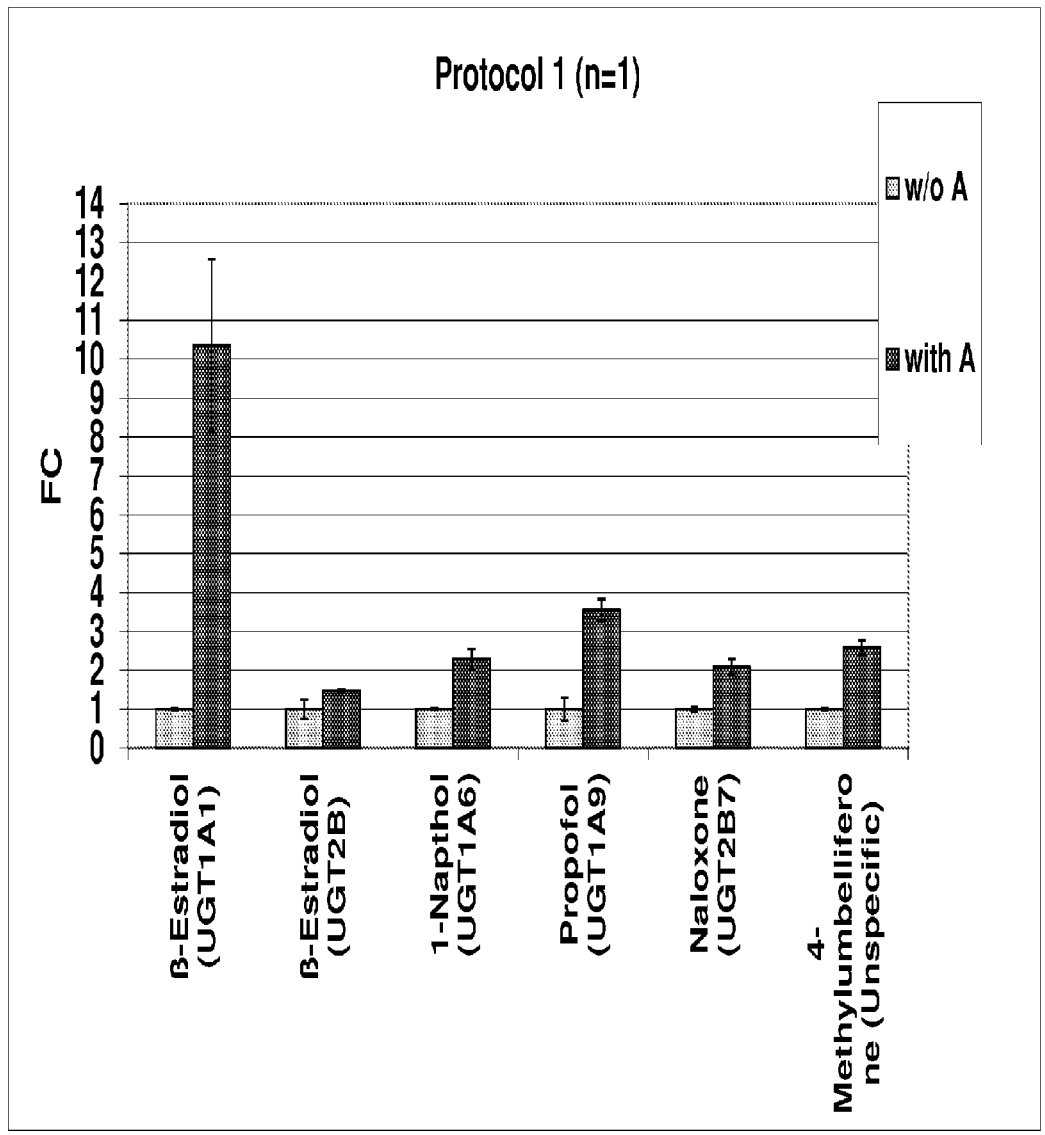
Fig. 11 (Con't)

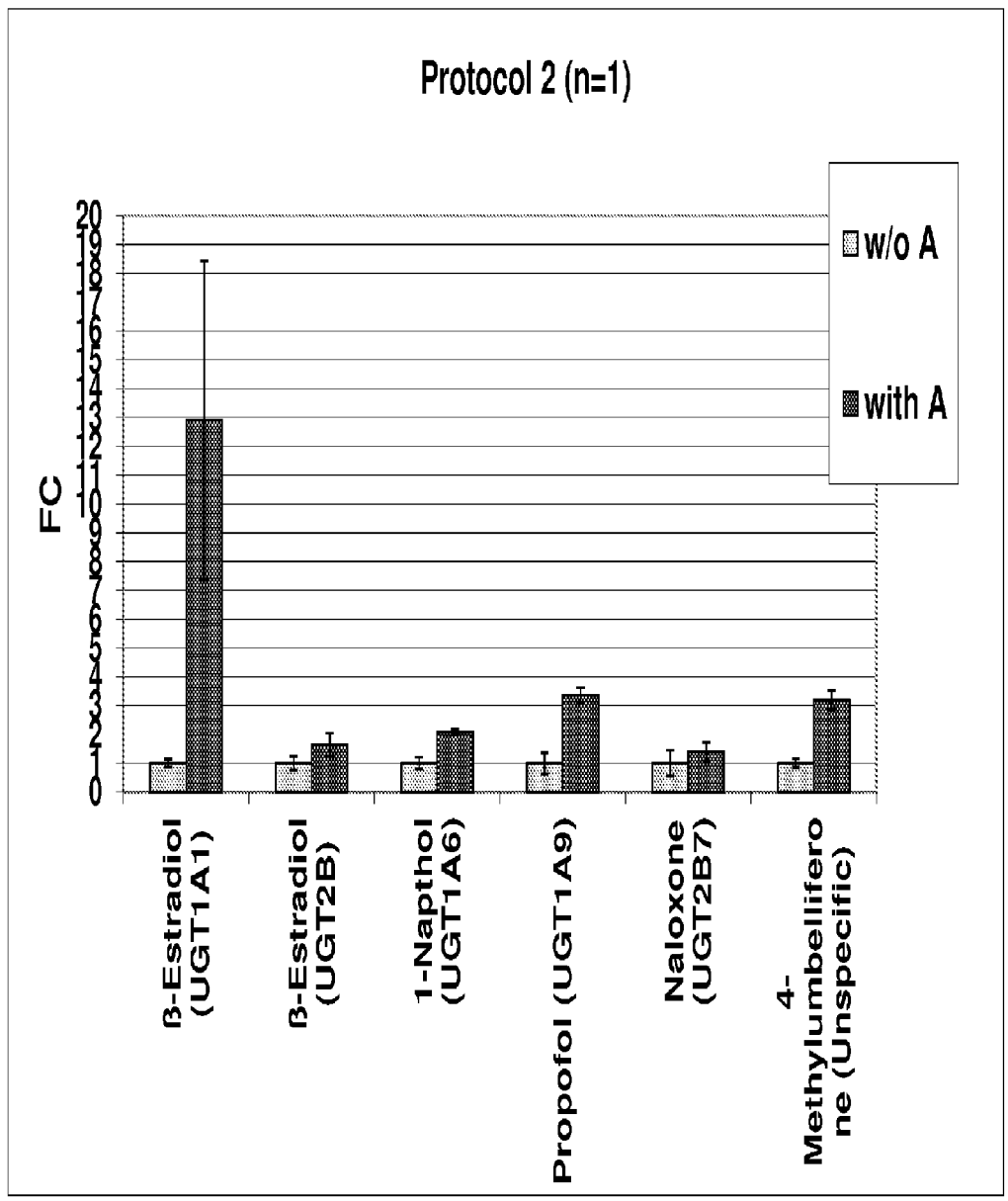
Fig. 11 (Con't)

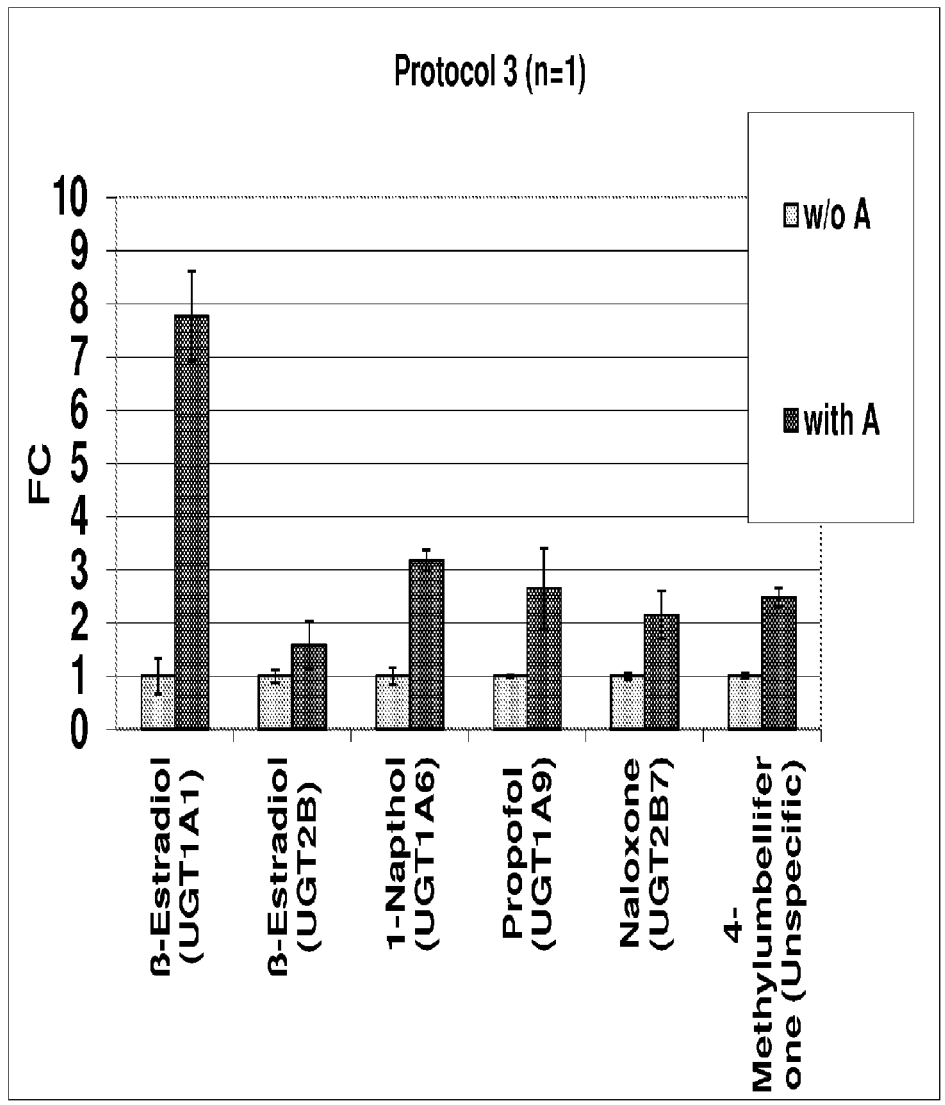
Fig. 11 (Con't)

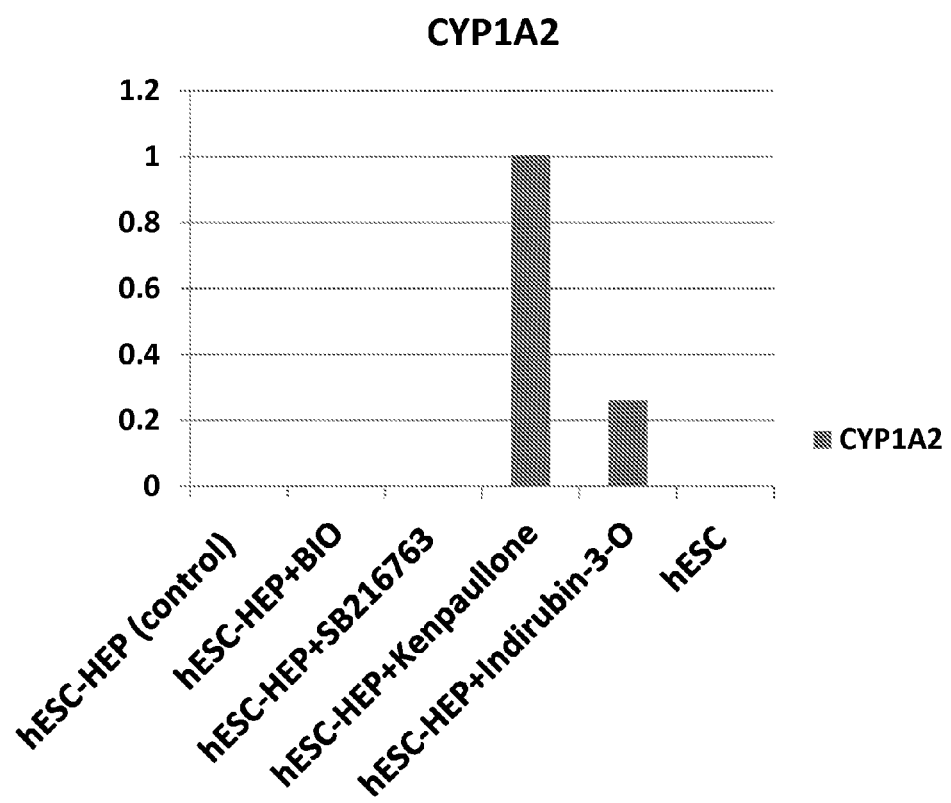
Fig. 12A (Con't)

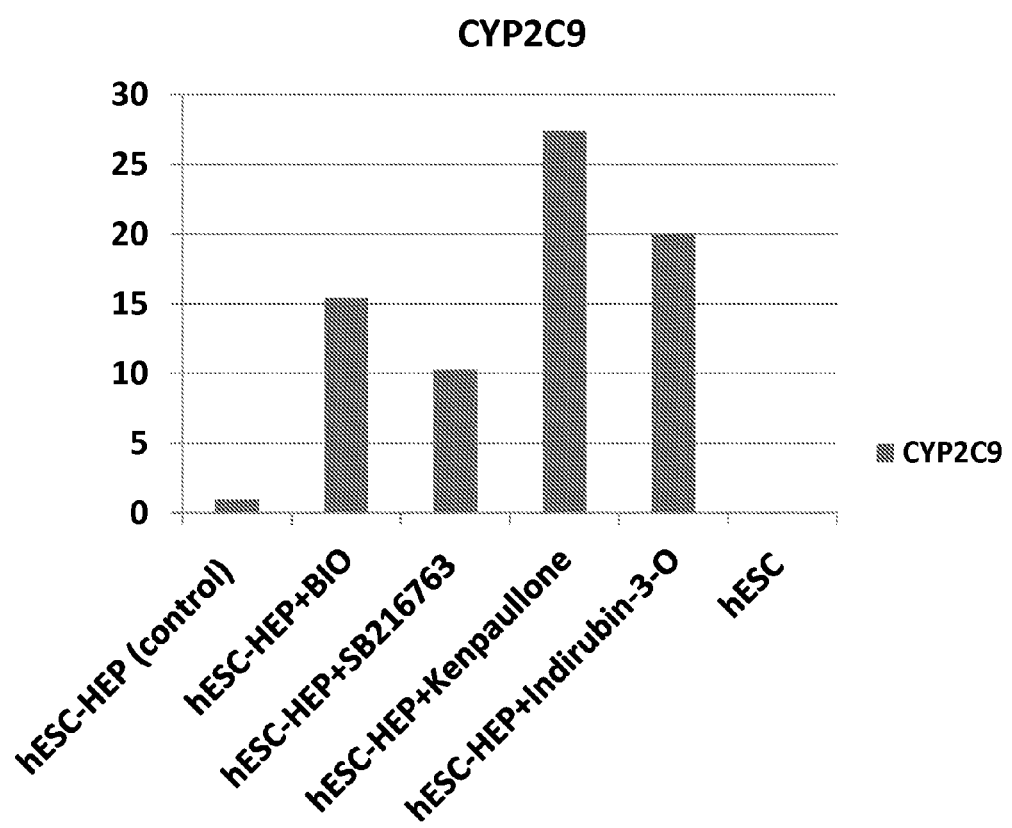
Fig. 12A (Con't)

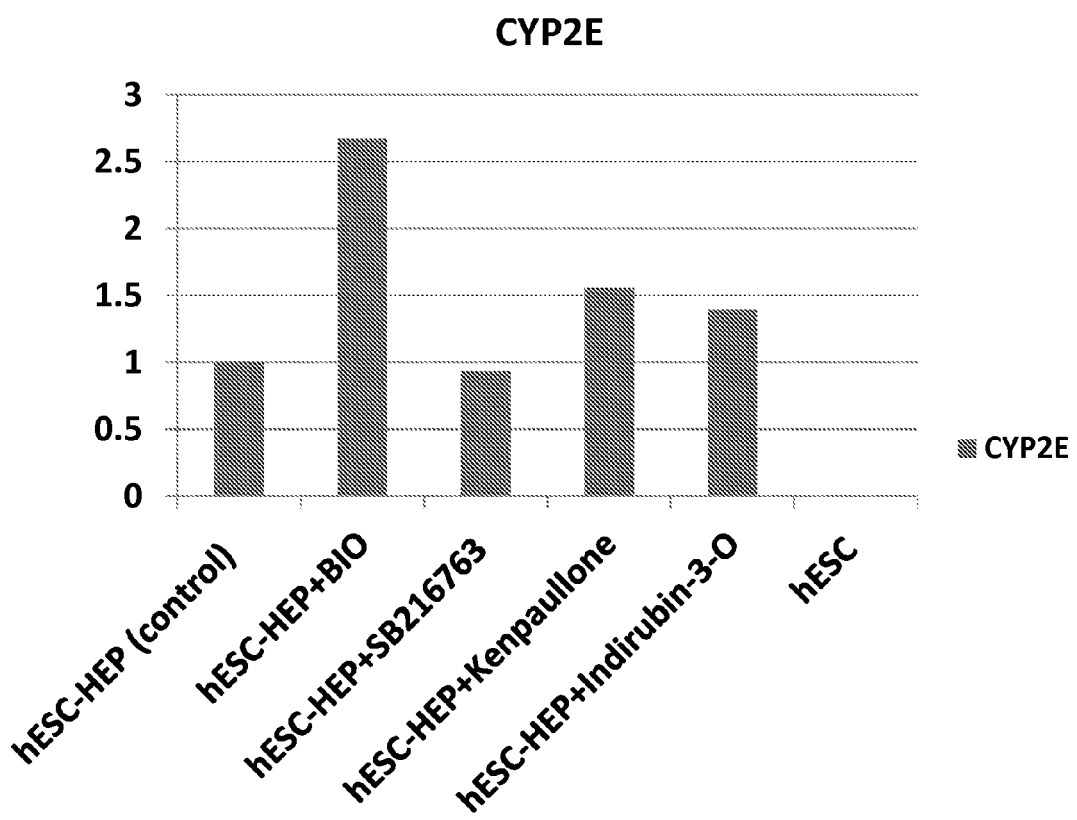
Fig. 12A (Con't)

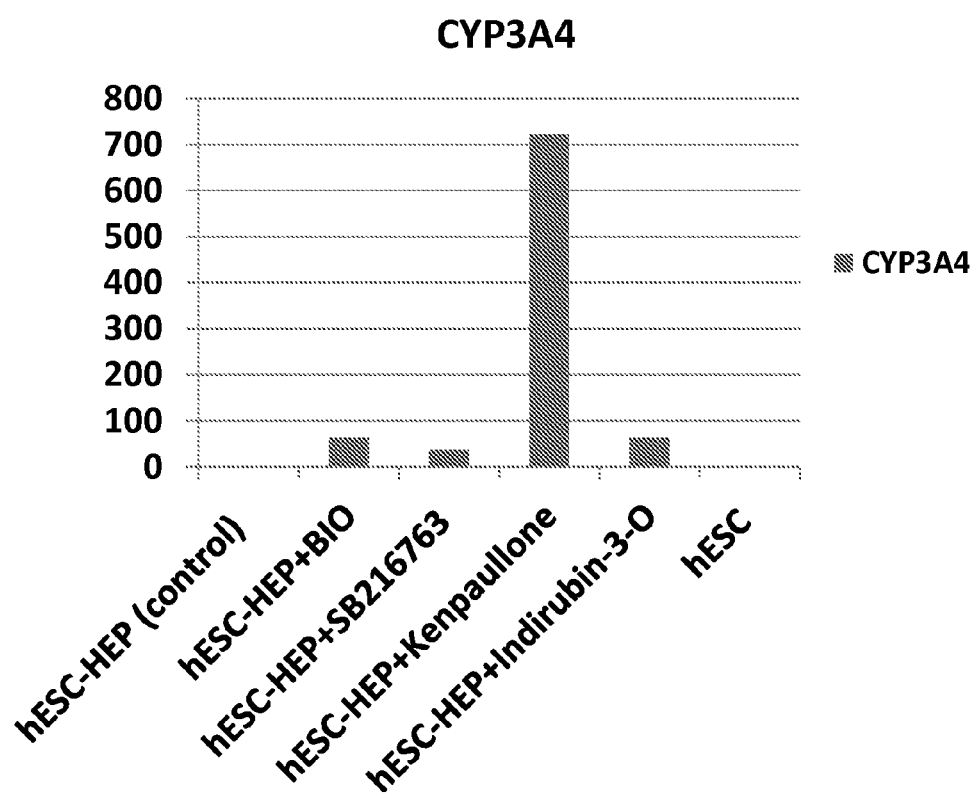
Fig. 12A (Con't)

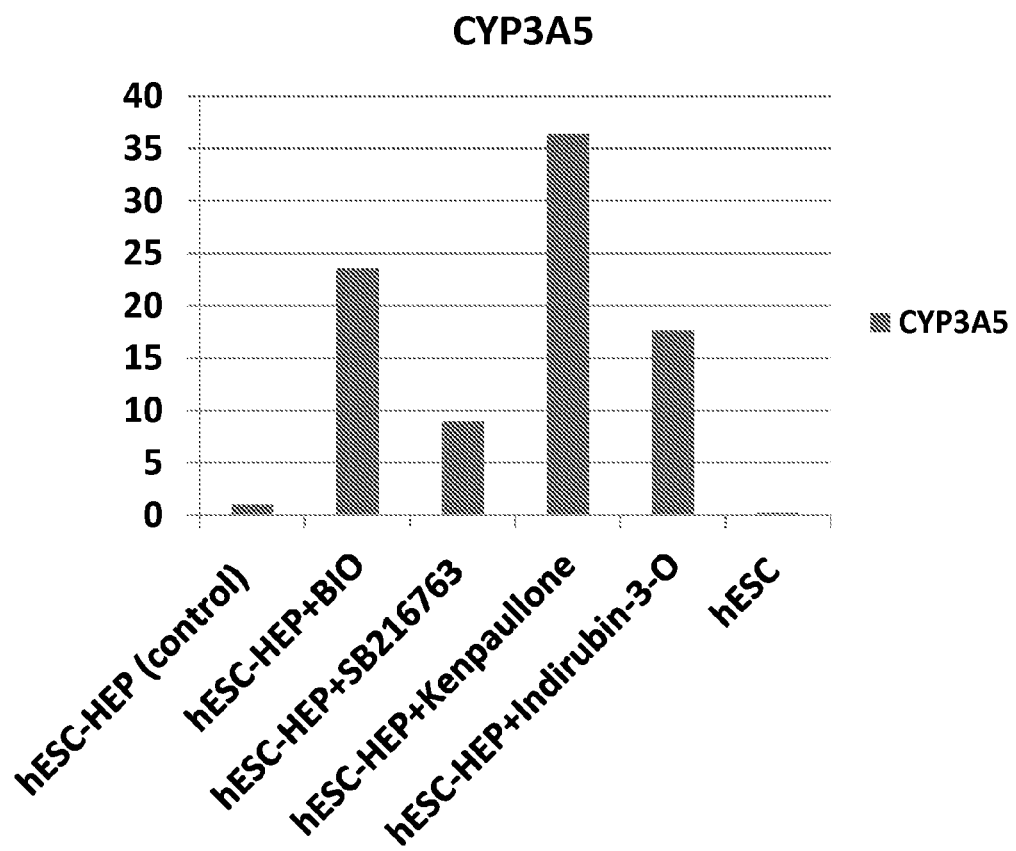
Fig. 12A (Con't)

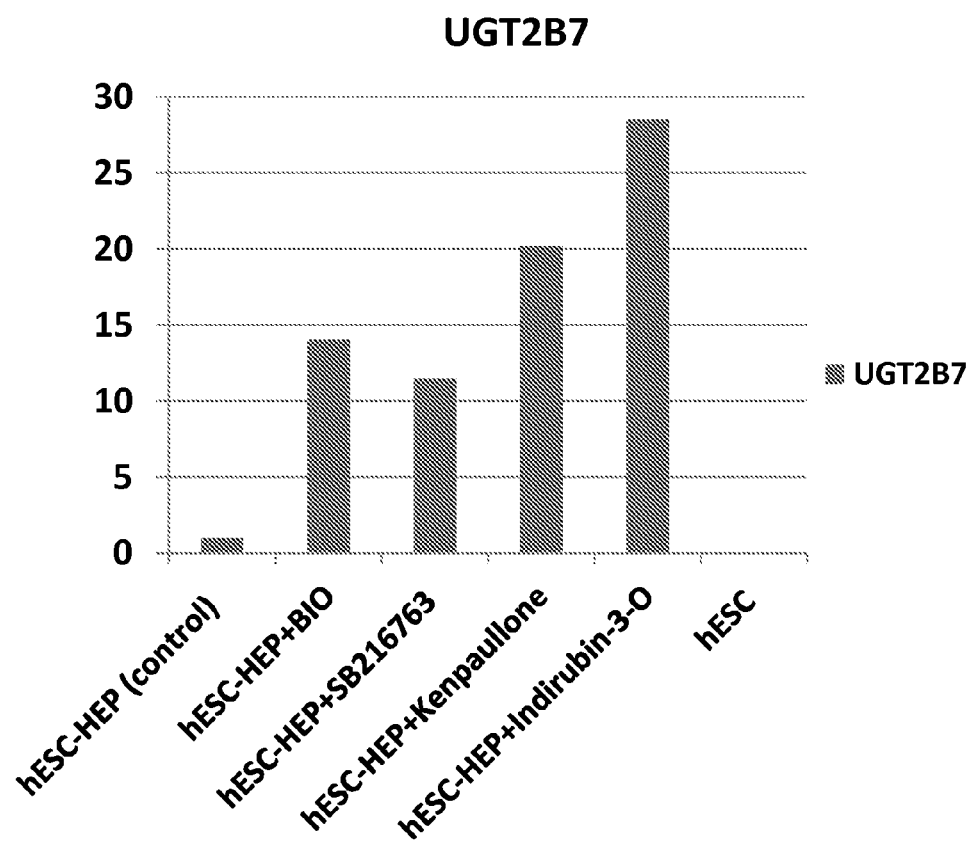
Fig. 12B (Con't)

Page 38 in the original document. Figure 12B
"Real Time RTPCR from hESC-HEP generated using non-BIO GSK-3 inhibitors at day 10+ timepoint"
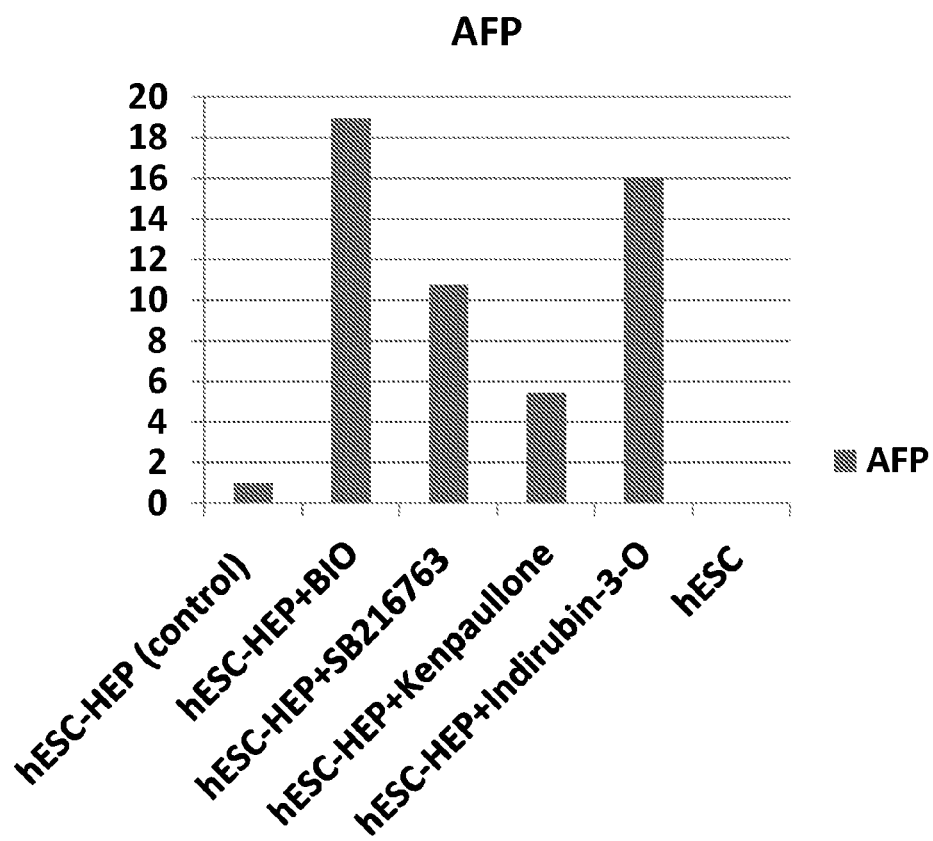
Fig. 12B (Con't)

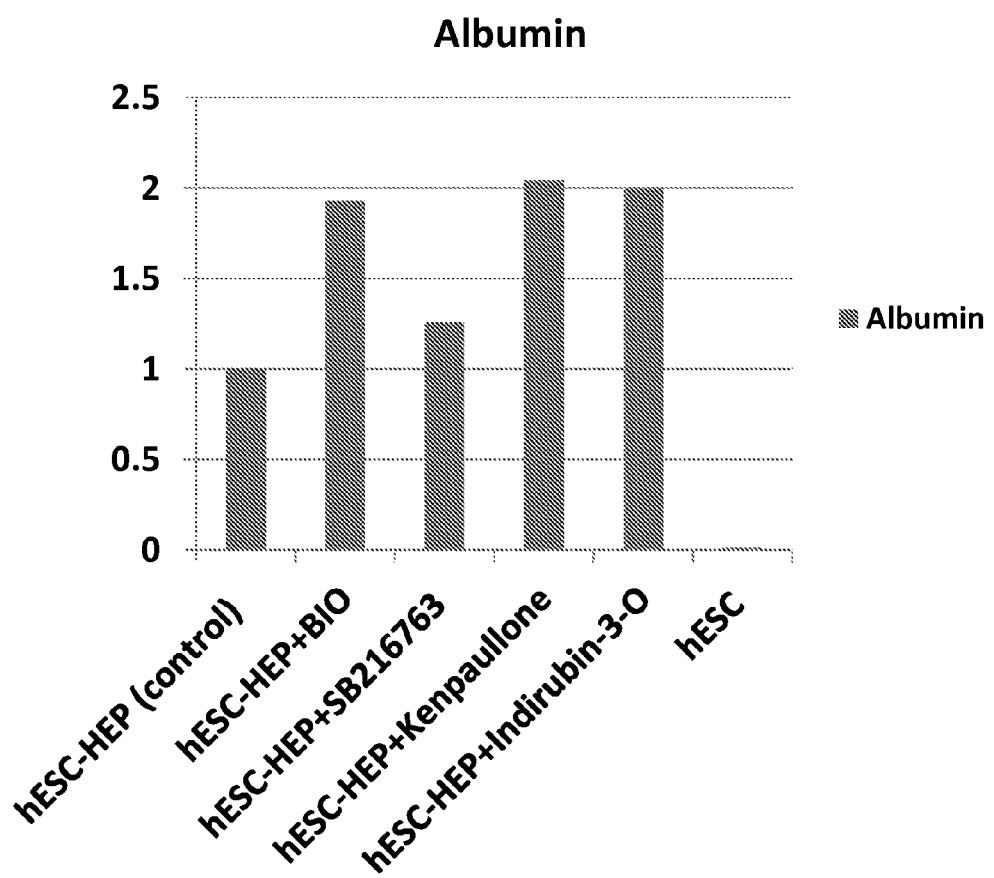
Fig. 12B (Con't)

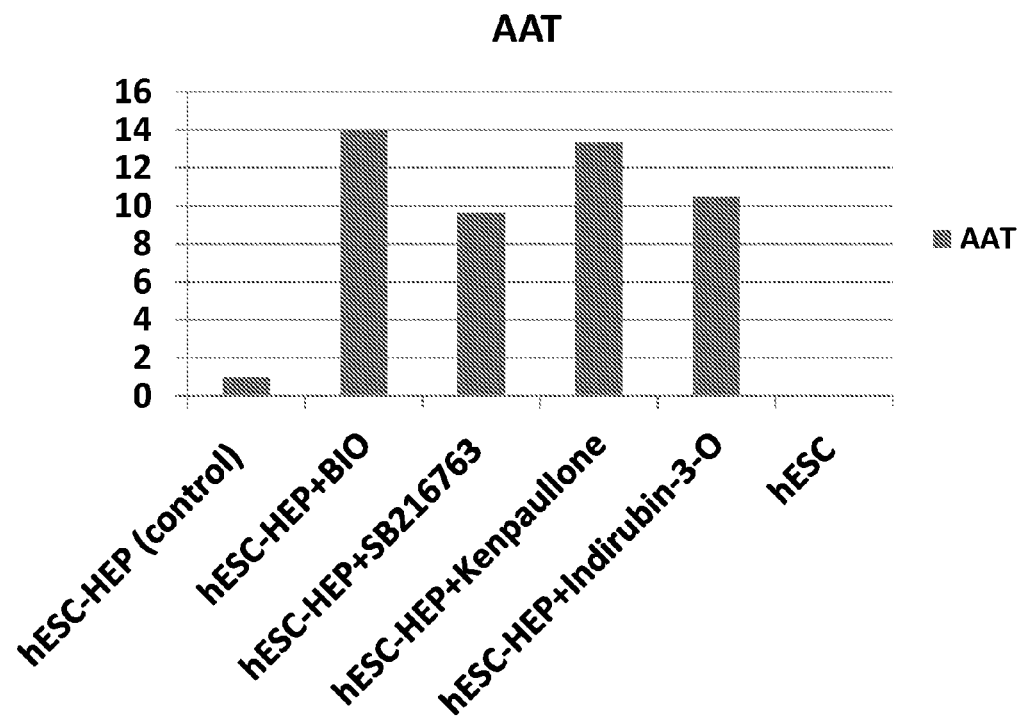
Fig. 12B (Con't)

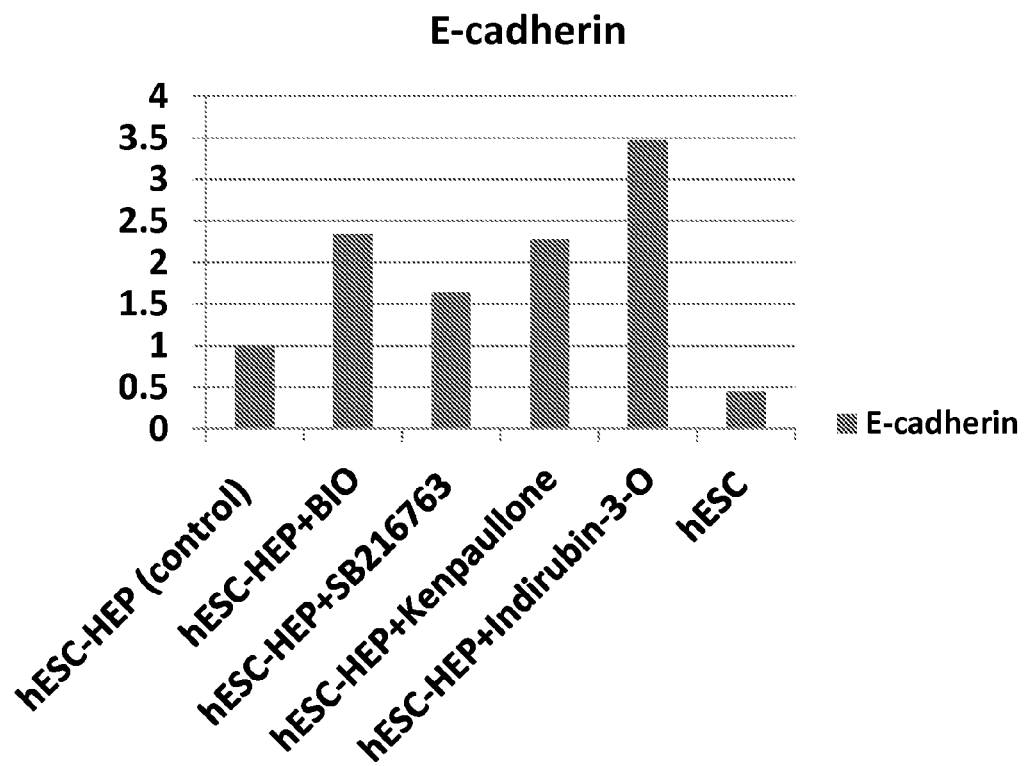
Fig. 12B (Con't)

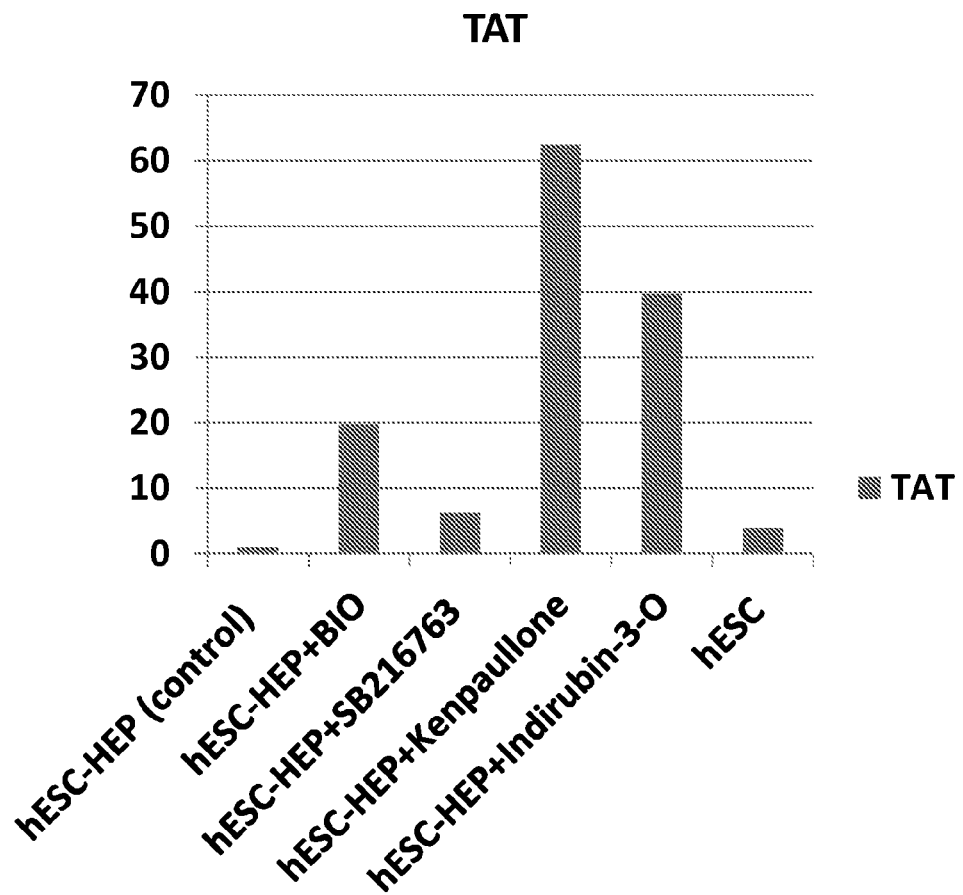
Fig. 12B (Con't)

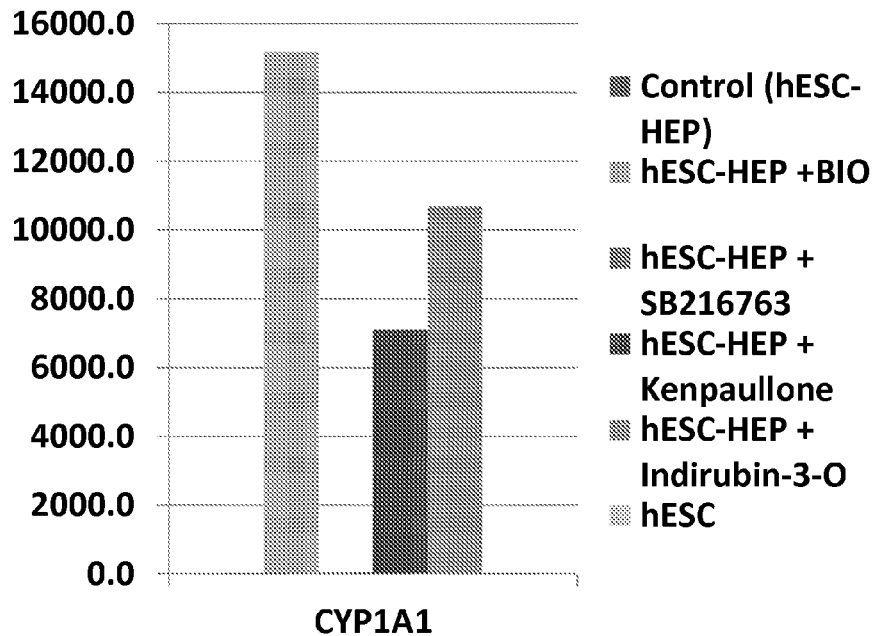
CYP1A2 expression in control cultures was undetected, thus fold changes in expression levels were compared to hESC-HEP+BIO which expression level was set to 1.
Fig. 13A (Con't)

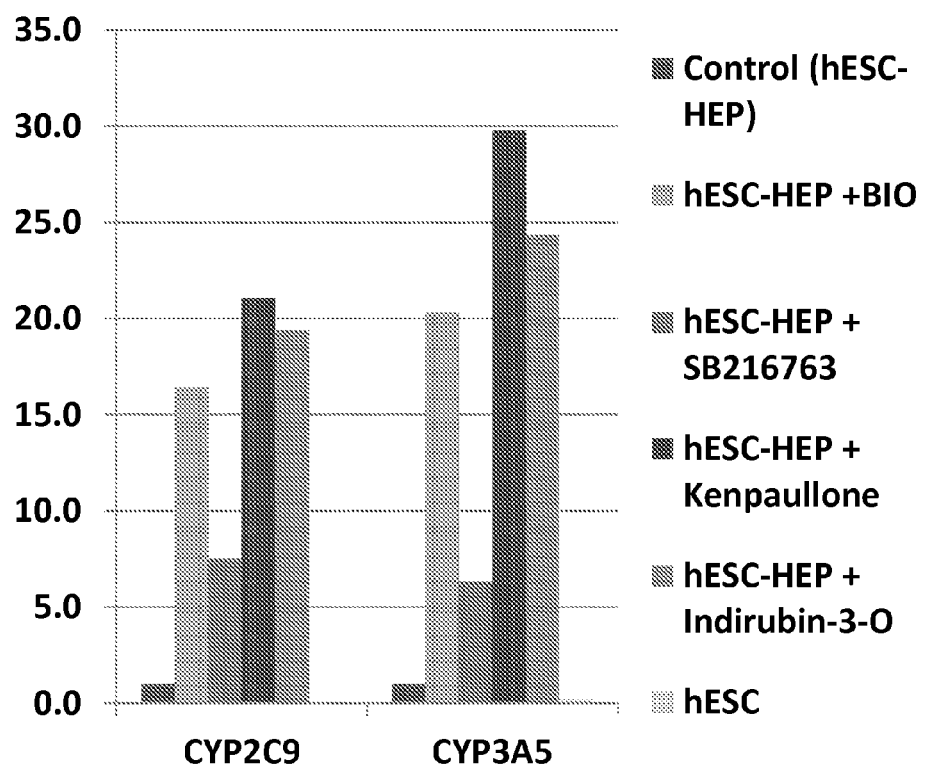
Fig. 13A (Con't)

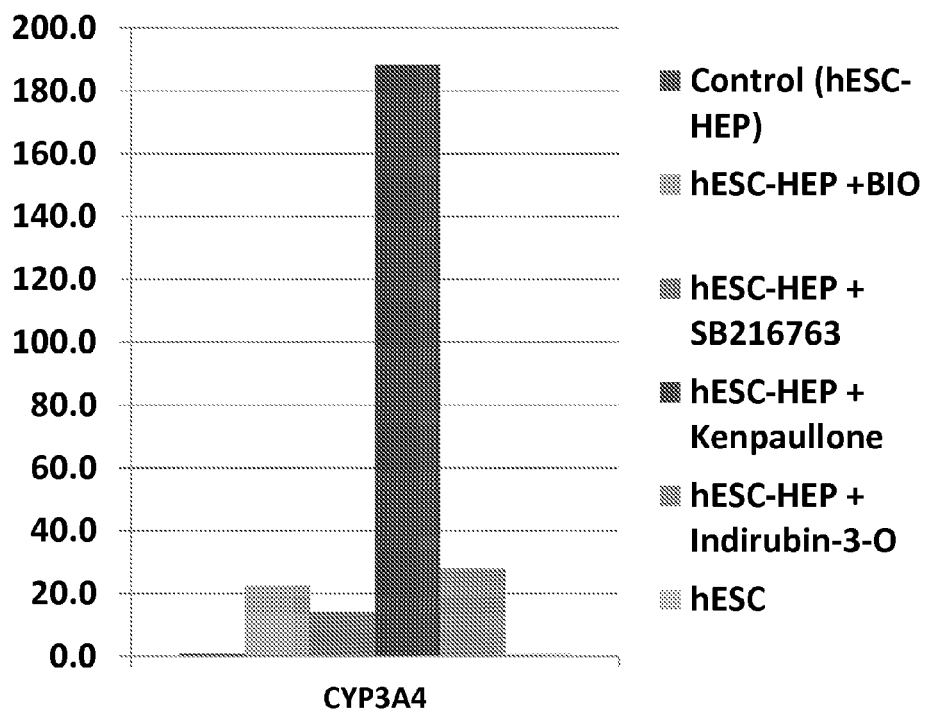
Fig. 13A (Con't)

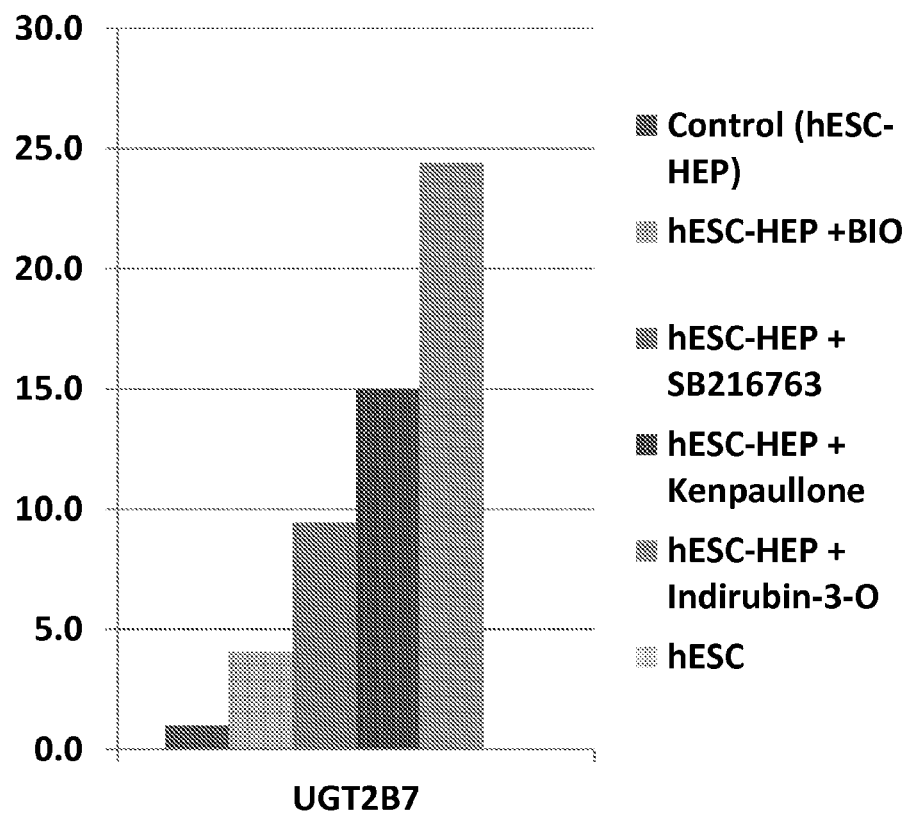
Fig. 13B (Con't)

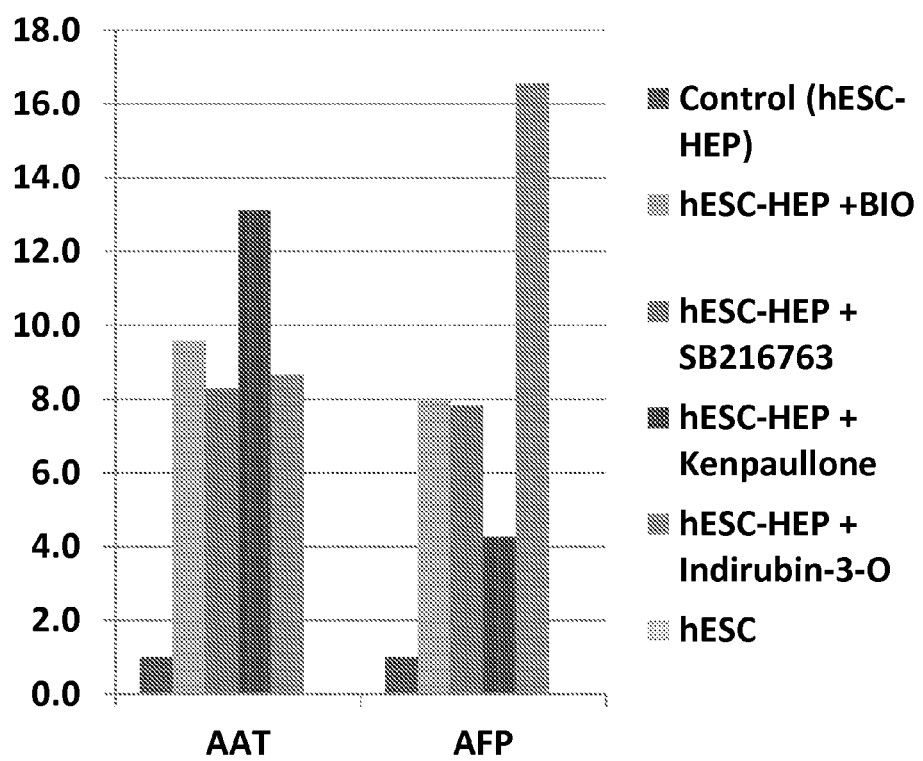
Fig. 13B (Con't)

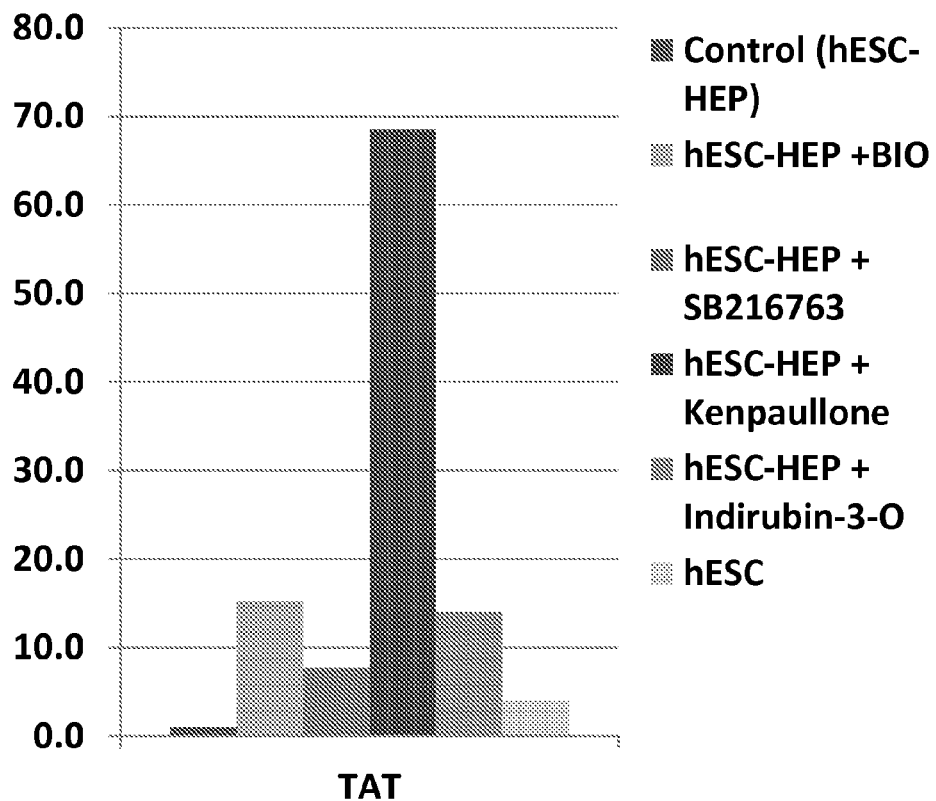
Fig. 13B (Con't)

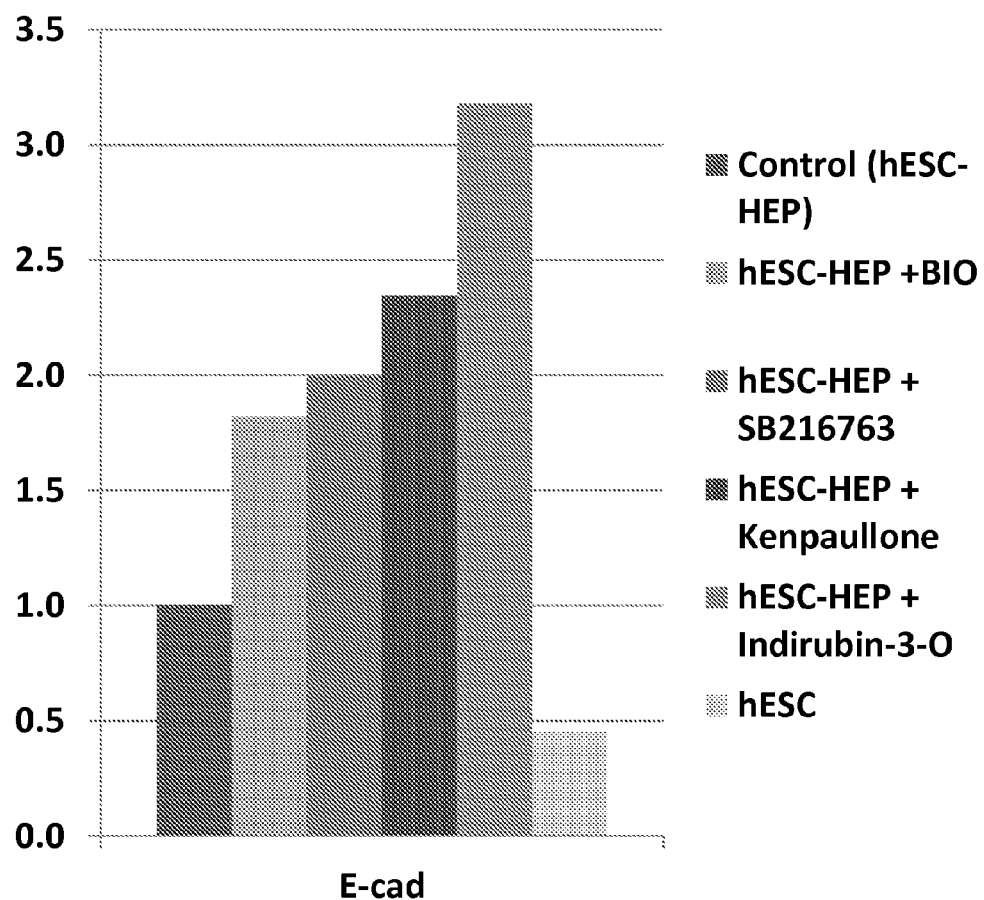
Fig. 13B (Con't)

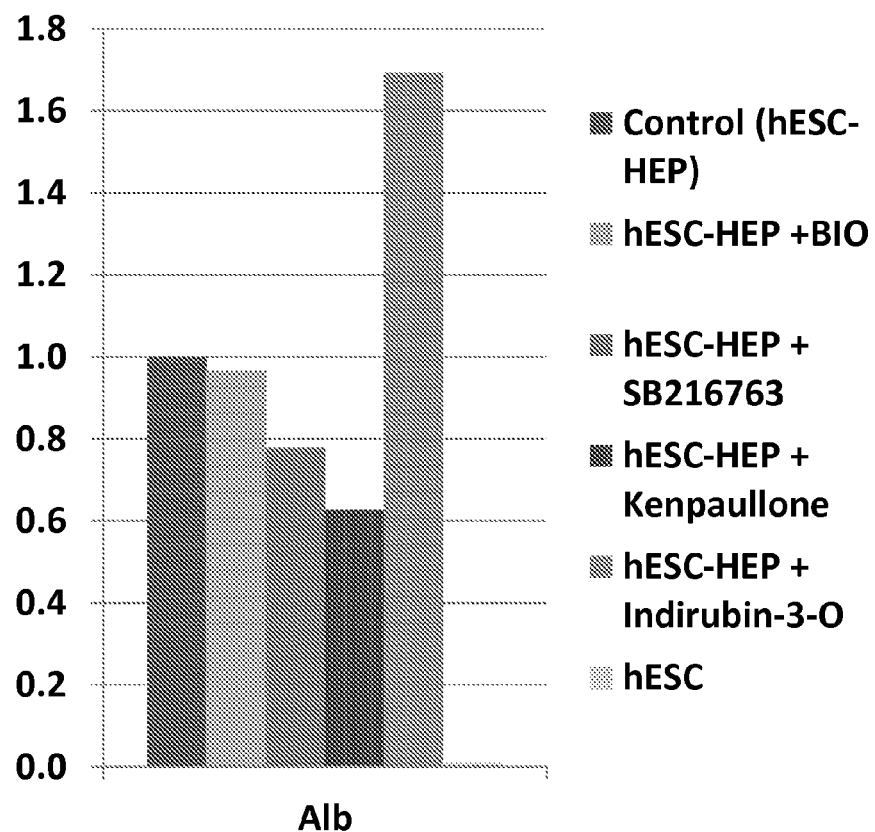
Fig. 13B (Con't)

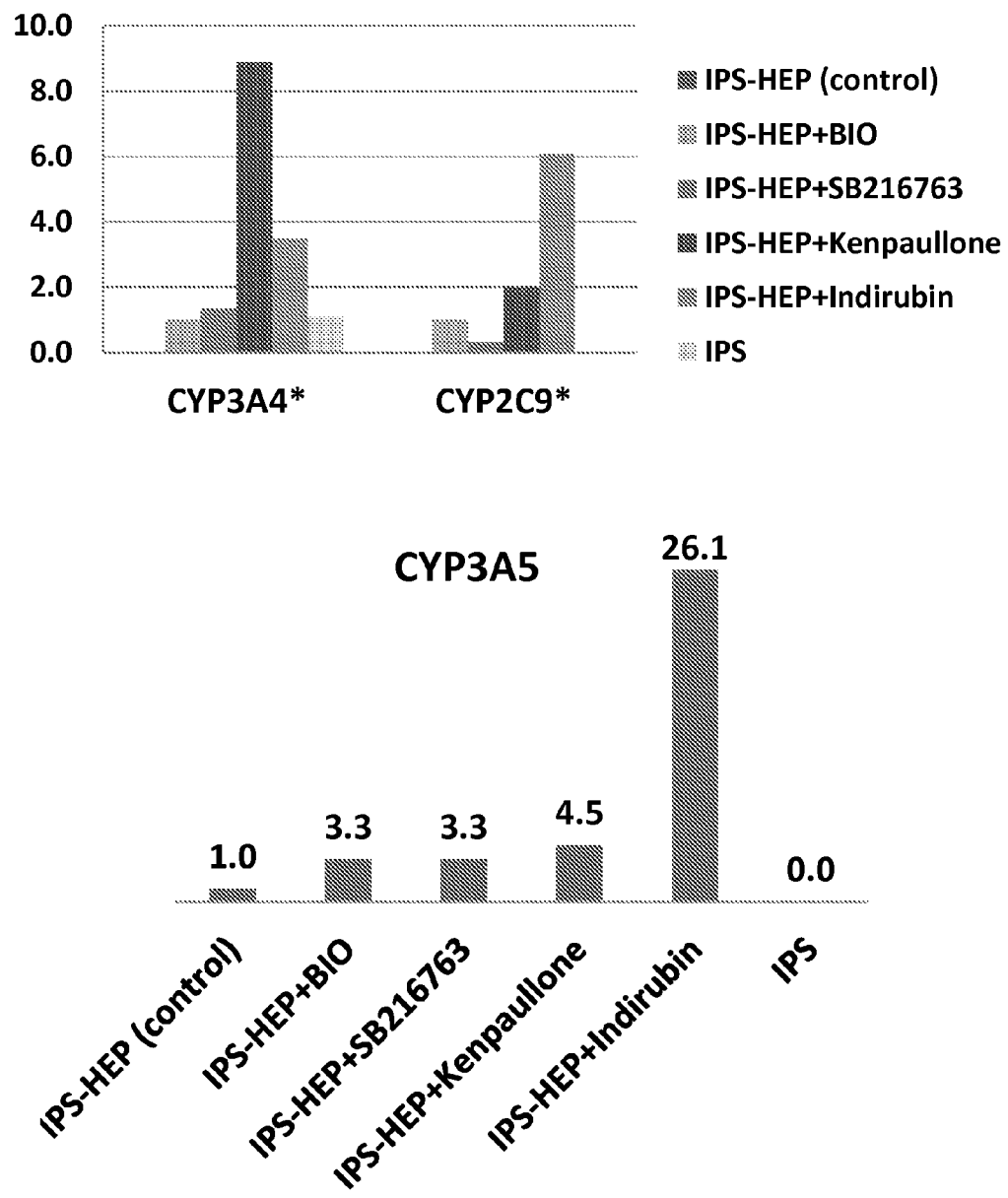
Fig. 14A (Con't)

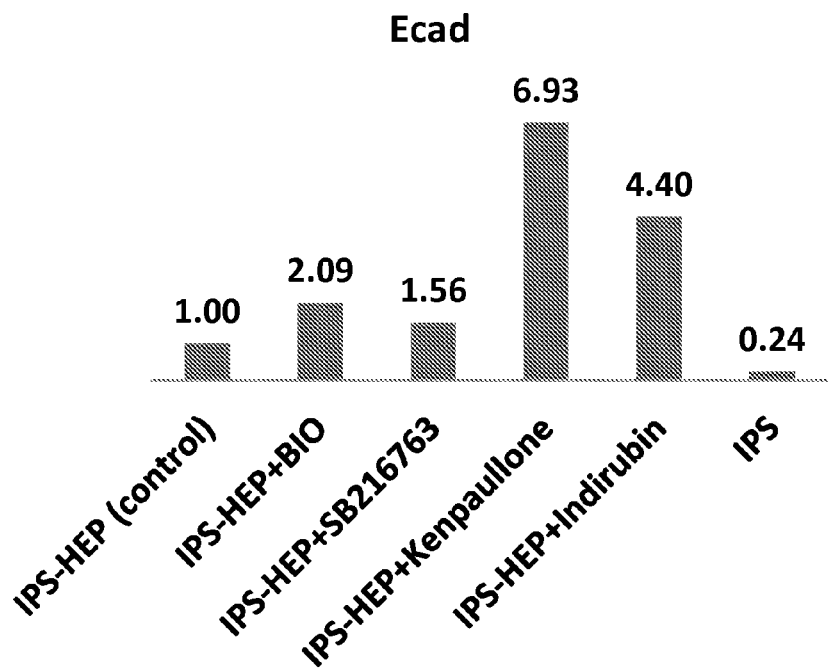
Fig. 14C (Con't)

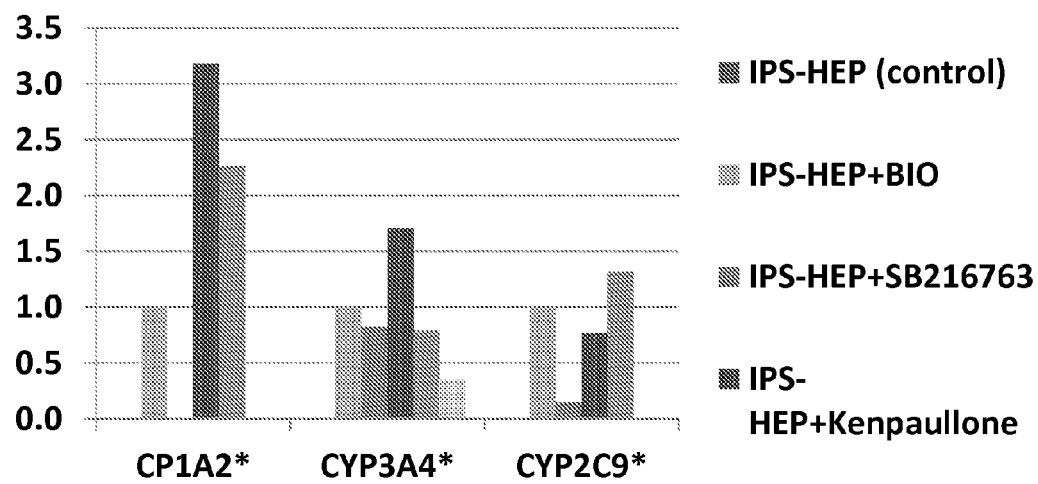
Fig. 15A (Con't)

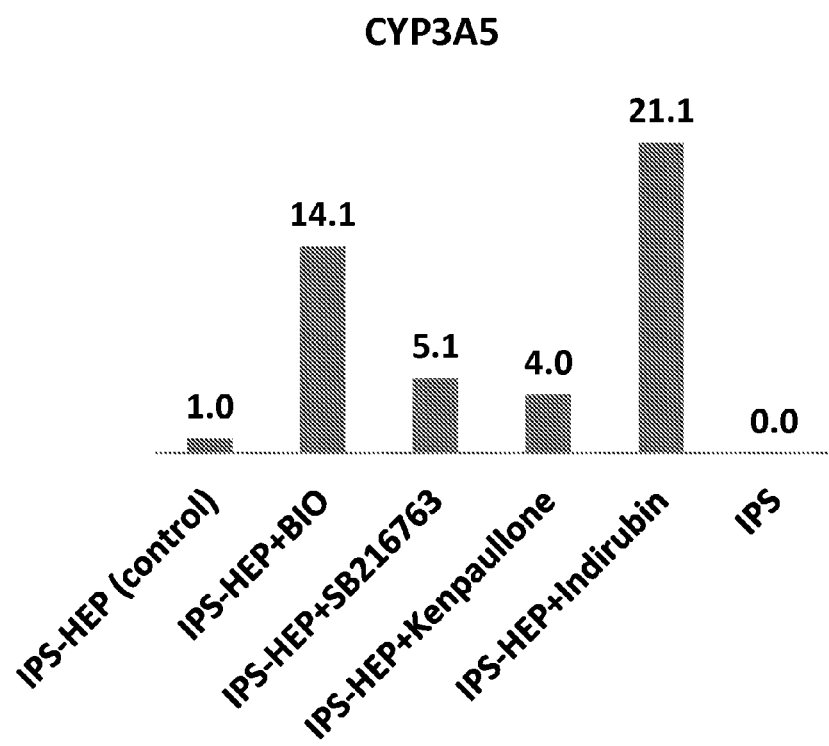
Fig. 15A (Con't)

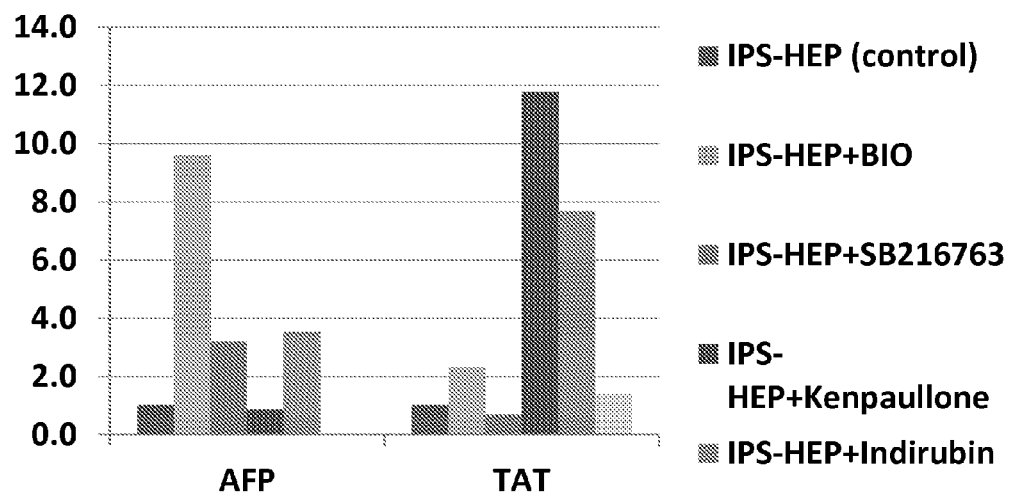
General hepatocyte marker activity in iPS-HEP generated using non-BIO GSK-3 inhibitors at day 3-9 (mid) and 10-23 (late) timepoints
Fig. 15C (Con't)

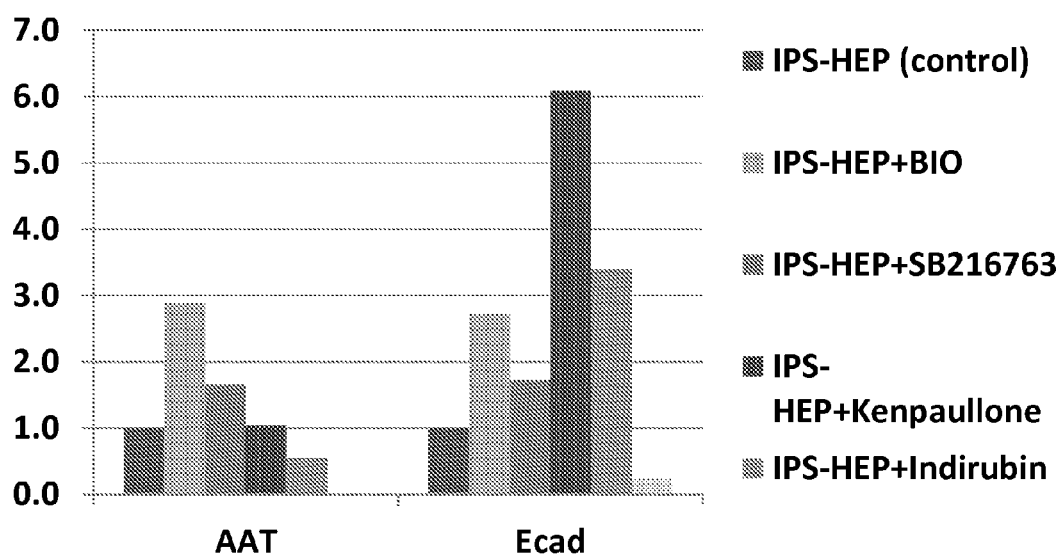
Fig. 15C (Con't)

DIRECTED DIFFERENTIATION AND MATURATION OF PLURIPOTENT CELLS INTO HEPATOCYTE LIKE CELLS BY MODULATION OF WNT-SIGNALLING PATHWAY

CROSS-REFERENCE TO RELATED APPLICATIONS

This application is a U.S. National Stage patent application pursuant to 35 U.S.C. §371 of International Patent Application PCT/EP2001/001411, filed on Mar. 22, 2011, and published as WO 2011/116930 on Sep. 29, 2011, which claims priority to U.S. Provisional Patent Application Ser. No. 61/316,021, filed on Mar. 22, 2010, and Denmark Patent Application PA 2010 00234, filed on Mar. 22, 2010, all of which are incorporated herein by reference in their entireties for all purposes.

TECHNICAL FIELD

The present invention relates to modulation of the wingless integration gene (Wnt)-signalling pathway to achieve directed differentiation and maturation of hepatocytes derived from human pluripotent stem (hPS) cells. Furthermore, the invention refers to the use of a glycogen synthase kinase 3 (GSK3) inhibitor for activation of the Wnt pathway when the cells are at certain developmental stages during the organogenesis. The inventors have, as disclosed herein, found that GSK-3 inhibitors, when added to the growth medium at certain developmental stages leads to more mature and functional features for the hepatocyte like cells as well as more pure and homogenous populations of hepatocyte like cells, compared to currently available state of the art methods.

BACKGROUND OF THE INVENTION

Human pluripotent stem cells (hPS) are expected to revolutionize the accessibility to a variety of human cell types. The possibility to propagate pluripotent human embryonic-derived stem (hES) cells and human induced pluripotent stem (hiPS) cells and subsequently differentiate them into the desired target cell types will provide a stable and virtually unlimited supply of cells for a range of applications in vivo and in vitro.

Liver failure and end-stage liver diseases are responsible for a huge amount of deaths around the world and is a major burden on the health care system. Liver transplantation remains the most successful treatment. However, the efficacy of this procedure is limited and connected to many complications such as infection or rejection. Liver transplantation also suffers from shortage of available donor organs and the treated patients will very often be referred to lifelong immunosuppression therapy. By reducing the need for organs, cell-based treatment will be of great importance to both society and to the individuals suffering from these severe diseases.

Furthermore, the liver is the centre of metabolism and detoxification in the human body, and therefore huge efforts have been undertaken in order to identify a reliable source of functional cell types for in vitro testing. Unfortunately, the complexity and function of the liver is not mirrored by any cell type available today. The availability of primary human liver cells is very limited and the cells are also known to rapidly loose their normal phenotype and functional properties when used for in vitro applications. One often used alternative to primary cells are hepatic cell lines which in turn contain very low levels of (or totally lack) metabolising enzymes and have distributions of other important proteins substantially different from the native hepatocyte in vivo. Thus, many tests are still performed using animal material, even though liver metabolism is known to be species specific and thereby generating difficulties in predicting liver metabolism and toxicity in other species than the one tested.

In pharmaceutical development, adverse liver reactions remain the most prominent side effect. Therefore early prediction of human liver toxicity liabilities is of paramount importance when selecting compounds to enter clinical trials. Efforts to improve capabilities in this area must address both the availability question and development of models, which provide greater coverage for the complex biological processes which coincide to induce adverse liver injury in humans.

Accordingly there is an urgent need for a model system that mimics human liver cells and that is able to predict effects of candidate molecules in the development of new drugs or chemicals. Regarding both availability and physiological relevance, hPS cells may serve as an ideal renewable source of functional human hepatocytes.

During the embryogenesis and the formation of the yolk sac and the placenta, two types of endoderm cells form: the extraembryonic endoderm cells and the definitive endoderm (DE) cells. Extraembryonic endoderm arises at the blastocyst stage and eventually forms two subpopulations: visceral endoderm and parietal endoderm. Extraembryonic endoderm cells share the expression of many genes with definitive endoderm (DE) cells (cells that give rise to the endodermal organs), including the often analyzed transcription factors Sox17 (Kanai-Azuma et al., 2002), FoxA1 and HNF3b/FoxA2 (Belo et al., 1997; Sasaki and Hogan, 1993). However, some markers are expressed in both mesoderm and definitive endoderm, such as CXCR4. Those commonly expressed, markers can be used in combination with Sox17 and FoxA2 to type DE cells. Sox7 is a marker only expressed in extraembryonic endoderm.

The definitive endoderm cells give rise to endodermal organs and thus hepatic cell types. However, early endoderm development is not well understood. Directed studies of cultured mouse embryos (Lawson et al., 1986, 1991; Lawson and Pedersen, 1987) have revealed that DE begins to form at the embryonic days 6-6.5 (E6-6.5) and that by the end of gastrulation (E7.5), some cells only give rise to endodermal derivatives. It is not known whether the initial DE cells are multipotent. Fate mapping studies (Lawson et al., 1991; Tremblay and Zaret, 2005) suggest that the first endoderm cells that migrate through the primitive streak (PS) at E6.5 are fated to become liver, ventral pancreas, lungs and stomach. Co-culture experiments show that the endoderm at this state is not fully committed at the early state of development (Wells and Melton, 2000).

For in vitro purposes, for example D'Amour et al. and Hay et al. have developed protocols for deriving definitive endoderm from hES cells (D'Amour et al., 2005; D'Amour et al., 2006, Hay et al., 2007; Hay et al., 2008) as well as protocols for derivation of hepatic endoderm from hiPS cells (Hay et al. 2010).

The Wnt pathway describes a series of events that occur when Wnt proteins bind to cell-surface receptors of the Frizzled family, causing the receptors to activate other proteins and ultimately resulting in a change in the amount of β-catenin that reaches the nucleus. A membrane-associated Wnt receptor complex will, when activated by Wnt binding, inhibit a second complex of proteins that includes e.g. the proteins GSK3 and axin. This complex normally promotes the proteolytic degradation of the β-catenin intracellular signalling molecule. After this inhibition, a pool of cytoplasmic β-catenin is present intracellularly, and some β-catenin is able to enter the nucleus and interact with transcription factors to promote specific gene expression. The Wnt/β-catenin signalling regulates key physiological events inherent to the liver including development, regeneration and development of cancer, by dictating several biological processes such as proliferation, apoptosis, differentiation, adhesion, zonation and metabolism in various cells of the liver (Nejak-Bowen et al., 2008).

Crosstalk between mesoderm and endoderm is required for liver differentiation. The wnt signalling molecule, Promethues/Wnt2b has been shown to be expressed in the discrete lateral plate mesoderm adjacent to the endoderm that will become hepatic endoderm in the zebra fish. Morpholino antisence knock-down of the wnt-gene will obliterate or reduce the early hepatic differentiation markers of the hepatic endoderm, hHEX and Prox1, indicating a role for wnt signalling in hepatic cell fate specification. In addition inhibition of beta-catenin signalling in the zebrafish embryo strongly reduced the development of hepatic tissue, suggesting a role for the canonocal/beta-catening Wnt signalling in liver cell fate specification. (Ref. Elke Ober et al. Nature 442, 688-691 (10 Aug. 2006) However, observations in xenopus suggests that wnt signalling is crucial for patterning of the definitive endoderm into the anterior and posterior endoderm, where inhibition of wnt signalling leads to the anterior endoderm and hepatic induction while wnt signalling leads to posterior endoderm and intestinal induction. However, just after anterior patterning wnt signalling is important for hepatic induction and delamination of hepatoblasts from the hepatic endoderm. The data from the zebra fish and xenopus are somewhat contradictory and represent the complexity of Wnt-signalling in early hepatic differentiation. Fine tuning and timing of non active and active Wnt signalling seem to be important for early hepatic differentiation.

The use of GSK inhibitors have previously been described for early differentiation towards endoderm. WO08094597 (Dalton) describes a method of producing mesendodermal from primate pluripotent stem cells (pPSC) by contacting the pPSC with an effective amount of GSK inhibitor in a differentiation media.

WO2007050043 (Stanton) describes a method for producing a mesodermal or an endodermal cell from a pluripotent stem cell, comprising a Wnt-signalling pathway in the pluripotent stem cell.

US2006003446 (Keller) describes a way of making a cell population enriched for endoderm cells culturing embryonic stem cells in the absence of serum and in the presence of activin and an inhibitor of Wnt-signalling.

US 20100062527 (Pera et al.) describes in Example 3 culturing of HES2 or 3 cells "for 5 days on MEF feeders with 20% FCS hES medium in organ culture dishes. 20% FCS hES medium was replaced with 3i medium and cells were keeping in culture in this medium for 3 days. Cells were detached as clumps by collagenase and feeder cells were removed by sedimentation in DMEM/F-12 medium. Cells were seeded on Matrigel-coated organ culture dish as 1 to 1 split and culture with 3i medium. After 3 to 5 days in culture hepatoblast-like cells appeared. They were subsequently propagated using 3i of Kubota's medium following enzymatic dissection." The 3i medium contains: Neural basal medium 50%, DMEM/F-12 50%, N2 supplement 1/200 v/v, B27 supplement 1/100 v/v, 100 mM L-glutamine 1/100 v/v, 0.1 M beta-ME 1/1000 v/v, SU5402 (FGFR inhibitor) 2 µM, PD184352 (ERK cascade inhibitor) 0.8 µM, and CHIR99021 (GSK3 inhibitor) 3 µM.

SUMMARY OF THE INVENTION

Present invention describes improved methods by which endodermal cells, notably endodermal cells derived from human pluripotent stem cells (hPS), such as but not limited to hiPS-cells and hES-cells may be differentiated into hepatocyte like cells. Further, the invention relates to new ways of in vitro stimulation of the organogenesis of the liver which is crucial for development of a mature and functional product; the hepatocyte-like cells derived from human pluripotent stem cells.

As disclosed herein, the potential roles of Wnt/β-catenin signalling during the phases of liver development, including competence, hepatic induction, expansion and morphogenesis have been examined and exploited in order to obtain improved hepatocyte like cells from human pluripotent cell types.

The present invention is the first to describe and exploit the specific modulation of Wnt-signalling and the use of a GSK inhibitor for hepatic differentiation using endoderm cells as starting material, i.e. focusing on the direction and modulation of a later stage of the organogenesis compared to previous publications, which are focusing on the use of an inhibitor during differentiation up to the definitive endoderm (DE) stage.

In the present invention an hPS cell derived hepatocyte-like cell population is generated using novel strategies by affecting the Wnt signalling. The cells obtained by the method as described herein by using a GSK3 inhibitor show improved morphology, higher purity and enzymatic activity compared to cells obtained without the use of a GSK-3 inhibitor, and therefore offers improved applicability for drug discovery purposes and regenerative medicine. Furthermore the cells are showing a stable expression of important liver-expressed marker genes such as Albumin, CYP1A2, CYP3A4, UGT2B7, GSTA1 as well as drug transporters for an extended period of time compared to cells obtained without the use of GSK3 inhibitors and are thus highly suitable for drug discovery purposes and regenerative medicine.

We have found that addition of a GSK3 inhibitor helps to generate a pure, synchronized, and metabolically induced culture of hPS derived hepatic like cells both on feeder and in feeder free conditions. In the examples herein feeder free conditions have been demonstrated.

A particular finding is that addition of a GSK inhibitor after initial differentiation of the hPS-cells into mesendodermal progenitors or beyond improves to the further differentiation and quality of the hepatocyte like cells by stimulating an increased cell type homogeneity, catalytic activity and increased expression of hepatic markers.

The present invention disclose how the use of GSK inhibitors and/or modulation of the Wnt signalling pathway at certain time points during the differentiation period help to ensure improved directed differentiation revealed by increased enzyme activity, pronounced gene expression and increased homogeneity of the obtained hepatocyte like cells.

As illustrated herein, a number of different protocols, including different growth media and incubation times are tested and assessed in relation to their applicability to stimulate directed differentiation of undifferentiated pluripotent cells into hepatocyte like cells.

DETAILED DESCRIPTION OF THE INVENTION

Present invention relates to the use of a GSK-3 inhibitor for directed differentiation of endodermal cells into hepatocyte like cells. The starting material in present invention relates to any pluri- or multipotent human cell, developed to any stage at or beyond the endodermal stage, such as hepatic endoderm, including extraembryonic and definitive endoderm cells or hepatic progenitors. Thus, the endodermal cells may comprise definitive endoderm, extraembryonic endoderm or hepatic progenitors.

Further, the GSK-3 inhibitor may be used together with a histone deacetylase (HDAC) inhibitor such as e.g. sodium butyrate (NaB).

The present invention relates to improved differentiation of pluripotent cells (e.g., human induced pluripotent stem cells (hiPS) or human embryonic stem cells, (hESC) cultured under both feeder free conditions and in the presence of feeders, in which the Wnt signalling pathway is influenced by the addition of bioactive compounds to the growth medium after initial differentiation. Initial differentiation may in this context be considered as differentiation from pluripotent stem cells into cells resembling the definitive endoderm, the mesendoderm and/or cells resembling hepatic progenitors.

As exemplified below, the GSK3 inhibitor may be added at predetermined time-points during a differentiation protocol, but more importantly the timing of GSK-3 inhibitor addition is to be determined by the developmental stage of the growing cells, such as after differentiation of the endoderm cells into hepatic progenitors.

Thus, the GSK-3 inhibitor is present after initial differentiation into endodermal cells as extraembryonic or definitive endodermal cells. GSK-3 inhibitors are useful in all aspects of the invention which relate to the differentiation and maturation of hepatocytes from hPS cells and purification in hepatic endoderm differentiation. They are used in concentrations of about 0.001 to about 100 µM or more, about 0.05 to about 75 µM, about 0.1 to about 50 µM, about 0.25 to about 35 µM, about 0.5 to about 25 µM. In the case of the use of BIO, this GSK inhibitor is used in the differentiation medium in an amount ranging from about 0.05 to about 50 µM, about 0.1 to about 10 µM, about 0.5 to about 5 µM, about 1-3 µM. In the case of SB216763 the GSK inhibitor is used in the differentiation medium in an amount ranging from about 30 nM to about 15 µM, about 30 nM to about 1 µM, about 1 µM to about 5 µM, about 5 µM to about 15 µM. In the case of Kenpaullone the GSK inhibitor is used in the differentiation medium in an amount ranging from about 30 nM to about 20 µM, about 30 nM to about 1 µM, about 1 µM to about 5 µM, about 5 µM to about 15 µM. In the case of Indirubin-3'-oxime the GSK inhibitor is used in the differentiation medium in an amount ranging from about 30 nM to about 15 µM, about 30 nM to about 1 µM, about 1 µM to about 4 µM, about 5 µM to about 10 µM.

Thus, in one embodiment, the present invention relates to a method for differentiating definitive endodermal cells to hepatocyte like cells by adding a GSK-3 inhibitor to the growth medium. Depending on the growth media composition and developmental stage of the cells, the growth media may be changed or components added in order to direct differentiation towards a hepatocyte like cell type. Because the developmental stage of the cells is crucial for the timing of GSK-3 inhibitor addition, the chronology in the exemplary protocols may differ. In the tables below are listed examples of protocols in which growth factors and GSK-3 inhibitors are added.

As shown in the Examples herein, it seems advantageous to add a GSK-3 inhibitor at a later stage of differentiation to avoid massive cell death. Moreover the resulting purity of the cell populations (FIG. 8, purity table) also suggest that, at least for BIO, addition at a later stage (day 10+) gives greater final purity.

Using endoderm as starting material, the GSK-3 inhibitor may be added immediately at the start of culturing and throughout the duration of the protocol as illustrated in Scheme A-G. Hence a method for the preparation of hepatocyte like stem cells according to present invention may resemble any of the schemes as illustrated in scheme A-G below.

Scheme A

| Starting material | Time, day | Liquid medium comprising: |
|---|---|---|
| DE-cells | 0 to 2-8 | Medium A1 + GSK-3 inhibitor, e.g. BIO |
|  | 2-8 to 10-20 | Medium A2 + GSK-3 inhibitor, e.g. BIO |
|  | 10-20 to 45 | Medium A3 + GSK-3 inhibitor, e.g. BIO |

Scheme B

| Starting material | Time, day | Liquid medium comprising: |
|---|---|---|
| DE-cells | 0 to 2-8 | Medium B1 + GSK-3 inhibitor, e.g. BIO |
|  | 2-8 to 10-20 | Medium B2 + GSK-3 inhibitor, e.g. BIO |
|  | 10-20 to 45 | Medium B3 |

Scheme C

| Starting material | Time, day | Liquid medium comprising: |
|---|---|---|
| DE-cells | 0 to 2-8 | Medium C1 |
|  | 2-8 to 10-20 | Medium C2 + GSK-3 inhibitor, e.g. BIO |
|  | 10-20 to 45 | Medium C3 + GSK-3 inhibitor, e.g. BIO |

Scheme D

| Starting material | Time, day | Liquid medium comprising: |
|---|---|---|
| DE-cells | 0 to 2-8 | Medium D1 + GSK-3 inhibitor, e.g. BIO |
|  | 2-8 to 10-20 | Medium D2 |
|  | 10-20 to 45 | Medium D3 + GSK-3 inhibitor, e.g. BIO |

The growth media as listed in scheme A-D may further comprise the following components:

| Growth media | Comprise | Examples of further components that may be added |
|---|---|---|
| A1, B1, C1, D1 | Activin A | RPMI1640 + PEST + glutamax<br>B27<br>Activin<br>NaB |
| A2, B2, C2, D2 |  | Vitrohes<br>1% DMSO |

-continued

| Growth media | Comprise | Examples of further components that may be added |
|---|---|---|
| A3, B3, C3, D3 | HGF dexamethasone | WME + SQ (-GA1000) + glutamax + PEST<br>OsM<br>Dexamethasone<br>bFGF<br>HGF<br>DMSO<br>Nicotinamide<br>ITS<br>Glucagon |

Additionally as specified in scheme E-G, when using DE-cells as starting material, other media and culturing intervals may be used to facilitate directed differentiation to hepatocyte like cells.

Scheme E

| Starting material | Time, day | Liquid medium comprising: |
|---|---|---|
| DE-cells | 0 to 3-14 | Medium E1 |
|  | 3-14 to 45 | Medium E2 + GSK-3 inhibitor, e.g. BIO |

Scheme F

| Starting material | Time, day | Liquid medium comprising: |
|---|---|---|
| DE-cells | 0 to 1-5 | Medium F1 |
|  | 1-5 to 6-14 | Medium F2 |
|  | 6-14 to 45 | Medium F3 + GSK-3 inhibitor, e.g. BIO |

Scheme G

| Starting material | Time, day | Liquid medium comprising: |
|---|---|---|
| DE-cells | 0 to 1-5 | Medium G1 |
|  | 1-5 to 6-14 | Medium G2 + GSK-3 inhibitor, e.g. BIO |
|  | 6-14 to 45 | Medium G3 + GSK-3 inhibitor, e.g. BIO |

The growth media as listed in scheme E-G may further comprise the following components

| Growth media | Comprise | Examples of further components that may be added |
|---|---|---|
| E1, F1, G1 | aFGF<br>bFGF<br>BMP2<br>BMP4<br>Dexamethasone<br>HGF | WME + SQ (-GA1000) + glutamax + PEST<br>OsM<br>DMSO<br>Nicotinamide<br>ITS<br>Glucagon<br>FBS |
| F2, G2<br>E2, F3, G3 | DMSO<br>HGF<br>Dexamethasone | Vitrohes<br>WME + SQ (-GA1000) + glutamax + PEST<br>OsM<br>HGF<br>DMSO<br>Glucagon |

When using hepatic progenitors as starting material, schemes H-J as specified below, may be used to direct differentiation into hepatocyte like cells. As shown in table H-J, a method for the preparation of hepatocyte like stem cells according to present invention may resemble any of the schemes as illustrated in scheme H-J below Scheme H

| Starting material | Time, day | Liquid medium comprising: |
|---|---|---|
| Hepatic progenitors | 0 to 10-20 | Medium H1 + GSK-3 inhibitor, e.g. BIO |
|  | 10-20 to 45 | Medium H2 + GSK-3 inhibitor, e.g. BIO |

Scheme I

| Starting material | Time, day | Liquid medium comprising: |
|---|---|---|
| Hepatic progenitors | 0 to 10-20 | Medium I1 + GSK-3 inhibitor, e.g. BIO |
|  | 10-20 to 45 | Medium I2 |

Scheme J

| Starting material | Time, day | Liquid medium comprising: |
|---|---|---|
| Hepatic progenitors | 0 to 10-20 | Medium J1 |
|  | 10-20 to 45 | Medium J2 + GSK-3 inhibitor, e.g. BIO |

The growth media as listed in scheme H-J may further comprise the following components

| Growth media | comprise | Examples of further components that may be added |
|---|---|---|
| H1, I1, J1<br>H2, I2, J2 | DMSO<br>HGF<br>Dexamethasone | Vitrohes<br>WME + SQ (-GA1000) + glutamax + PEST<br>OsM<br>HGF<br>DMSO<br>Glucagon |

As used in schemes A-J and corresponding growth media, the components may be added in the following concentrations:

Activin A: 5-250 ng/ml, such as e.g. 50-200 ng/ml such as 75-150 ng/ml preferably 100 ng/ml GSK-3 inhibitor: 0.1-10 µM such as e.g., 1-5 µM preferably 1.4 µM and 3.5 µM for late stage media (A3, B3, C3, D3 etc) and early stage media (A1, A2, B1, B2, C1, C2, D1, D2 etc) respectively. Meaning a 2-3 times higher concentration added for the use in the early stage media, than in late stage media.

Dexamethasone: 0.01-5 µM such as eg. 0.05-2 µM preferably 0.1 µM

HGF (human growth factor): 1-50 ng/ml such as 5-30 ng/ml preferably 20 ng/ml aFGF (acidic fibroblast growth factor): 10-250 ng/ml such as eg. 50-200 ng/ml preferably 100 ng/ml bFGF. (basic fibroblast growth factor): 1-25 ng/ml such as eg. 5-10 ng/ml, preferably 5 ng/ml BMP2 (bone morphogenic protein 2) 10-250 ng/ml, such as eg 25-100 ng/ml preferably 50 ng/ml BMP4 (bone morphogenic protein 4): 25-500 ng/ml such as eg. 50-250 ng/ml preferably 200 ng/ml Glucagon; 0.3-20 ng/ml, such as eg. 1-10 ng/ml, such as eg. 2-5 ng/ml preferably 3 ng/ml DMSO (dimethyl sulfoxide): 0.05-5% such as eg.0.1-2% preferably 0.5%

OsM (Ocostatin M): 1-25 ng/ml, such as eg. 5-15 ng/ml preferably 10 ng/ml

PEST: 0.01-5%, preferably 0.1%

Nicotinamide: 1-25 mM, such as eg. 5-15 mM, preferably 10 mM

ITS (Insulin-Transferrin-Selenium-G Supplement (100×)): 1-25 µl/ml, such as eg. 5-15 µl/ml preferably 10 µl/ml FBS (fetal bovine serum): 0.1-10%, such as 0.5-5%, such as eg.1-4, preferably 2%

B27 (B-27 Serum-Free Supplement (50×), liquid (Invitrogen)): preferably a dilution to 1× NaB (Sodium Butyrate): 0.1-10 mM, such as 0.5-5 mM, preferably 1 mM RPMI1640 ([Sigma-Aldrich] bicarbonate-buffered, defined cell culture medium, must be supplemented with glutamine 0.3 g/L, L-L-Glutamine (glutamax)

VitroHES ([Vitrolife]) defined, balanced cell culture medium for the support of human embryonic stem cell culture. Must be supplemented with bFGF at preferably at a concentration of between 1 ng/ml-100 ng/ml WME+SQ medium—Williams Medium E supplemented with SQ medium kit (OsM, Insulin, HGF, EGF)

Specific examples are also given in the Examples herein.

Improved differentiation in present invention is intended to include better maturation, improved cell type homogeneity, increased enzymatic activity or substrate conversion, assessed by comparing the cells obtained by a method using a GSK-3 inhibitor as disclosed herein, to cells obtained without the use of a GSK-3 inhibitor. Further, improved differentiation may be improved expression of genes associated with a hepatic cell fate assessed by comparing the cells obtained by a method using a GSK-3 inhibitor as disclosed herein, to cells obtained without the use of a GSK-3 inhibitor. However, improved differentiation as disclosed herein also intended to include improved viability, ability to engraft and better applicability for example drug screening and drug development purposes.

Manipulation of the Wnt-singalling pathway by the use of a GSK-3 inhibitor has shown to improve the gene-expression profiles of hepatocyte like cells.

hESC-HEPs may be derived from a xeno-free hPS cell line which was established under animal-free conditions. Moreover, hESC-HEPs may be derived from such an hPS cell line under xeno-free (animal free) conditions, giving rise to a truly xeno-free cell composition. Such a cell line would be better suited to therapeutic or regenerative medicine applications and could be distinguished from a non-xeno-free hESC-HEP line by the presence in non-xeno-free lines of the non-human sialic acid Neu5Gc or other non-human markers (Martin M J et al 2005).

The products obtained according to present invention comprise cells obtained by the method or schemes as disclosed herein, in vitro derived hepatocyte-like cells growing in the presence of a GSK-3 inhibitor (e.g. BIO) and/or a HDAC inhibitor (e.g. NaB) or compositions comprising in vitro derived hepatocyte-like cells and a GSK-3 inhibitor (e.g. BIO) and/or a HDAC inhibitor (e.g. NaB).

Further the compositions as claimed in present invention relates to compositions of in vitro derived human cells comprising hepatocyte like cells wherein at least 70% such as e.g. 75%, 80%, 90% or 95% of the cells are hepatocyte like cells The compositions according to present invention also relates to compositions wherein the hepatocyte like cells show cytochrome P450 activities exceeding a fold change of at least 10, such as e.g. 13, such as e.g. 18 in cytochrome P450 activity, when compared to cultures where a GSK inhibitor is not used. The cytochrome P450 activity may be measured by cytochrome P450 1A.

Compositions according to present invention may further show elevated expression of hepatocyte-associated genes such as e.g. CYP1A1, CYP1A2, CYP3A4, CYP2C9, CYP7A1, MRP2. They may also show increased metabolic activity, as evidenced by increased activity of UGT enzymes (UDP-glucuronyltransferases) such as UGT1A1, UGT1A6, UGT1A9, UGT2B7). Improved metabolic activity may also be shown by ability of hepatocyte-like cell compositions to metabolise drugs such as paracetamol and Diclofenac.

The cells obtained according to the methods and principles as laid out in present invention may be used to a multitude of purposes comprising drug discovery processes, toxicity test, for studying drug transporters, drug metabolizing enzyme, as in vitro models for studying hepatogenesis, such as, e.g., early hepatogenesis. for studying human hepatoregenerative disorders, for in vitro hepatotoxicity testing. Further the hepatocyte-like cells obtained according to the directions given in present invention may be used for therapeutic purposes comprising: in a medicament, for the manufacture of a medicinal product for the prevention and/or treatment of pathologies and/or diseases caused by tissue degeneration, such as, e.g., the degeneration of liver tissue, for the manufacture of a medicinal product for the treatment of liver disorders or for the manufacture of a medicinal product for the prevention and/or treatment of liver disorders selected from the group consisting of auto immune disorders including primary biliary cirrhosis; metabolic disorders including dyslipidemia; liver disorders caused by e.g. alcohol abuse; diseases caused by viruses such as, e.g., hepatitis B, hepatitis C, and hepatitis A; liver necrosis caused by acute toxic reactions to e. g. pharmaceutical drugs; and tumour removal in patients suffering from e. g. hepatocellular carcinoma. Alternatively, the cells obtained according to the directions provided in present invention may be used for the manufacture of a medicinal product for the treatment and/or prevention of metabolic pathologies and/or diseases, for obtaining metabolically improved hepatocyte-like cells, for studying maturation towards hepatocyte-like cells or for screening a compound for its ability to modulate hepatocellular function, comprising exposing in vitro derived hepatocyte-like cells obtained according to the directions provided herein to the compound, determining any phenotypic or metabolic changes in the cells that result from contact with the compound, and correlating the change with an ability to modulate hepatocellular function.

The present invention also relates to a method for the preparation of hepatocyte-like cells and to compositions containing such cells. Details appear from the appended claims. The particulars and details described above apply mutatis mutandis to all aspects of the invention.

DEFINITIONS

As used herein, "human pluripotent stem cells" (hPS) refers to cells that may be derived from any source and that are capable, under appropriate conditions, of producing human progeny of different cell types that are derivatives of all of the 3 germinal layers (endoderm, mesoderm, and ectoderm). hPS cells may have the ability to form a teratoma in 8-12 week old SCID mice and/or the ability to form identifiable cells of all three germ layers in tissue culture. Included in the definition of human pluripotent stem cells are embryonic cells of various types including human embryonic stem (hES) cells, (see, e.g., Thomson et al. (1998), Heins et. al. (2004), as well as induced pluripotent stem cells (see, e.g. Yu et al., (2007) Science 318:5858); Takahashi et al., (2007) Cell 131(5):861). The various methods and other embodiments described herein may require or utilise hPS cells from a variety of sources. For example, hPS cells suitable for use may be obtained from developing embryos. Additionally or alternatively, suitable hPS cells may be obtained from established cell lines and/or human induced pluripotent stem (hiPS) cells.

As used herein "hiPS cells" refers to human induced pluripotent stem cells.

As used herein "definitive endoderm (DE)" and definitive endoderm cells (DE-cells) refers to cells exhibiting such as but not limited to protein or gene expression and or/or morphology typical to cells of the definitive endoderm or a composition comprising a significant number of cells resembling the cells of the definitive endoderm.

As used herein, "hepatic progenitors" or "hepatic progenitor cells" refers to refers to cells exhibiting markers such as but not limited to protein or gene expression and/or morphology typical to cells of the definitive endoderm or a composition comprising a significant number of cells resembling the cells of the hepatic progenitors.

As used herein, "hepatocyte-like cells (HCLC)" is intended to mean a cell type which is expressing mature hepatic markers such as Albumin, CYP3A4, UGT2B7, OATP-2.

As used herein, "hESC-HEP" is intended to mean a cell type derived from human embryonic stem cells which is expressing mature hepatic markers such as Albumin, CYP3A4, UGT2B7, OATP-2, ADH1A, UGT1A6, CYP2C9, CYP2C19 and CYP2D6.

As used herein, "Wnt-signalling" refers to the pathways included in the Wnt signalling as reviewed in, but not limited to, Lade, A G, and Monga, S P, Dev.Dyn. 240:486-500 (2011).

As used herein HDAC inhibitors refers to Histone deacetylase inhibitors.

As used herein, "GSK inhibitor" refers to a compound which inhibits GSK (especially GSK3, including GSK3alpha or GSK3beta). Examples of preferred GSK inhibitors for use in the present invention include one or more of the following:
BIO (2'Z,3'E)-6-Bromoindirubin-3'-oxime (GSK3 Inhibitor IX);
BIO-Acetoxime (2'Z,3'E)-6-Bromoindirubin-3'-acetoxime (GSK3 Inhibitor X);
(5-Methyl-1H-pyrazol-3-yl)-(2-phenylquinazolin-4-yl) amine (GSK3-Inhibitor XIII); Pyridocarbazole-cyclopenadienylruthenium complex (GSK3 Inhibitor XV);
TDZD-8 4-Benzyl-2-methyl-1,2,4-thiadiazolidine-3,5-dione (GSK3beta Inhibitor I);
2-Thio(3-iodobenzyl)-5-(1-pyridyl)[1,3,4]-oxadiazole (GSK3beta Inhibitor II);
OTDZT 2,4-Dibenzyl-5-oxothiadiazolidine-3-thione (GSK3beta Inhibitor III);
alpha-4-Dibromoacetophenone (GSK3beta Inhibitor VII);
AR-AO 14418 N-(4-Methoxybenzyl)-N'-(5-nitro-1,3-thiazol-2-yl)urea (GSK-3beta Inhibitor VIII);
3-(1-(3-Hydroxypropyl)-1H-pyrrolo[2,3-b]pyridin-3-yl]-4-pyrazin-2-yl-pyrrole-2,5-dione (GSK-3beta Inhibitor XI);
TWSI 19 pyrrolopyrimidine compound (GSK3beta Inhibitor XII);
L803 H-KEAPPAPPQSpP-NH2 (SEQ ID NO:1) or its Myristoylated form (GSK3beta Inhibitor XIII); and 2-Chloro-1-(4,5-dibromo-thiophen-2-yl)-ethanone (GSK3beta Inhibitor VI);
Aminopyrimidine CHIR99021.
Kenpaullone (9-Bromo-7,12-dihydro-indolo[3,2-d][1]benzazepin-6(5H)-one, SB216763 3-(2,4-Dichlorophenyl)-4-(1-methyl-1H-indol-3-yl)-1H-pyrrole-2,5-dione and Indirubin-3'-monoxime Furthermore small molecules can be used to direct Wnt-signalling. As well GSK3β blockers for Wnt-signalling induction can be used for modulation of Wnt-signalling to achieve directed differentiation and maturation. The Wnt-signalling pathway can be induced at a later stage after initiation or before induction occurs.

As used herein "CYP" is intended to mean Cytochrome P, and more specifically Cytochrome P 450, the major phase I metabolizing enzyme of the liver constituting of many different isoenzymes, such as CYP1A1, CYP1A2, CYP1B1, CYP2A6/2A7/2A13, CYP2B6, CYP2C8, CYP2C9, CYP2C19, CYP2D6, CYP2E1, CYP3A4, CYP3A5, CYP3A7 and CYP7A1.

As used herein, the term "GST" is intended to mean glutathione transferase, and examples of subtypes thereof are GST A1-1, GST M1-1, and GST P1-1.

As used herein the term "UGT" is intended to mean uridine diphosphoglucuronosyltransferase, which is a group of liver enzymes catalyzing glucuronidation activities.

By the term "functional drug metabolising enzymes" is intended to mean functional enzymes belonging to the phase I and phase II enzymes that perform chemical modifications of xenobiotics and drugs, so called drug or xenobiotic metabolism.

As used herein, the term "functional activity" means effective measurable hepatic cell function, such as a measurable transportation of drugs for drug transporters and a measurable metabolism of enzymes for the Cytochrome P450s (CYPs), commonly detected in primary human hepatocytes.

As used herein, the term "extraembryonic endoderm (ExE)" is intended to mean the differentiated endodermal cells that, as to the opposite of the definitive endoderm, will constitute the compartments outside the embryo in the human development, such as the yolk sac.

As used herein, the term "AAT" is intended to mean the liver marker alpha-anti-trypsin.

As used herein, the term "AFP" is intended to mean the liver marker alpha-fetoprotein. As used herein, the term "BSEP" is intended to mean the bile transporter bile salt export pump.

As used herein, the term "CK" is intended to mean the liver marker cytokeratin (used interchangeably) with different subtypes such as Cytokeratin 18 (CK18/KRT18), Cytokeratin 19 (CK19/KRT19), Cytokeratin 8 (CK8) and Cytokeratin 7 (CK7).

As used herein, the term "FGF" means fibroblast growth factor, preferably of human and/or recombinant origin, and subtypes belonging thereto are e.g. "bFGF" (means basic fibroblast growth factor, sometimes also referred to as FGF2) and FGF4. "aFGF" means acidic fibroblast growth factor (sometimes also referred to as FGF1).

As used herein, the term "BMP" means Bone Morphogenic Protein, preferably of human and/or recombinant origin, and subtypes belonging thereto are e.g. BMP4 and BMP2.

As used herein, the term "HGF" means Hepatocyte Growth Factor, preferably of human and/or recombinant origin.

As used herein the "HNF3beta", or "HNF3b", used interchangeably are intended to mean hepatocyte nuclear factor 3, a transcription factor regulating gene expression in endodermal derived tissue, e.g. the liver, pancreatic islets, and adipocytes. HNF3beta may sometimes also be referred to as HNF3b or Fox2A the latter name originating from the transcription factor being a member of Forkhead box transcription factors family.

As used herein the term "OCT-1" is intended to mean organic cation transporter 1. OCT-1 is a major hepatic transporter that mediates the uptake of many organic cations from the blood into the liver where the compounds may be metabolized or secreted into the bile.

As used herein the term "MDR" is intended to mean multidrug resistance transporter. MDR 1 and 3 are members of the ATP-binding cassette (ABC) family of transporters and both are drug efflux transporters. MDR 1 is important in regulating the traffic of drugs, peptides and xenobiotics into the body and in protecting the body against xenobiotic insults and drug toxicity, while MDR 3 is essential for phospholipid secretion into bile.

As used herein the term "Activin" is intended to mean a TGF-beta family member that exhibits a wide range of biological activities including regulation of cellular proliferation and differentiation such as "Activin A" or "Activin B". Activin belongs to the common TGF-beta superfamiliy of ligands.

As used herein the term "xeno-free" is intended to mean complete circumvention of direct or in-direct exposure to non-human animal components.

As used herein, the term "hepatocellular toxicity" indicates cellular responses such as necrotic toxicity, apoptosis, mitochondrial toxicity, phospholipidosis, steatosis and bile acid transport.

2*i*. shows the control culture conditions without GSK-3 inhibitor added.

2*ii*. shows one aspect of the invention, in which the GSK-3 inhibitor is added to the growth medium after initial differentiation, hence when the cells are showing characteristics similar to type of the endodermal or more specifically definitive endoderm lineage. In this aspect, the GSK-3 inhibitor is removed when the cells are showing characteristic similar to hepatic progenitor cells.

2*iii*. shows one aspect of the invention, in which the GSK-3 inhibitor is added to the growth medium after differentiation into hepatocyte progenitors. Thus in this aspect of the invention, the GSK-3 inhibitor is added when the cells are showing characteristic similar to hepatic progenitor cells.

2*iv*. shows one aspect of the invention, in which the GSK-3 inhibitor is added to the growth medium after initial differentiation when the cells are showing characteristics similar to type of the endodermal or more specifically definitive endoderm lineage. In one further aspect according to iv. the type and concentration of the GSK-3 inhibitor may be changed during the culturing period.

Figure 3:
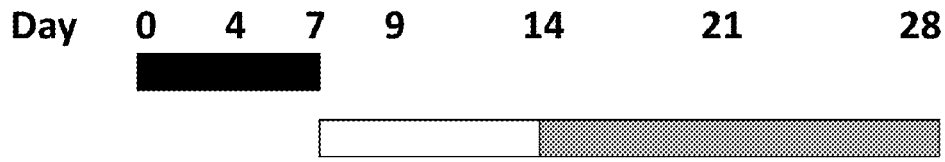
Figure 3:
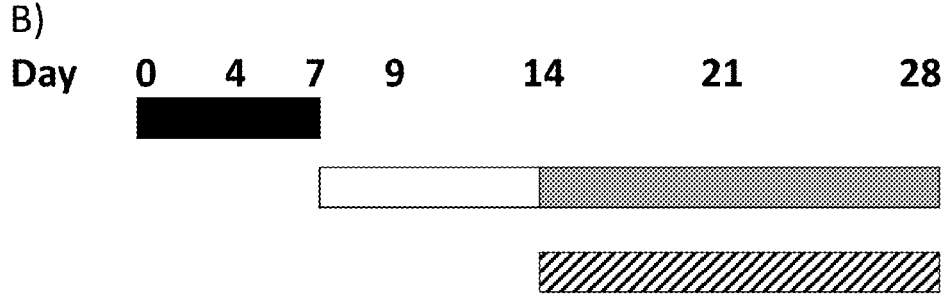
Figure 3:
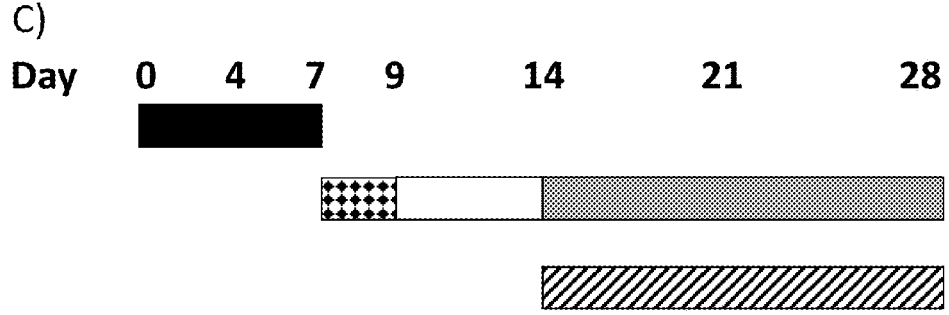

FIG. 3. Further variants of protocols for differentiating hPS towards hepatocyte-like cells showing media and stages in the protocol of inducing hPS to hepatocyte-like cells. A) shows the control culture conditions without a GSK inhibitor. B) Shows the addition of a GSK3 inhibitor at day 14, or when the cells resemble cell of the hepatic progenitor type. C) Shows the use of a split media (SM) before the addition of the GSK3 inhibitor. The protocols are further described in examples 12-14.

Figure 4A:
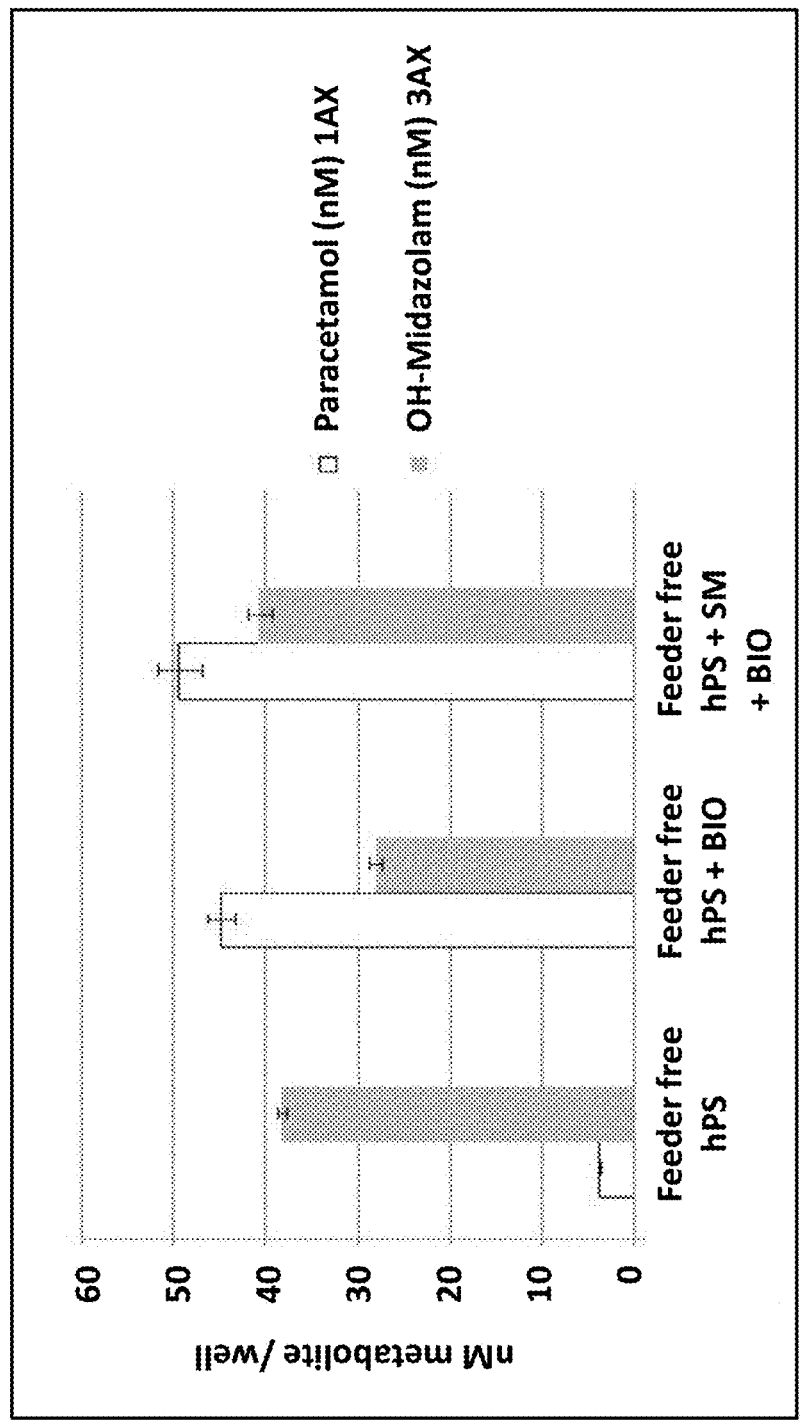
Figure 4B:
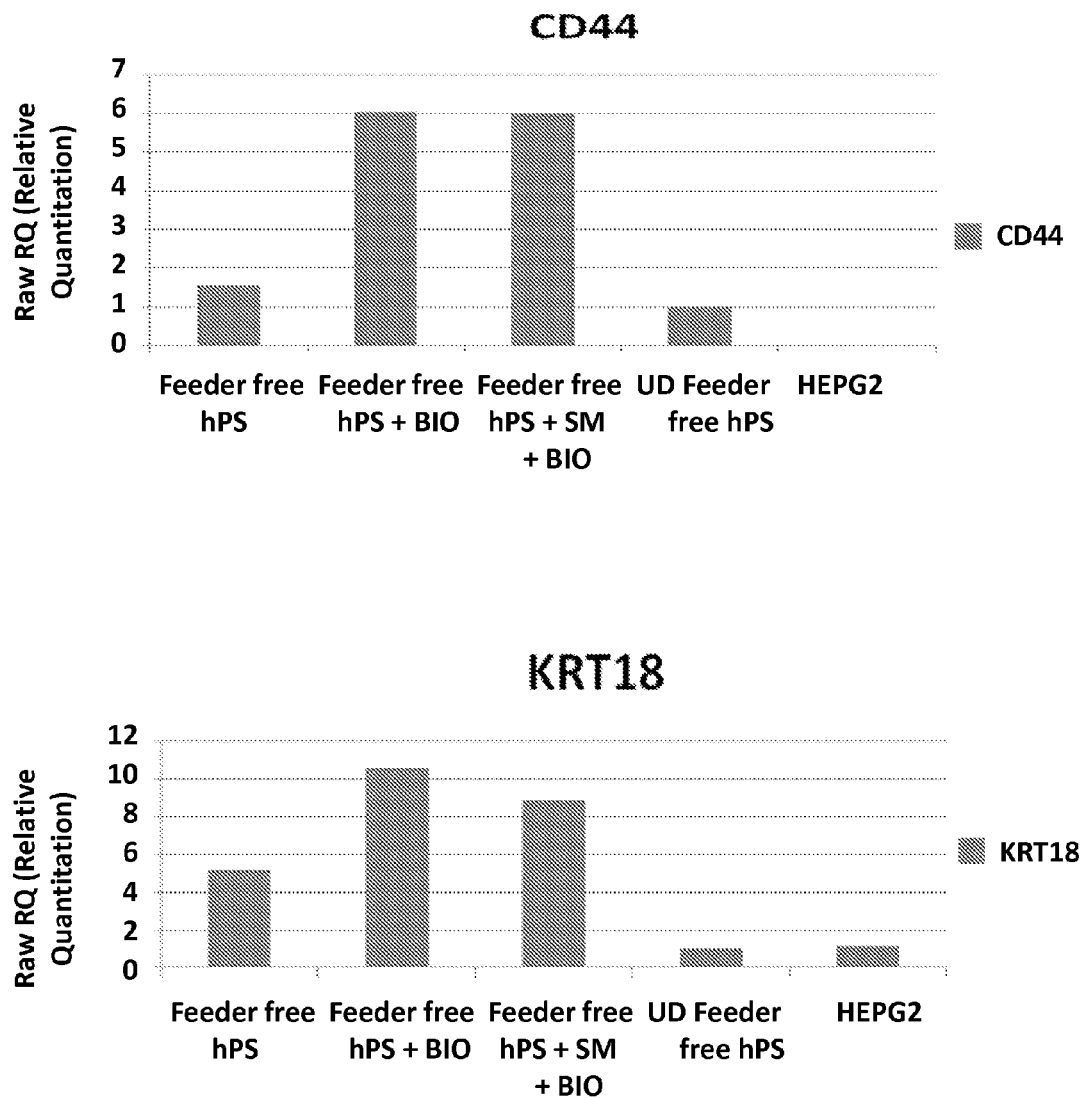
Figure 4C:
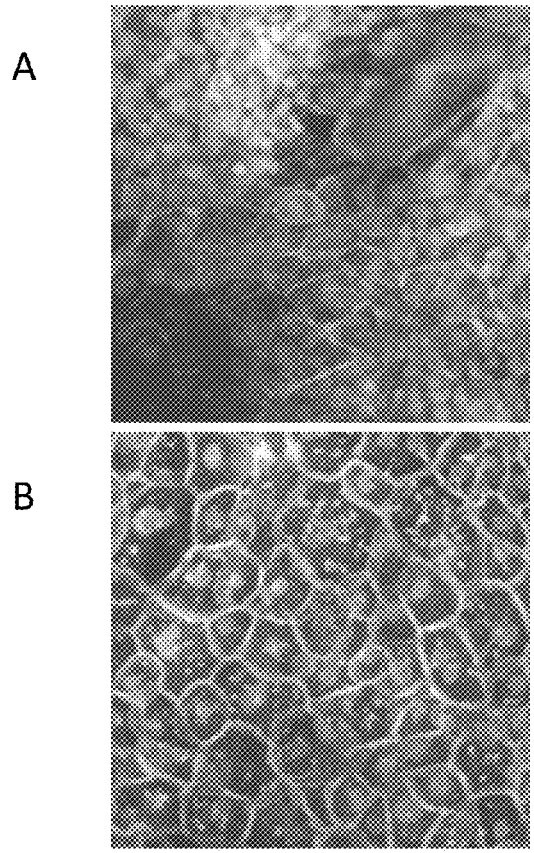

FIG. 4. Feeder free cultured hPS cells with and without the GSK3 inhibitor, as well as an alternative method where a split media as described in FIG. 3C were compared for their hepatic profile and homogeneity.

A) Results from Activity assay of CYP1A and CYP3A measured by conversion of paracetamol and OH_midazolam respectively. The use of a split media shows that high levels of CYP3AX can be maintained when a GSK3 inhibitor and a split media is used.

B) Shows a possible increase in proliferation by addition of a GSK-3 inhibitor, measured by an increase of the progenitor marker CD44 when a GSK3 inhibitor was added. The split media (SM) gave the same levels as without split media. Two controls were used undifferentiated cells cultured feeder free (UD feeder free) and a perpetual cell line from a hepatocellular carcinoma (HepG2). The levels of AFP, KRT18 (Keratin 18) and KRT19 (Keratin 19) indicate that the cells are maintained in a stage where they still have the ability to proliferate. The cells were 23 days when they were analyzed, n=3.

C) Immunolocalisation of Beta-catenin and Dapi staining of hES-HEP-BIO (A) and hES-HEP+BIO (B) Beta-catenin is localized at the cell membrane in hES-HEP cultures not treated and treated with BIO. Beta catenin in the cytoplasm and nuclei is commonly observed in BIO treated hES-HEP cultures. Day 21, 20×

Figure 5B:
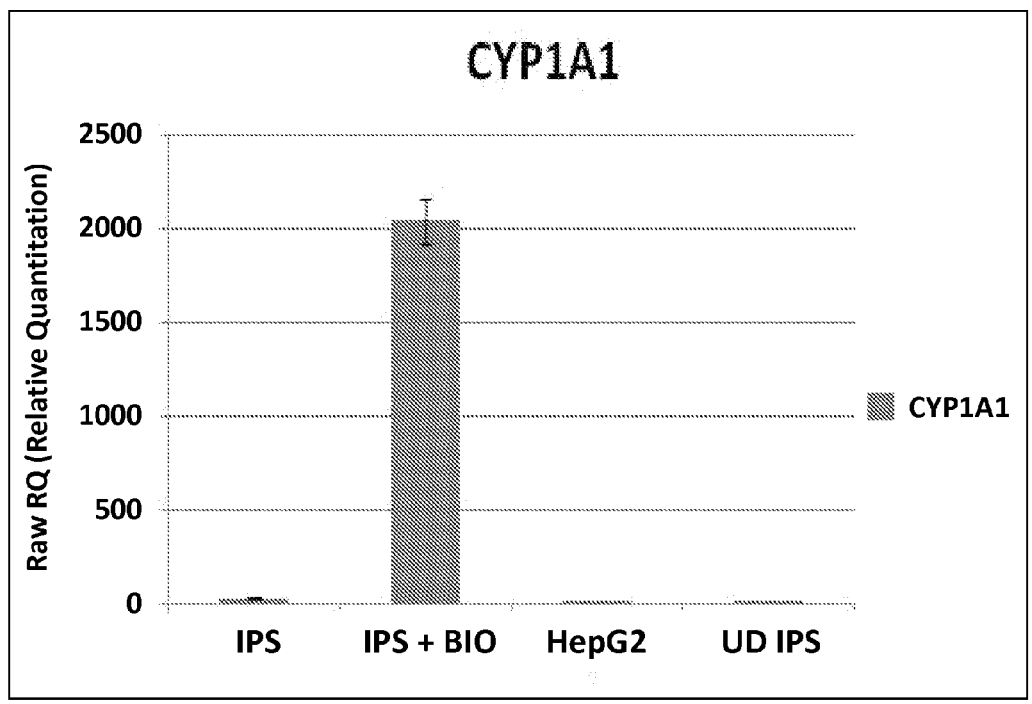

FIG. 5. hiPS cells cultured with and without the GSK3 inhibitor were compared for their hepatic profile and homogeneity. Where a GSK3 inhibitor was added it was added at a later stage of the differentiation, according to FIG. 3. Derivation of hepatocytes from human induced pluripotent stem cells (hiPS).

A) Results from Activity Assay of CYP1A, 3A and 2C. The addition of a GSK3 inhibitor gave increased activity of CYP1A and CYP3A. The levels of CYP2C are high in relation to what is usually shown for hepatocyte-like cells derived from hPS cells. The cells were 30 days, n=8. hiPS vs hiPS+BIO.

B) Results of hepatic markers from Q-PCR of the same cells that were analysed by Activity assay (Q-PCR hiPS +/−BIO) n=4. The results show a clear increase of CYP1A1, CYP1A2, CYP3A4 and CYP7A1. The levels of CYP2C9 where maintained high for the hiPS cells when a GSK inhibitor was added. The decreased AFP levels indicate maturation. Albumin was maintained at a level high compared to known protocols for the derivation of hepatocyte-like cells from hPS cells. AAT was maintained on a high level. Important transporters such as MRP2, Oct-1, GSTA1, BCEP and OATP2 where maintained at levels significantly higher than HepG2 showing a maturation of the hiPS cell derived hepatocyte-like cells.

Figure 6B:
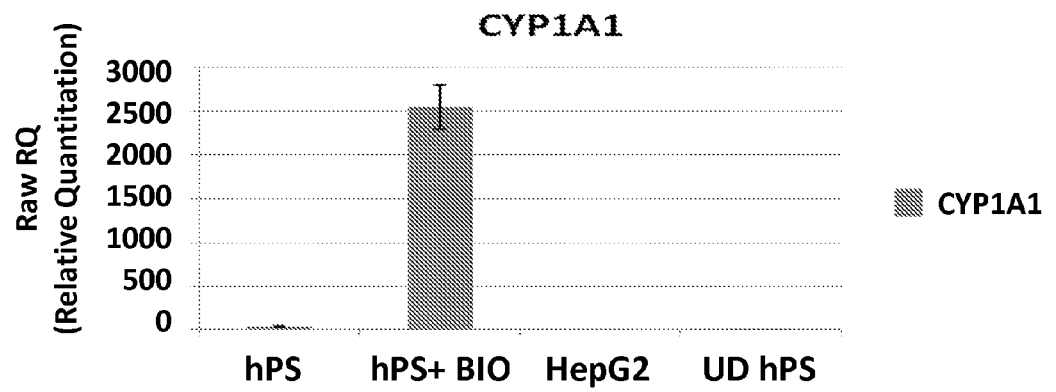
Figure 6B:
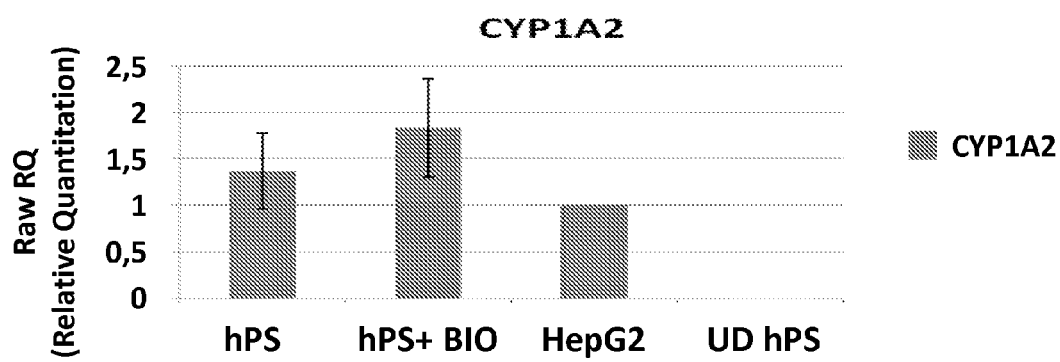

FIG. 6. hES cells cultured with and without the GSK3 inhibitor were compared for their hepatic profile and homogeneity, as described in examples 12 and 13. Where a GSK3 inhibitor was added it was added at a later stage of the differentiation, according to FIG. 3B.

A) Results from Activity Assay of CYP1A, 3A and 2C. The addition of a GSK3 inhibitor gave increased activity of CYP1A, 3A and 2C. The cells were 30 days, n=8. hPS vs hPS+BIO.B)

B) Results of hepatic markers from Q-PCR of the same cells that were analysed by Activity assay (Q-PCR hPS +/−BIO) n=4. The results show a clear increase of CYP1A1, CYP1A2, CYP3A4, CYP2C9 and CYP7A1. An increase in AAT was shown when BIO was added. Important transporters such as MRP2, Oct-1, GSTA1, BCEP and OATP2 where maintained at levels showing a maturation of the hPS cell derived hepatocyte-like cells.

FIG. 7. Induction of Cyp1A by GSK3I3 inhibitor in hESC derived hepatocytes.

A) Shows Cytochrome P450 activity of CYP1A in hESC-HEP differentiated with and without GSK3f3 inhibitor (Example 4 (MMI-BIO) vs. Example 8 (MMI+BIO) vs. Example 9 (MMII+BIO)). Analysis are performed at day 16-18 (n=7-8), 20-21 (n=5) and 25 (n=2) respectively, mean±SD. The tables list the increase of CYP activity as a fold change value.

B) Show gene expression levels of CYP1A1 and CYP1A2 respectively in hepatocyte-like cells differentiated in the presence of GSK3 inhibitor (Example 9) compared to HepG2. Analysis are performed day 16-18 (n=5), 19-21 (n=4) for CYP1A2 and day 16-19 (n=14), 21-23 (n=6) for CYP1A1, mean±SD. (Cells obtained as described in example 9 vs. HepG2 cells vs. hPS cells)

C) show immunocytochemistry of CYP1A2 (red) at day 19 in hepatocyte-like cells differentiated in the presence of GSK3f3 inhibitor (Example 9).

FIG. 8. Differentiation of hESC derived hepatocytes in the presence of GSK3 inhibitor from day 3 purifies hepatocytes from other cell types.

Figure 2:
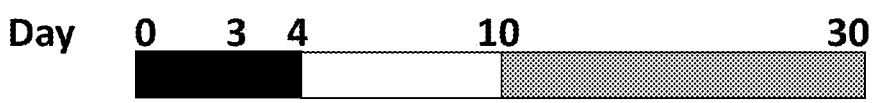
FIG. 2. Detailed variants of the protocols for differentiating hPS towards hepatocyte-like cells, protocol i to iv, as further described in examples 4-11.
Figure 2:
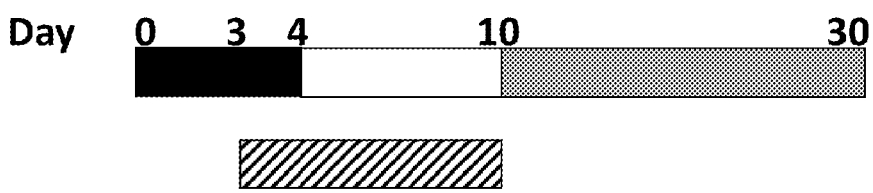
Figure 2:
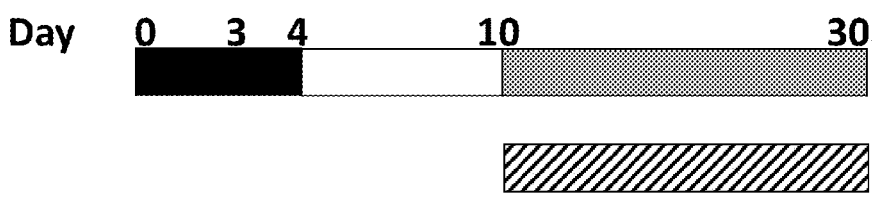
Figure 2:
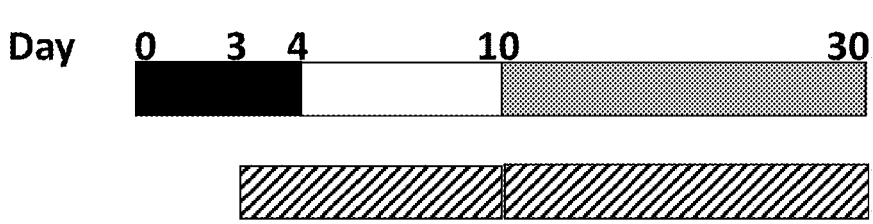

A-C show hESC-HEP at day 17, differentiated by protocol i or ii according to FIG. 2. D-E show hESC-HEP at day 15, differentiated by protocol iii or vi according to FIG. 2, A) 0 µM BIO, protocol i.
B) 1 µM BIO day 3-9, protocol ii.
C) 5 µM BIO day 3-9, protocol ii.
D) 0 µM BIO day 3-9, 1.5 µM BIO day 10-15 protocol iii,
E) 3.5 µM BIO day 3-9, 1.5 µM BIO day 10-15 protocol vi.

A and B show hESC-HEP cultures which are over grown by another cell type where as in C the majority of cells in the culture are hepatocyte-like cells. E represent a purer hESC-HEP culture than D. White arrow: hepatocyte-like cells, black arrow: other cell type than hepatocyte-like cells. Scale bar: 100 µm.

Figure 9:
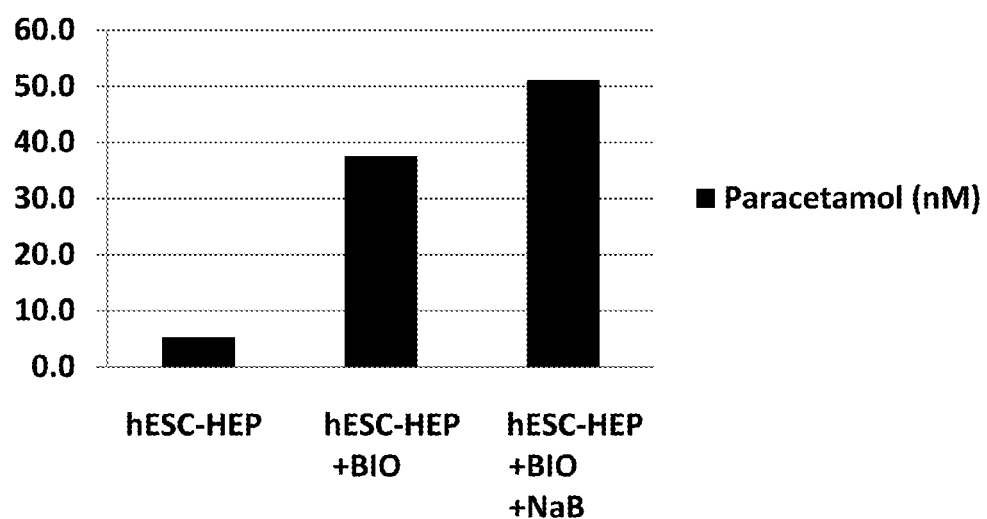
Figure 10A:
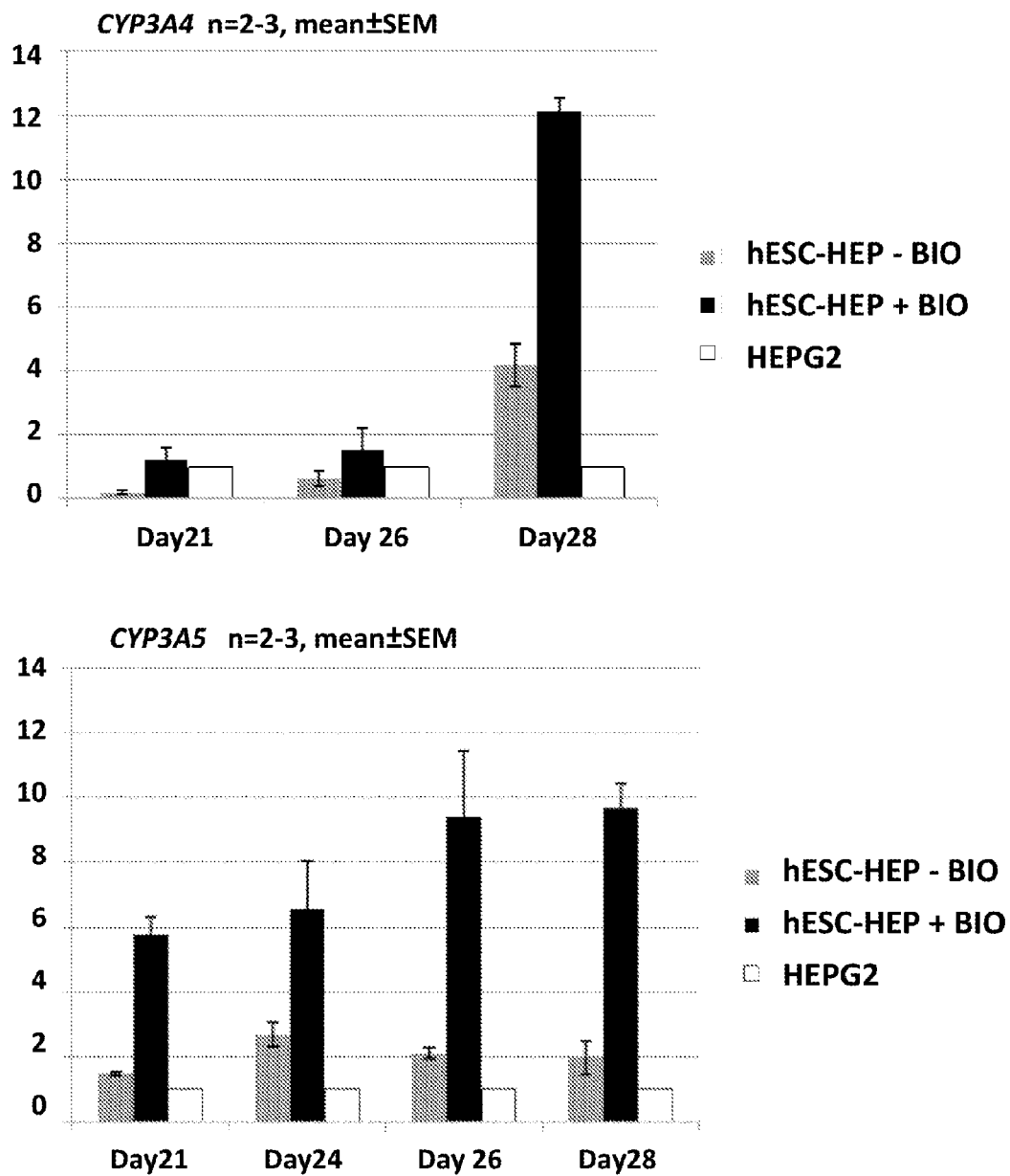
Figure 10B:
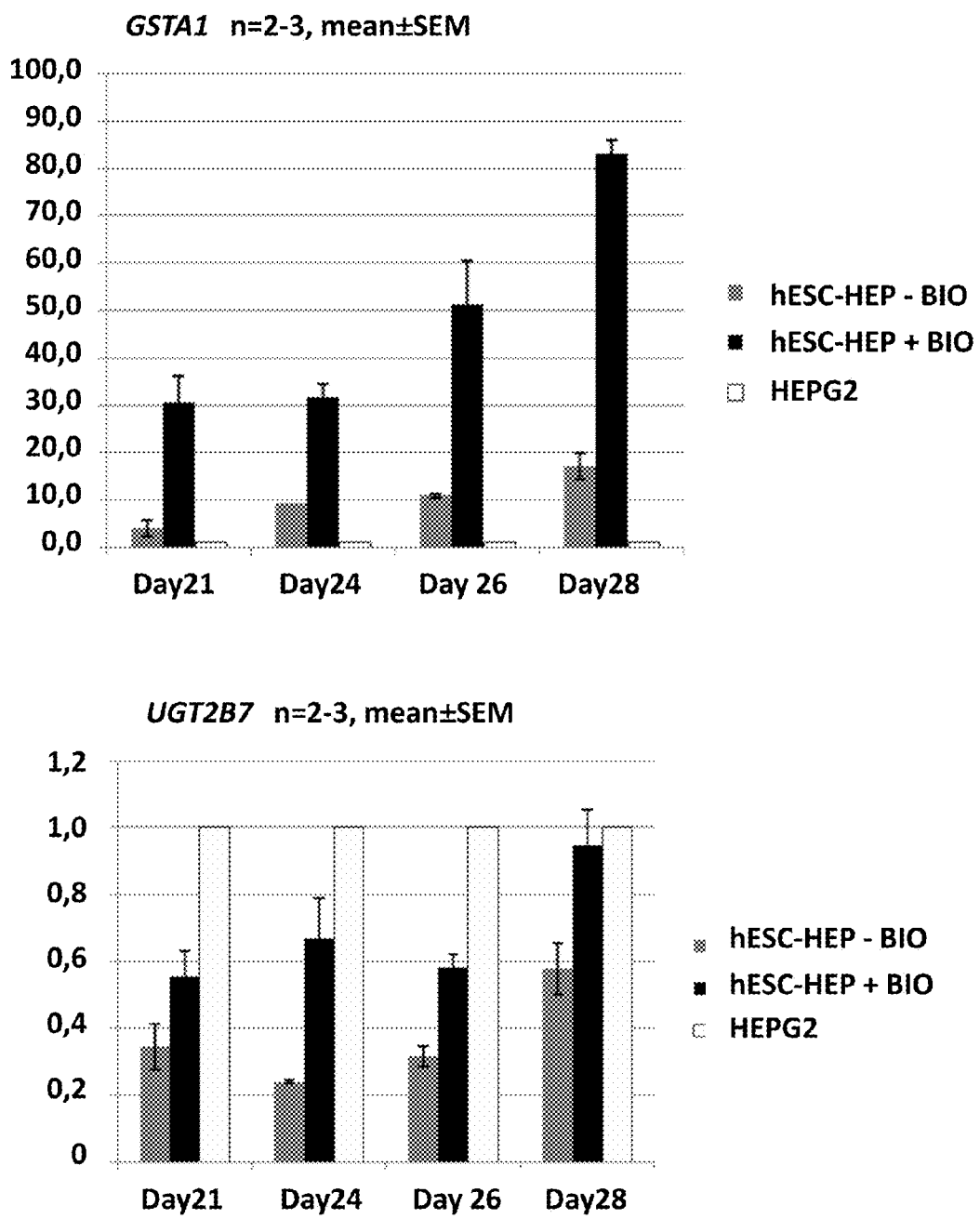
Figure 10C:
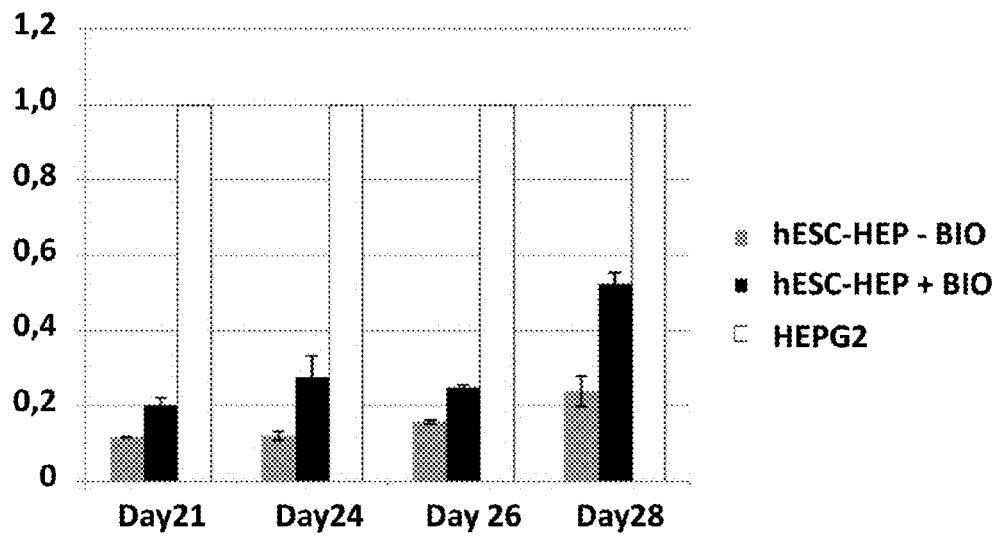
Figure 10C:
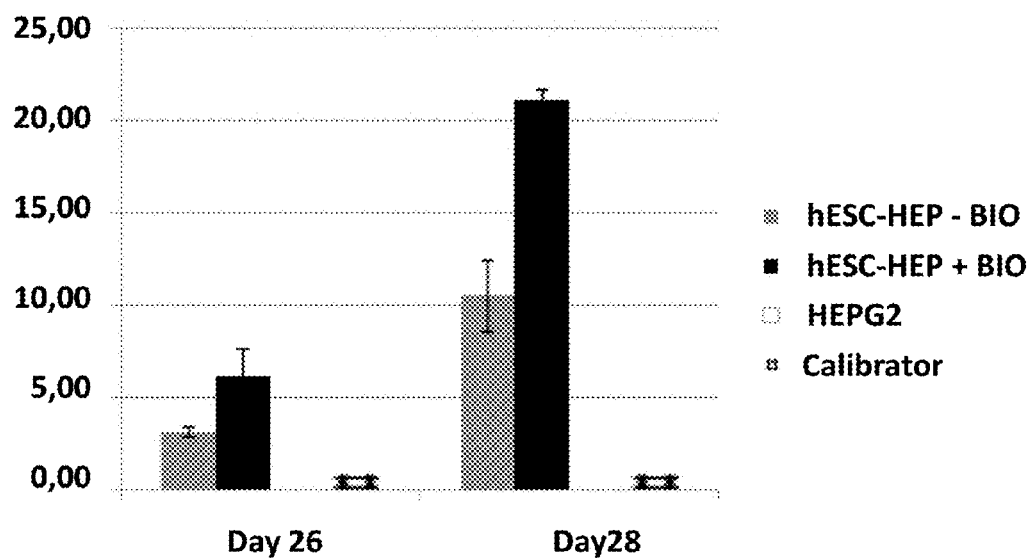
Figure 10D:
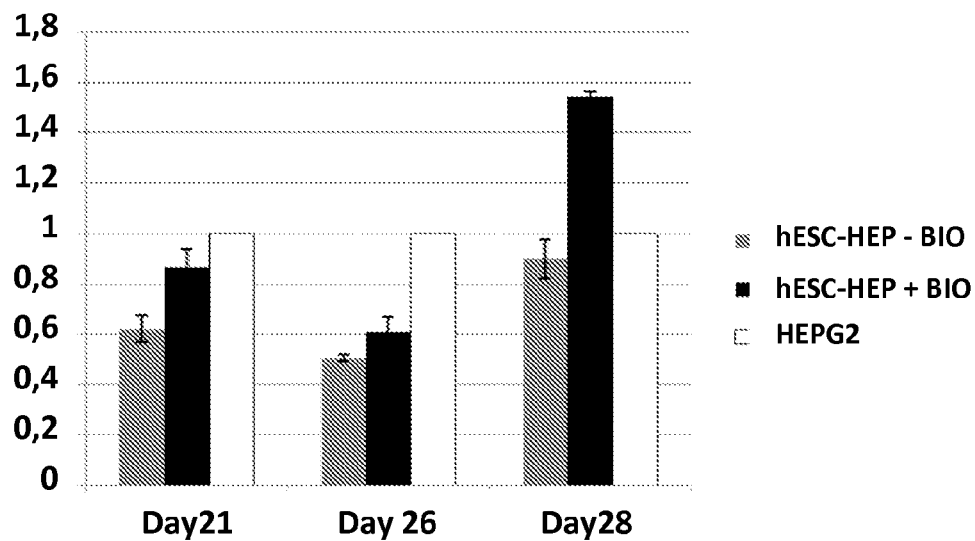
Figure 10D:
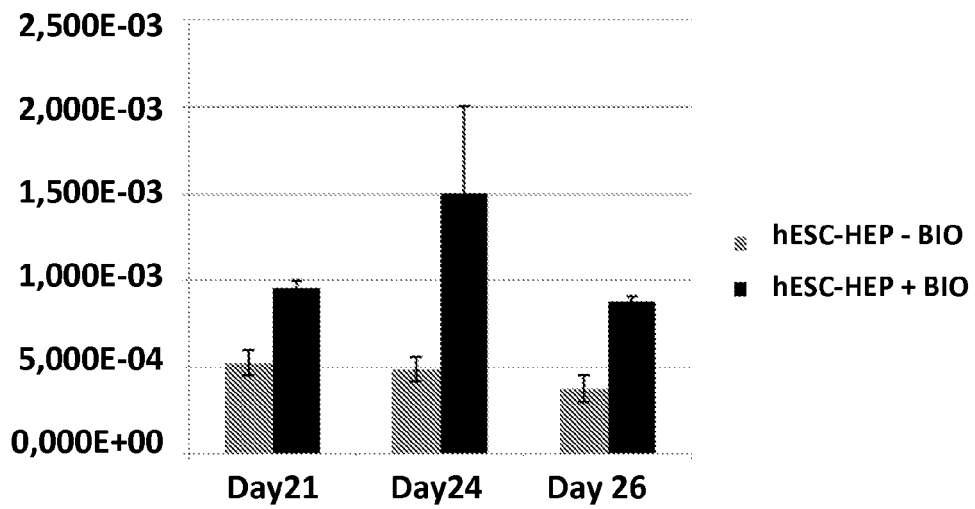

FIG. 9. Functional CYP1A activity in hES-HEP cultures differentiated in media supplemented with NaB (an Histone deacetylase inhibitor (HDAC) inhibitor) and BIO (a GSK3 inhibitor), compared to cultures without NaB in the maturation media, suggesting HDAC inhibitors, eg NaB, to potentiate Wnt-signalling mediated transcription. Analysis is performed day 24-25, n=1.

FIG. 10. Gene expression levels of hepatic markers are induced by BIO supplemented at day 3. Qrt-PCR data is presented as fold change gene expression levels of HepG2 except for BSEP, which graph show fold change of calibrator. N=2-3, mean±SEM. FIG. 10 corresponds to example 22.

A) Phase I, drug metabolising enzymes: CYP3A4, CYP3A5, and CYP2C9 show increased expression levels at the addition of BIO. CYP3A7 shows no significant increase B) Phase II, drug metabolising enzymes: GSTA1 and UGT2B7 shows and increased expression when BIO was added.

C) Phase III, transporters MRP2 and BSEP shows both increased expression when BIO was added.

D) General liver markers: A1AT showed a strong increase at day 28. ALB decreased at day 26 indicating maturation of the hepatocyte-like cells. TAT showed higher expression levels than for the cells cultured with BIO than the ones with out BIO for all days.

Figure 11:
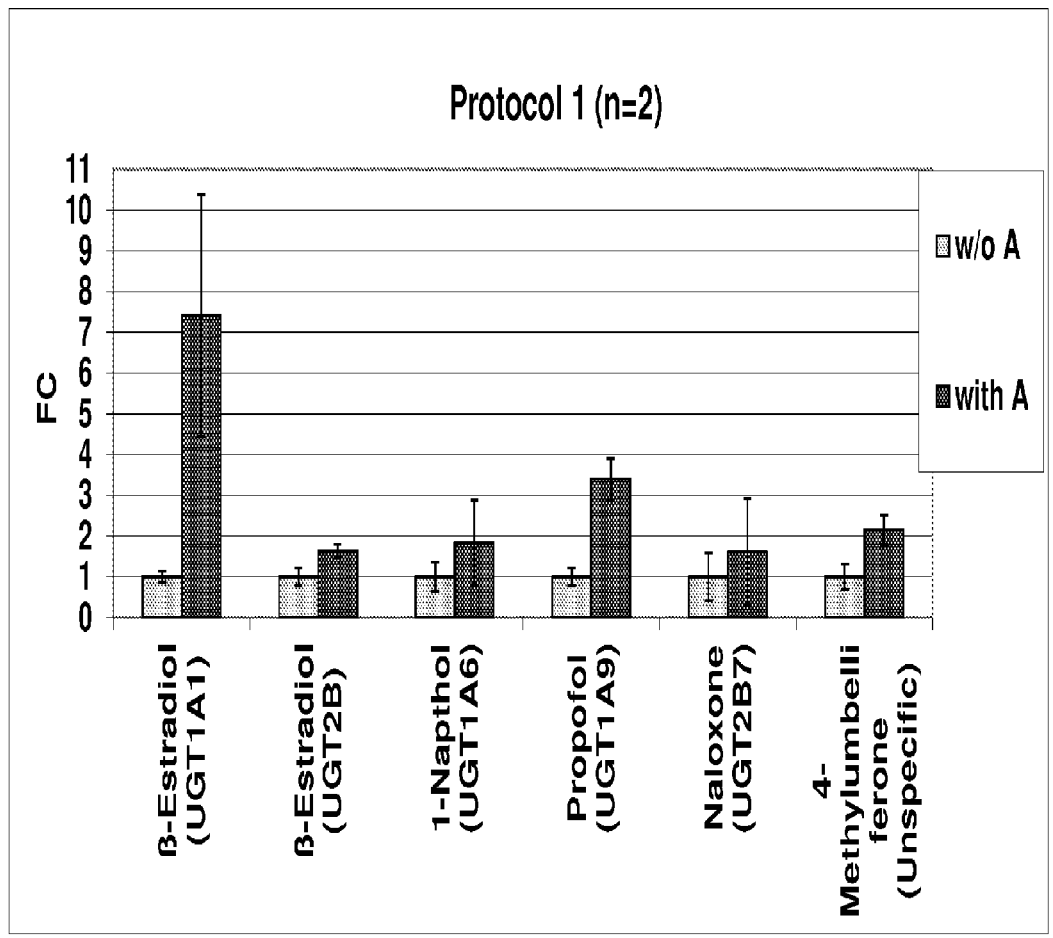

FIG. 11. Relative expression levels of UGT hepatic metabolic markers in hESC-HEP generated with or without Wnt-signalling modulation by GSK-3 inhibitor BIO during endoderm to hepatocyte-like cell phase. FC=fold change relative expression, control set to 1 for each example. Graphs show expression levels in cells treated with one of three differentiation/maturation protocols (see example 21) and +/−GSK-3 inhibitor treatment for activity of UGTs on specific UGT substrates: (UGT1A1,[β-estradiol]); (UGT2B, [β-estradiol]; (UGT1A6, [1-Napthol]), (UGT1A9, [Propofol]), (UGT2B7, [Naloxone]). A non-sepcific control (Methylumbelliferone) was also included. n=number of experiments averaged to obtain results.

Figure 12A:
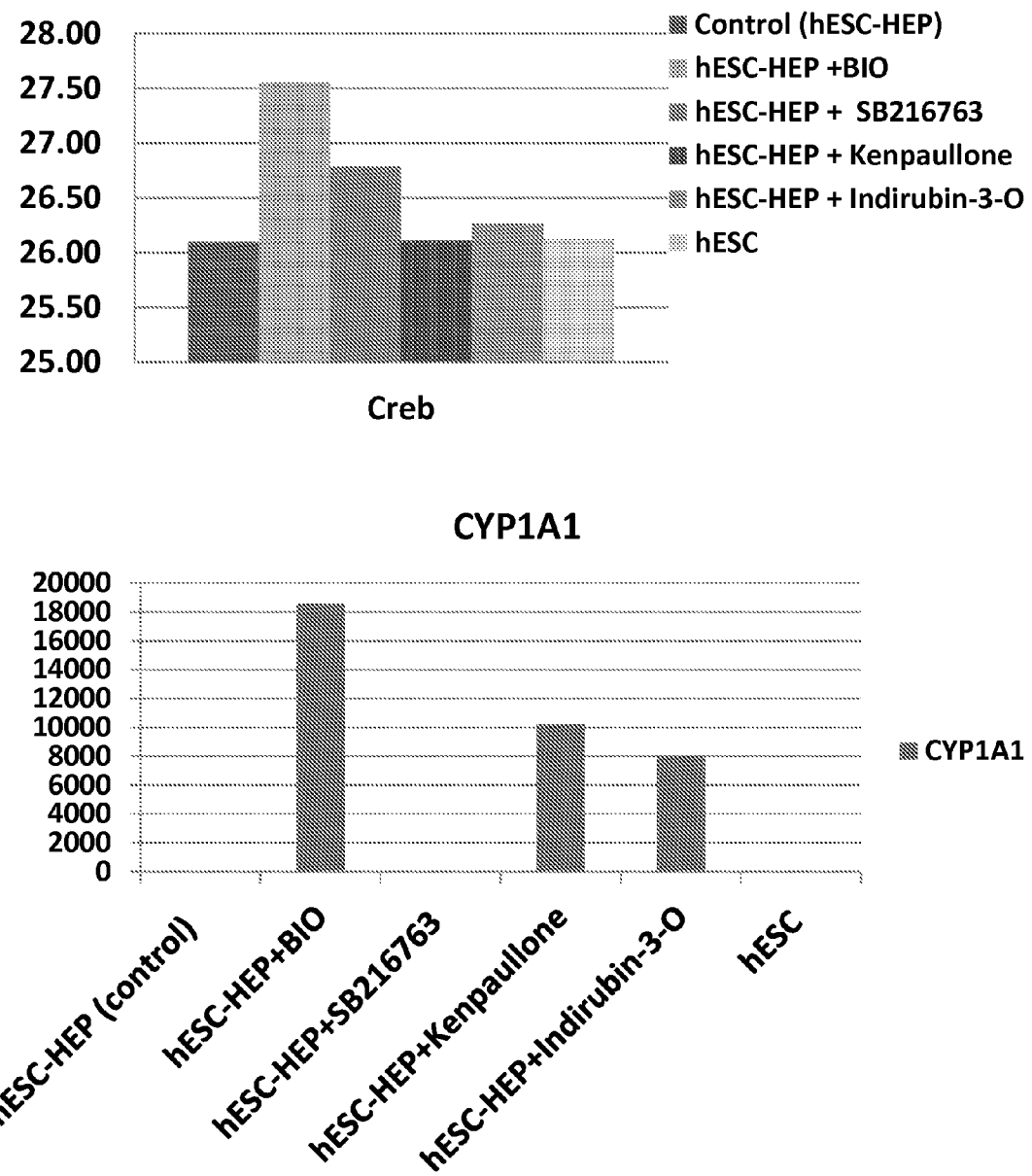
Figure 12B:
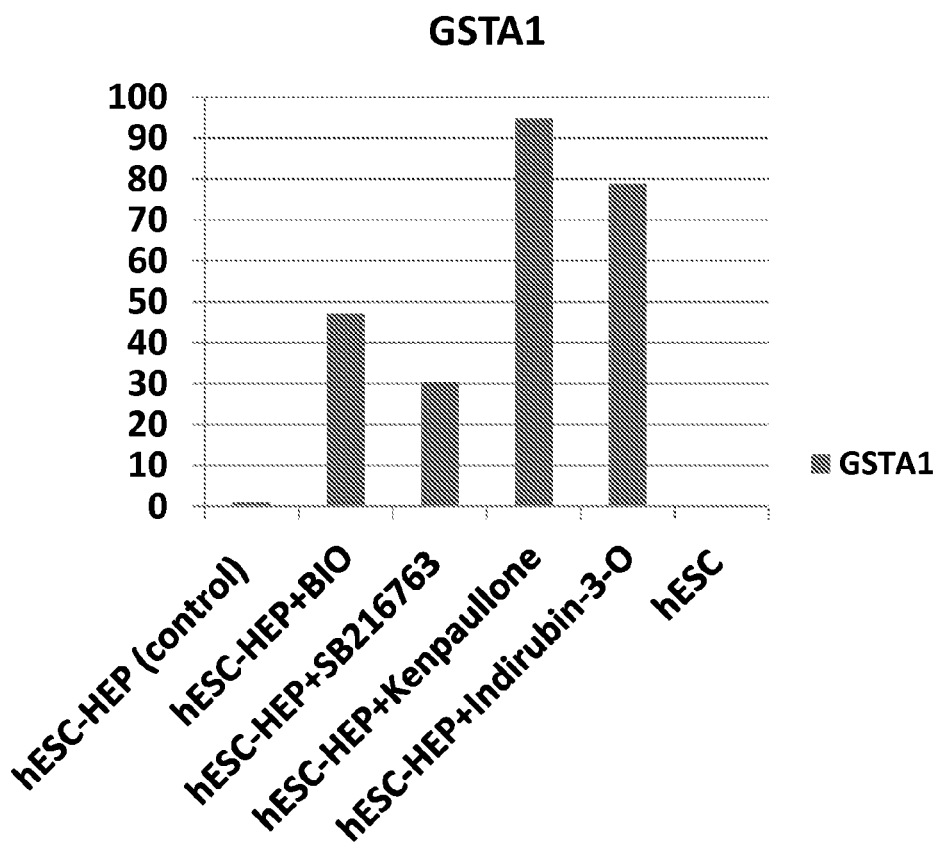

FIG. 12. Relative expression levels of hepatic markers in hESC-HEP generated with modulation of Wnt-signalling by GSK-3 inhibitors other than BIO during later maturation period (day 10 onwards). Treatments shown include: hESC-HEP (negative control; cells never exposed to GSK-inhibitor during differentiation), BIO, SB216763, Kenpaullone, Indirubin-3-O; also included is a second negative control undifferentiated hESC cells (hESC). FIG. 12A shows expression of Phase I enzymes, FIG. 12B shows expression of Phase II enzymes and hepatic markers. GSK-3 inhibitors were present only during later differentiation (from day 10 onwards); also included is a further negative control graph showing the expression levels of a housekeeping gene (Creb) across the various samples.

Figure 13A:
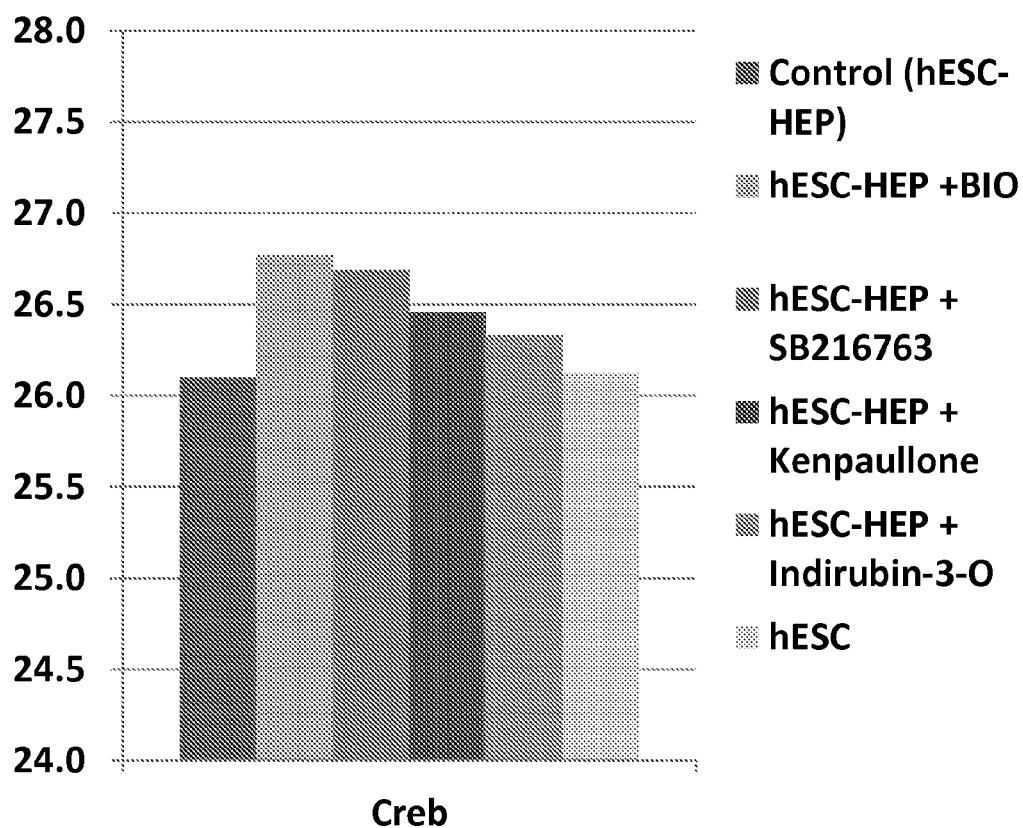
Figure 13B:
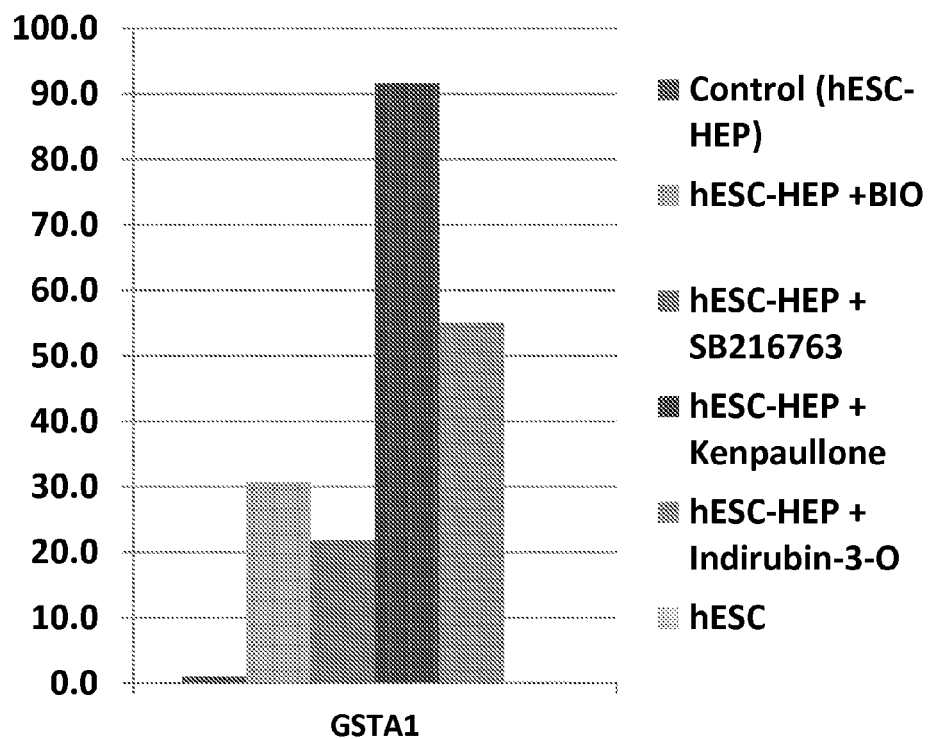

FIG. 13. Relative expression levels of hepatic markers in hESC-HEP generated with modulation of Wnt-signalling by GSK-3 inhibitors other than BIO during both mid (days 3-9) and late stage (days 10-23) differentiation. Treatments shown include: hESC-HEP (negative control; cells never exposed to GSK-inhibitors), BIO, SB216763, Kenpaullone, Indirubin-3-O; also included is a second negative control undifferentiated hESC cells (hESC); also included is a further negative control graph showing the expression levels of a housekeeping gene (Creb) across the various samples. FIG. 13A shows expression of Phase I enzymes, FIG. 13B shows expression of Phase II enzymes andhepatic markers.

Figure 14A:
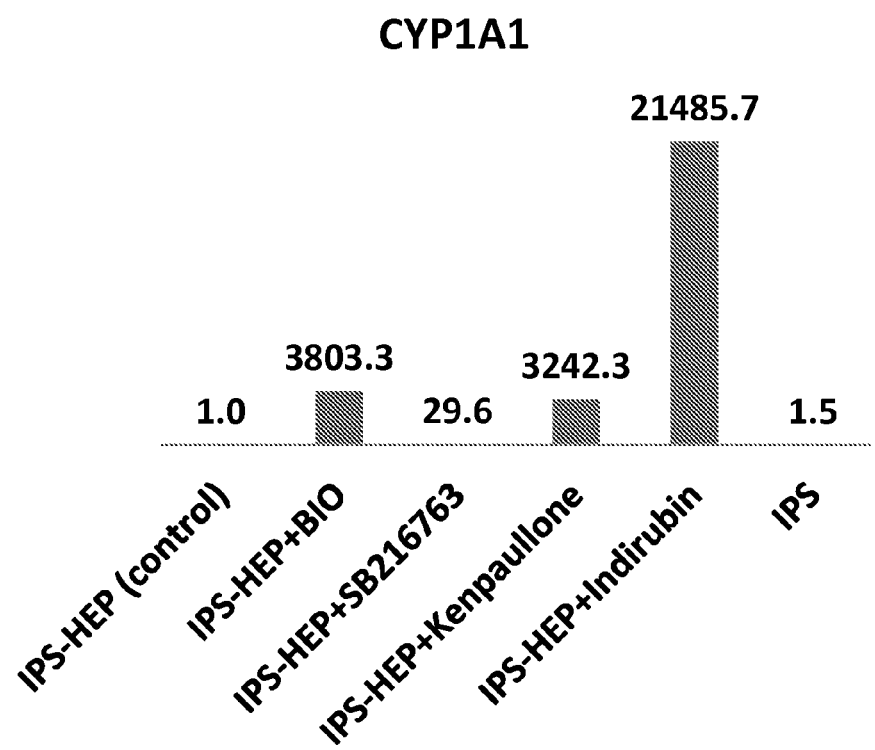
Figure 14B:
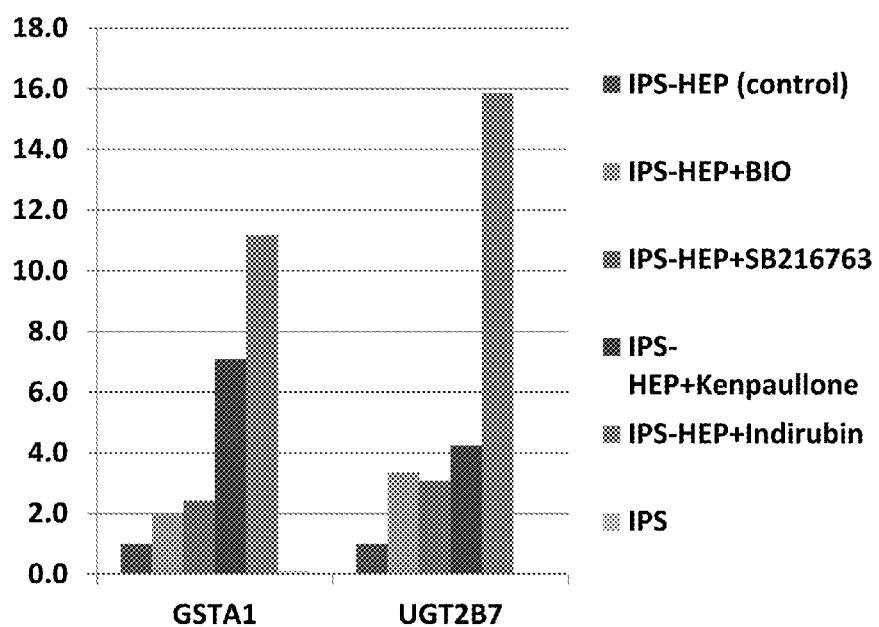
Figure 14C:
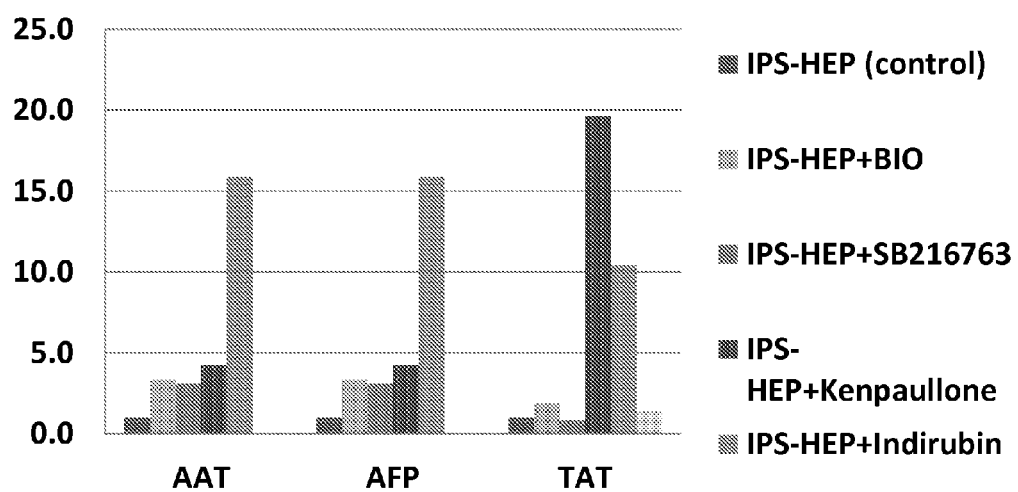

FIG. 14. Relative expression levels of Phase I enzymes (A), Phase II enzymes (B) and General hepatic markers (C) in hiPS-HEP cells generated with modulation of Wnt-signalling by GSK-3 inhibitors other than BIO during later (day 10+) differentiation. Treatments shown include: iPS-HEP (negative control; cells never exposed to GSK-inhibitors), BIO, SB216763, Kenpaullone, Indirubin-3-O; also included is a second negative control undifferentiated hiPS cells (iPS).

Figure 15A:
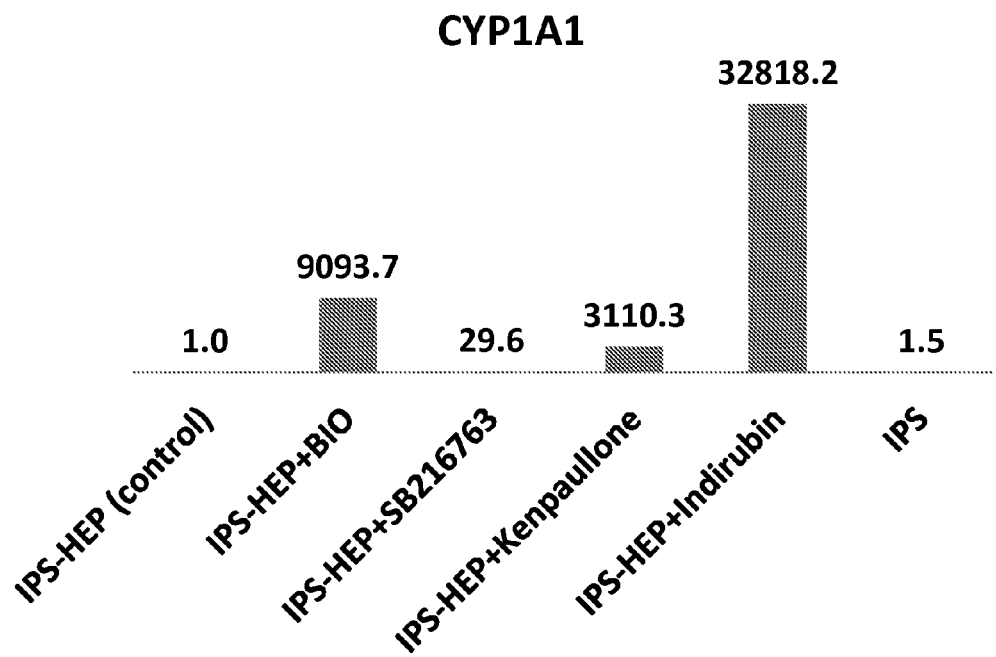
Figure 15B:
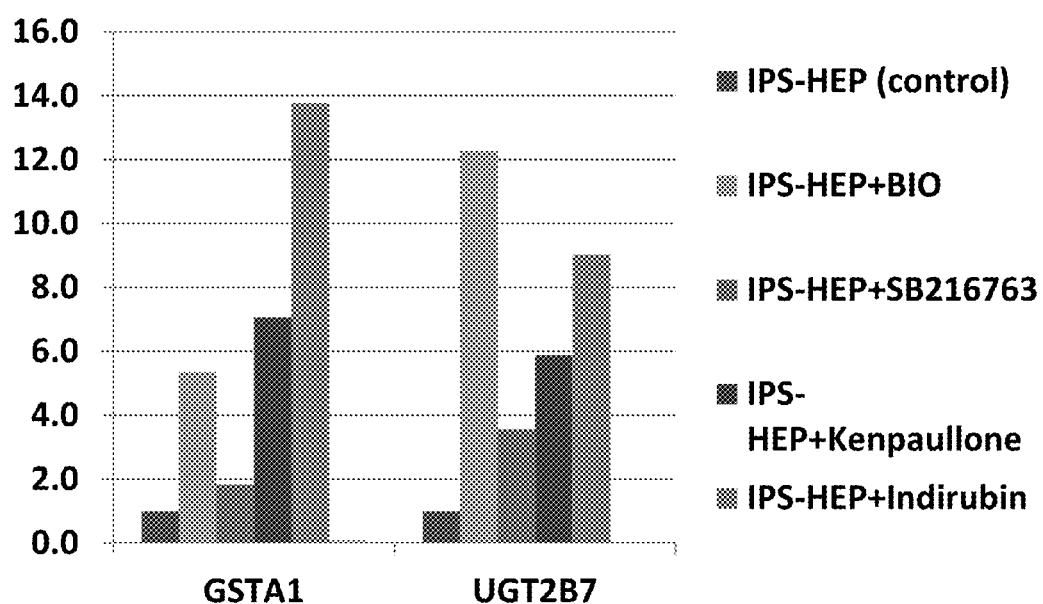

FIG. 15. Relative expression levels of Phase I enzymes (A), Phase II enzymes (B) and General hepatic markers (C) in hiPS-HEP cells generated with modulation of Wnt-signalling by GSK-3 inhibitors other than BIO during both mid (days 3-9) and late stage (days 10-23) differentiation. Treatments shown include: iPS-HEP (negative control; cells never exposed to GSK-inhibitors), BIO, SB216763, Kenpaullone, Indirubin-3-O; also included is a second negative control undifferentiated hiPS cells (iPS).

EXAMPLES

In present invention, several modulators of the Wnt pathway have been tested, including GSK inhibitor BIO (GSK inhibitor IX), Kenpaullone, SB216763 and Indirubin-3'-oxime. As well known within the field and discussed in the scientific literature as example (Nejak-Bowen et al 2008), the other GSK-3 inhibitors and other molecules effecting the signalling cascade are suggested to have a similar effect for modulation of Wnt signalling pathway. Examples of general culturing and passaging techniques are disclosed in pending applications PCT/EP2004/005033, PCT/EP02/14895, PCT/

EP2005/040582, PCT/EP2006/009697, PCT/EP2007/004940 and PCT/EP208/059491.

As laid out in the examples, the starting material may comprise any pluripotent stem cell derived through an initial differentiation towards a definitive or extraembryonic lineage. The starting material may also be any cell of hepatic progenitor lineage.

Example 1

Starting Material for Hepatocytes Derived from Human Pluripotent Stem Cells Maintained on Feeder Cells All hPS cells (as defined above) can be used as staring material for this invention. For the examples below in particular hepatocyte-like cells were derived in vitro from undifferentiated human embryonic stem cells (hESC) cultured on mEF cells (Heins et al 2004, Stem Cells). The cell lines used for this experiment could be, but is not limited to the hES cell line SA002, SA121 and SA181 (Cellartis A B, Goteborg, Sweden) and they can be propagated as described Heins et al. 2004. These cell lines are listed in the NIH stem cell registry, the UK Stem Cell bank and the European hESC registry and are available on request. Along with hPS obtained from hESC, hPS cells invention hPS obtained from hiPS (induced pluripotent stem cells) have been used for the derivation of hepatocytes for the examples of this invention.

Example 2

Derivation of hepatocytes from human pluripotent stem cells using a GSK3-inhibitor. Hepatocytes were derived from both hES cells and human hiPS cells according to the protocol in FIG. 1, this protocol gives an overview of the derivation of human hepatocyte-like cells from human pluripotent stem cells.

Before adding the first medium, ID day 0-2, the cultures were washed thoroughly with PBS, twice. The different mediums were prepared freshly and added day 0 (ID day 0-1), 2 (ID day 2-4), 4 and 7-10 every second or third day (VH1), 10-28 every second or third day (MMI or MM II). Cells are passaged at day 4 and replated at a cell density of 50 000-350 000 cells/cm$^2$ such as e.g. 100 000-300 000 cells/cm$^2$, preferably 200 000 cells/cm$^2$.

The Initial Differentiation (ID) Step
Day 0-1
RPMI 1640 (+0.1% PEST, +1% Glutamax)
1×B27
100 ng/ml Activin A
1 mM NaB
Day 2-3
RPMI 1640 (+0.1% PEST+1% Glutamax)
1×B27
100 ng/ml Activin A
0.5 mM NaB
Hepatic Progenitor Step
Day3
+/−3.5 µM GSK-3 inhibitor (e.g. BIO)
VH1
Day 4-9
VitroHES
1% DMSO
+/−3.5 µM GSK-3 inhibitor (e.g. BIO)
Maturation Media (MM) I
Day 10-30
WME+SQ (−GA1000)+1% Glutamax+0.1% PEST)
10 ng/ml OsM
0.1 µM DexM
2 ng/ml bFGF
10 ng/mlHGF
0.5% DMSO
10 mM Nicotinamide
ITS (10 µl/ml)
3 ng/ml Glucagon
+/−1.5 µM GSK-3 inhibitor (e.g. BIO)

Example 3

Figure 1:
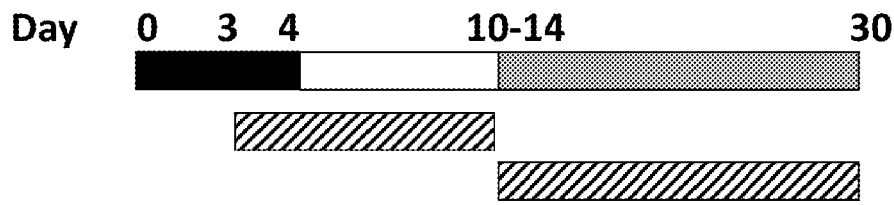
FIG. 1. Overview of the derivation protocol of hepatocyte-like cells from hPS, as further outlined in example 2 and 3. The striped bar describes the times for addition of a GSK3 inhibitor.

As outlined in Example 2 and in FIG. 1, but with maturation medium II (MM II) replacing maturation medium I (MM I).
Maturation Media (MM) II
Day 10-30
WME+SQ (−GA1000)+1% Glutamax+0.1% PEST)
10 ng/ml OsM
0.1 µM DexM
20 ng/ml HGF
0.5% DMSO
+/−1.5 µM GSK-3 inhibitor (e.g. BIO)

Example 4

As Example 2, but without addition of a GSK3 inhibitor. Example 4 is a control protocol in which hESC were differentiated into hepatocyte-like cells in the absence of GSK3 inhibitor.

As outlined in FIG. 2) (i-iv), variants of the overview protocol in FIG. 1 were tested. The differentiation procedure follows three stages, first during the initial differentiation (ID) step, partly differentiated cells resembling endodermal cells are formed (day 0-4), second the partly differentiated cells are differentiated into hepatoblasts/hepatic progenitors (day 4-10) and finally the hepatoblasts are matured into hepatocyte-like cells (day 10-30).

Example 4 was performed as schematically depicted in FIG. 2i.

Example 5

As example 3, but without addition of a GSK3 inhibitor. Included as a control protocol of which hESCs were differentiated into hepatocyte-like cells in the absence of GSK3 inhibitor.

Example 5 was performed as schematically depicted in FIG. 2i.

Example 6

Schematically depicted in FIG. 2ii. As example 2 but with 3.5 µM GSK3 inhibitor is added at day 3 to day 10 only.

Example 7

Schematically depicted in FIG. 2ii. As example 3 but with 3.5 µM GSK3 inhibitor is added at day 3 to day 10 only.

Example 8

Schematically depicted in FIG. 2iii.
As example 2 but with 1.5 µM GSK3 inhibitor is added at day 10 to day 30 only.

Example 9

Schematically depicted in FIG. 2iii.
As example 3 but with 1.5 μM GSK3 inhibitor is added at day 10 to day 30 only.

Example 10

Schematically depicted in FIG. 2iv. As example 2 but with 3.5 μM GSK3 inhibitor added at day 3 to day 10 and changed to 1.5 μM GSK3 inhibitor at day 10 and throughout the protocol.

Example 11

Schematically depicted in FIG. 2iv. As example 3 but with 3.5 μM GSK3 inhibitor added at day 3 to day 10 and changed to 1.5 μM GSK3 inhibitor at day 10 and throughout the protocol.

Example 12

Medium and supplement factors for hepatocyte-like cells derived from feeder free hES or hiPS.
Wash the cells prior initiation of differentiation of the undifferentiated hPS hepatocyte-like cells. Before adding the first medium, Initial differentiation (ID) step day 0-2, the undifferentiated cultures (UD) in T150 flasks were washed thoroughly with PBS or RPMI640, twice. The different mediums were prepared freshly and added daily at day 0 (ID day 0-1), 2, 3 and 4 (ID day 2-4), 4. Then the cells were passaged at a concentration of approximately 200,000 cells/cm$^2$ to freshly gelatine- or matrigel coated 24 well plates in VH1 medium. The maturation medium was then changed every second day or third day for day 7-10, and for day 10-28 every second or third day (BM2 or ModII). Example 12 illustrates the derivation without a GSK3 inhibitor (BIO) used as a control for this invention and was carried out as outlined in FIG. 3A).

The Initial Differentiation (ID) Step
Day 0-1
RPMI 1640 (+0.1% PEST, +1% Glutamax)
1×B27
100 ng/ml Activin A
1 mM NaB
ID
Day 2-7
RPMI 1640 (+0.1% PEST)
1×B27
100 ng/ml Activin A
0.5 mM NaB
Day 7 the cells are passaged with TtypLE Select. The cells are incubated for 3-7 minutes at 37° C. Diluted and washed with VH medium, spun at 300 g, 5 min. Thereafter, the cells were seeded onto fresh coated dishes.
VitroHES 1 Step (VH1)
Day 7-14
VitroHES™ (VH)
1% DMSO
Maturation Media BM2 (or Alternatively MMII (as Described in Example 2)) Day 14-28
WME+SQ (−GA1000, +1% Glutamax+0.1% PEST)
(10 ng/ml OsM)
0.1 μM DexM
10 ng/ml HGF
0.5% DMSO

Example 13

Performed as outlined in FIG. 3B). As example 7 but with 1.4 μM GSK3 inhibitor is added at day 14.

Example 14

Performed as outlined in FIG. 3C) describes the derivation with the cells cultured in a split medium between day 7-9 and a GSK3 inhibitor introduced at day 14.
The Initial Differentiation (ID) Step
day 0-1
RPMI 1640 (+0.1% PEST, +1% Glutamax)
1×B27
100 ng/ml Activin A
1 mM NaB
ID day 2-7
RPMI 1640 (+0.1% PEST)
1×B27
100 ng/ml activin A
0.5 mM NaB
Day 7 the cells are passaged with TrypLE Select. Incubated for 4 minutes at 37° C. Diluted and washed with VH4 medium, spun at 300 g, 5 min. Thereafter, the cells were seeded onto fresh coated dishes.
Split Media (SM) Day 7-9
RPMI A (+0.1% PEST+1% Glutamax (10 μl/ml)
100 ng/ml aFGF
5 ng/ml bFGF
50 ng/ml BMP2
200 ng/ml BMP4
0.2% FBS
VitroHES 1 Step (VH1) Day 9-14
VitroHes
1% DMSO
Maturation Media BM2 (or Alternatively MMII (as Described in Example 2)) Day 14-28
WME+SQ (−GA1000, +1% Glutamax+0.1% PEST)
(10 ng/ml OsM)
0.1 μM DexM
2 ng/ml bFGF
10 ng/ml HGF
0.5% DMSO
10 mM nicotineamide
10 μg/ml ITS
3 ng/ml Glucgon
1.4 μM BIO

Example 15

Induction of Cytochrome P450 1A in mEF-Cultured hESC Derived Hepatocytes by GSK3-Inhibitor.
MEF-cultured hESCs (hES cells cultured on feeder cells) were differentiated into hepatocyte-like cells according to examples 4, 8 and 9, thus comparing the absence of BIO, a GSK3-inhibitor (Example 4), to the influence of BIO during the maturation step (day 10-26) in maturation medium I and II (MM I and MM II)(Example 8 and 9 respectively). Before adding the first medium, ID day 0-2, the cultures were washed thoroughly with PBS, twice. The different mediums were prepared freshly and added day 0 (DE day 0-1), 2 (DE day 2-4), 4 and 7-10 every other to third day (VH1), 10-26 every second or third day (MMI or MM II). Detailed information about the composition of the different mediums, see examples 4, 8 and 9. At day four, the cells were passaged to new dishes in order to obtain a confluent layer of cells that subsequently was differentiated into hESC-HEP. Briefly, the cells were detached from the culture unit by incubating the cells in an enzyme solution, Tryple Select, for 5 to 10 min. VitroHes-medium was added to the cultures to stop the effect of the enzyme. The detached cells were transferred to tubes and centrifuged for 5 min at 300 g. The supernatant was discarded and VH1-medium added to the cell pellet, which was subsequently dissociated into single cell suspension. Cells were counted in a Bürker chamber and seeded out in 0.1% gelatine coated culture units (e.g. in 24-well plates) at a cell density of 150 to 250K cells per $cm^2$.

At day 16, 18, 20, 21 and 25 hESC-HEP cultures were analyzed for cytochrome P450 1A activity by incubating the substrate Phenacetine to a final concentration of 26 µM in Phenol Red-free Williams Medium E, supplemented with 0.1% Penicilline-Streptomycin 2 mM L-Glutamine and 25 mM Hepes. A volume of 220 µl diluted substrates were added per well of a 24-well plate. hESC-HEP cultures with substrates were incubated over night. After 16 h, medium was collected and subsequently, centrifuged at 10 000 g, 4° C. for 20 min. Samples were analysed by Liquid chromatography-mass spectrometry (LC-MS) LCMS for presence of the metabolite Paracetamol, biotransformed by the cytochrome p450 enzymes Cyp1A2, 1A1.

Figure 7A:
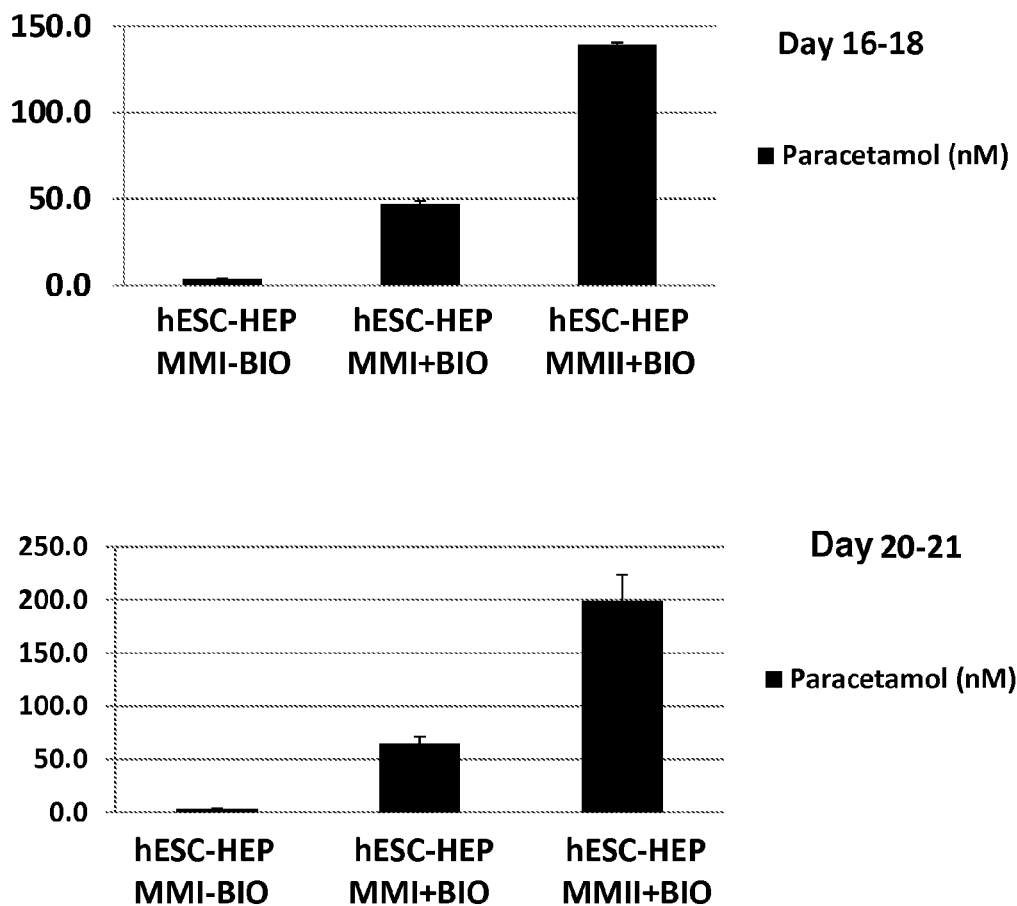
Figure 7B:
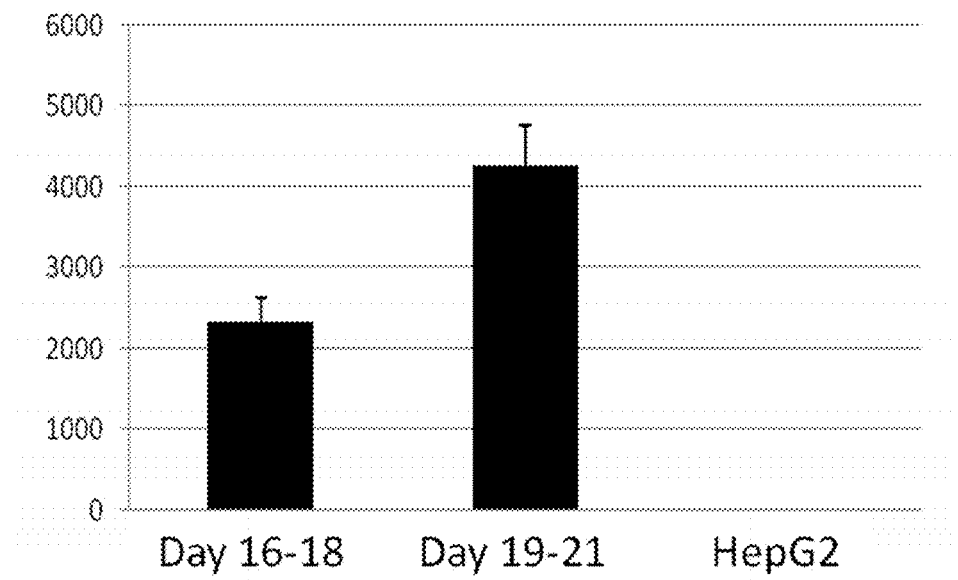
Figure 7B:
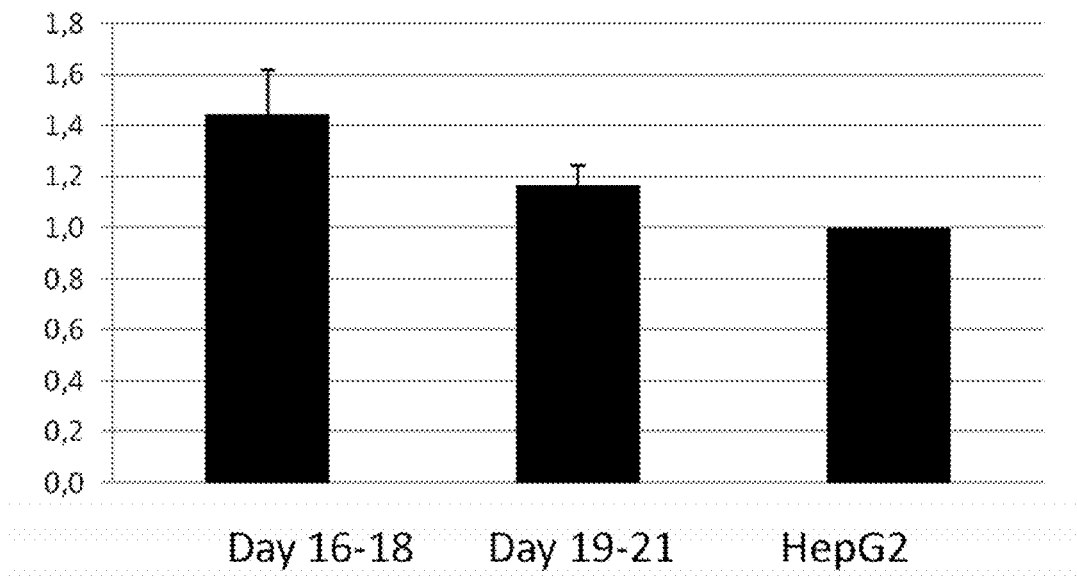
Figure 7C:
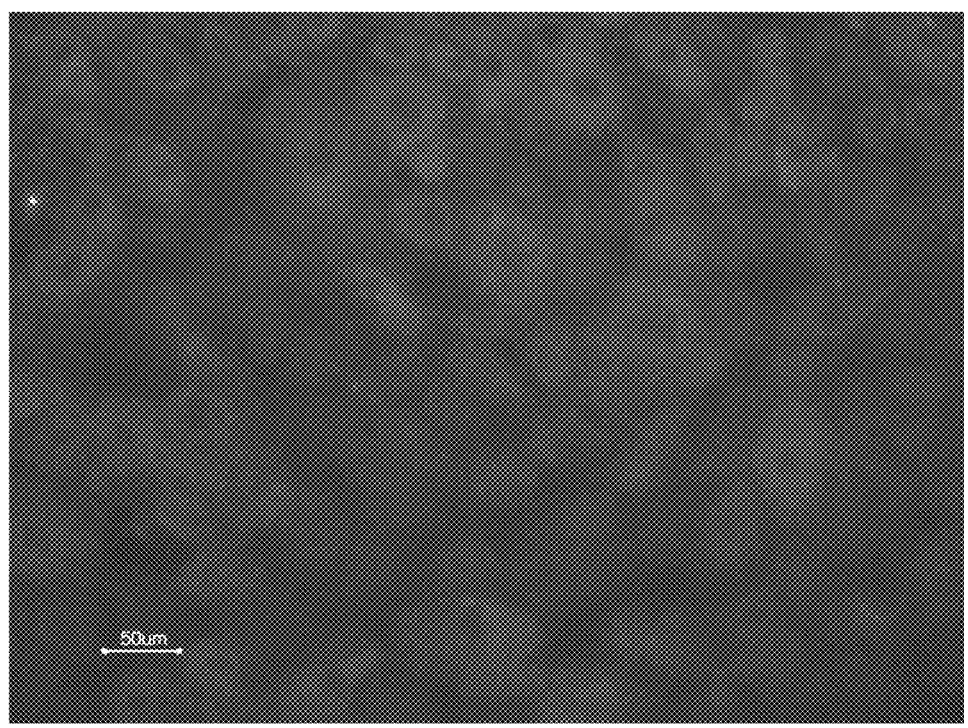

Results hESC-HEP, matured in maturation medium I supplemented with 1.5 µM BIO (MMI+BIO) according to Example 8, were able to metabolize phenacetine into paracetamol to a greater extent than the control cultures according to example 4, see FIG. 7A. On top of that, hES-HEP cultured in maturation medium II supplemented with 1.5 µM BIO (MMII+BIO) (example 9) performed even better than MMI+BIO cultures regarding Cyp 1A activity. This trend was demonstrated for all time points analysed, day 16-18, 20-21 and day 25. The Cyp1A activity increased during time in the two groups treated with BIO, suggesting maturation of hepatocyte-like cells over time in the presence of a GSK3 inhibitor. The Cyp 1A activity was supported by the finding of CYP1A2 and 1A1 gene expression levels similar to or greater than HepG2, see FIG. 7B. In addition, the protein CYP1A2 was detected in hESC-HEP cultures matured in the presence of BIO, see FIG. 7C. To summarise GSK3 inhibitors stimulate CYP1A-family members to be functionally expressed at both mRNA and protein levels in hESC-HEP. As CYP1A1 is expressed in the neonatal liver and CYP1A2 in the newborn and adult liver, the results point at GSK3 inhibitors to take an important part in differentiation and maturation of hESC into hepatocyte-like cells.

Example 16 hPS Cells From Feeder Free Cultures hESCs cultured under feeder free conditions were incubated in media supplemented with Activin A. The cells were then induced into hepatocytes by differentiating them to hepatic progenitor cells and then to more mature hepatocyte like cells. Cells cultured with and without the GSK3 inhibitor were compared for their hepatic profile and homogeneity. For culture details see FIG. 3 and examples 12, 13 and 14.

From this study we could conclude that a GSK3 inhibitor (BIO) was significantly important for the differentiation, maturation, and homogeneity of the cultures. (See results in FIGS. 4A & B), since both metabolic activity (FIG. 4A) and hepatic gene marker expression (FIG. 4B) was higher in cells exposed to GSK-3 inhibitors and thus comparable with hESC-HEPs derived from hPS initially maintained on feeder cells. Confirmation that BIO treatment is affecting the Wnt pathway shown in FIG. 4C where beta-catenin is seen to translocate from cell membrane to nucleus upon treatment with BIO, consistent with its signalling role in the Wnt pathway.

Example 17

Derivation of Hepatocyte Like Cells from hiPS Cells

The culturing and derivation was performed as described in example 12-14 and outlined in FIG. 3, but with hiPS cells replacing the feeder free hPS cells.

The undifferentiated hiPS cells were cultured in Activin A supplemented media to stimulate initial differentiation into partly differentiated cells. The hiPS derived partly differentiated cells were then passaged (to plates coated with 0.1% Gelatin or Matrigel 0.016 mM) and induced to hepatic progenitor cells and then to hepatocyte like cells in media with and without BIO supplementation, see FIG. 3 A)-B).

The conclusion from this study was that the hiPS cells cultured in media supplemented with BIO responded significantly and became more mature compared to the cells that were grown in the absence of the GSK-3 inhibitor. This was concluded by analysing the expression profile of the cells by Q-PCR, immunocytochemistry and Activity Assay (FIG. 5). These results verify and are unanimous with what we have observed for both hES cultured on mEF and hES cultured in a feeder free way (FIG. 4)

The hiPS cells were cultured on mEFs until they were confluent. The cells were washed twice in PBS+/+ and treated with Activin A containing medium (See FIG. 3a-b). The cells adapted an endoderm like morphology around day 3. When the majority of the cells were partly differentiated, the cells were exposed to media supplemented with factors inducing the cells into hepatocyte-like cells (See FIG. 3A)-B)) plus or minus BIO. Different matrix: Gelatin and Matrigel did not significantly affect the outcome. BIO affected the cells significantly in that they upregulated several markers for mature hepatocytes including CYPs (CYP1A2) (see FIG. 5). hESC-HEPs treated with BIO also showed greater metabolic activity (FIG. 5A).

Results

Conclusions of BIO in the Maturation Phase of the Hepatocyte-Like Cell Protocol:

Increased CYP1A activity compared to controls without BIO.

Increased mRNA of CYP1A1, CYP1A2, CYP3A4, CYP2C9, CYP7A1, MRP2, CD44, AFP, CK18, CK19 activity compared to controls without BIO.

Conclusions of the use of a split medium (SM) and BIO in maturation phase of the hepatocyte-like cell protocol as of FIG. 3c). Illustrations of the results are shown in FIG. 5

Increased CYP1A and CYP3A activity compared to controls without BIO.

Increased mRNA of CD44, AFP, CK18, CK19, CYP1A1, CYP1A2, CYP3A4, CYP2C9, CYP7A1, Albumin, OATP2, A1AT, MRP2 activity compared to controls without BIO.

Example 18

Selective Differentiation Using a GSK3 Inhibitor (BIO) Results in a Homogenous Population of Hepatocytes Derived from hES Cells.

Figure 8A:
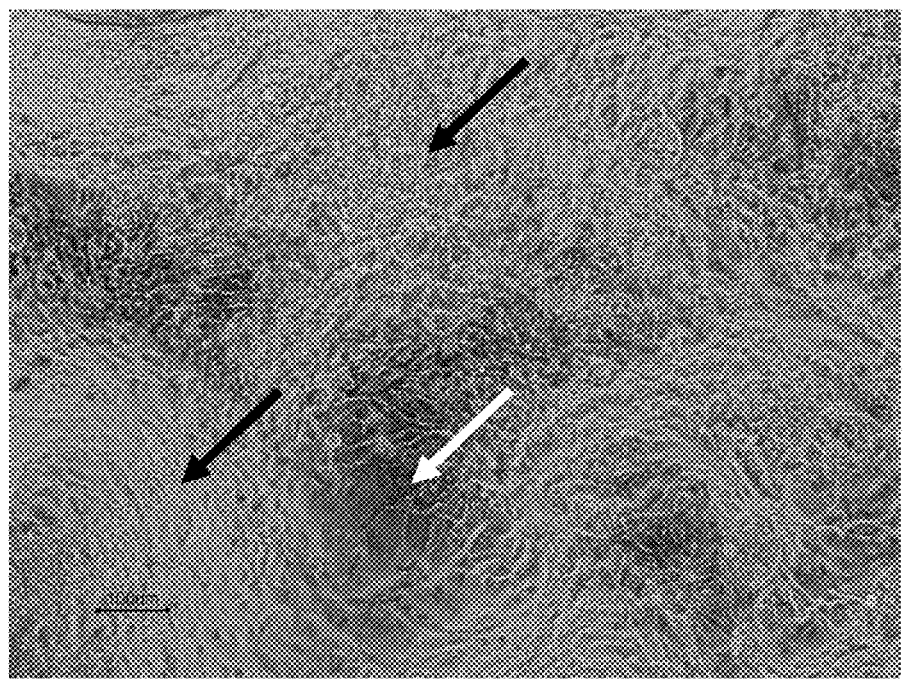
Figure 8B:
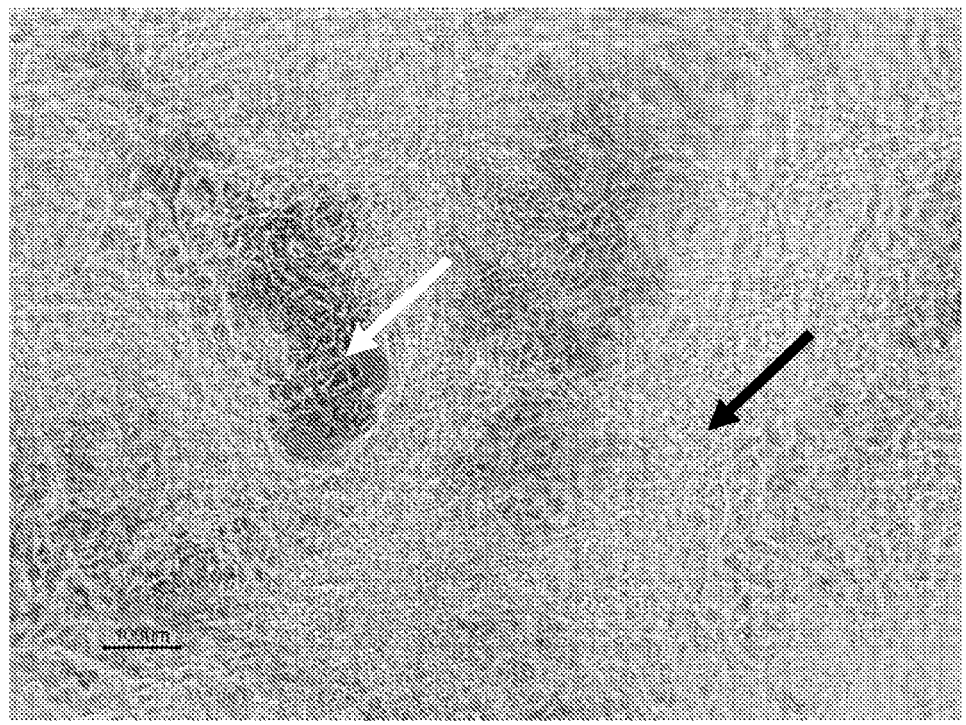
Figure 8C:
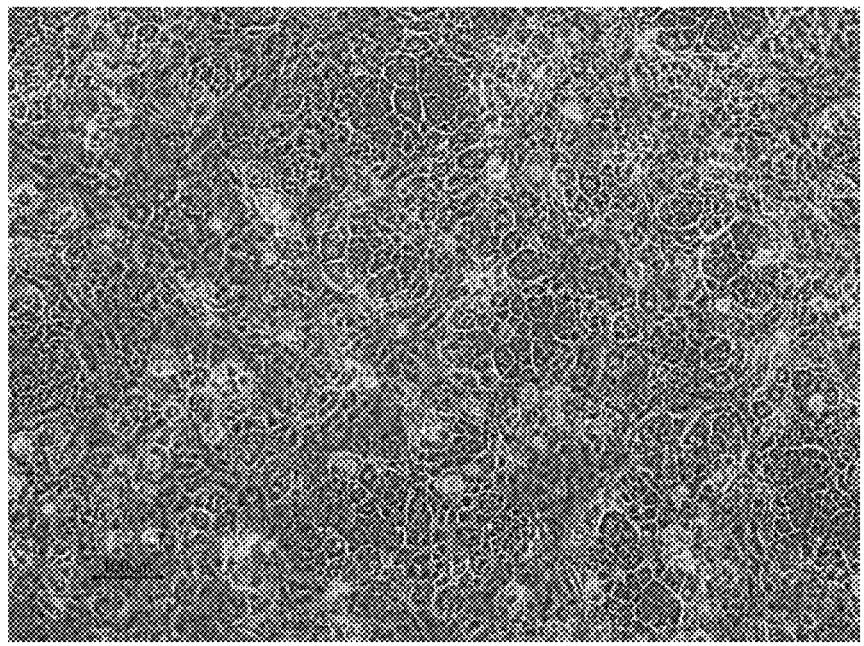
Figure 8D:
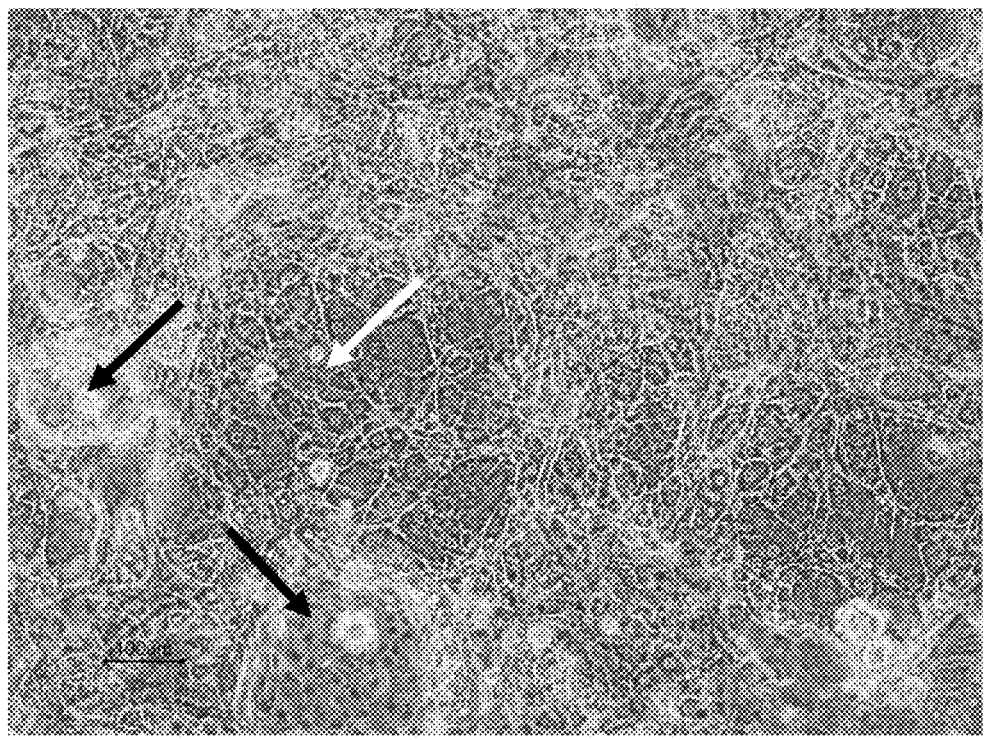
Figure 8E:
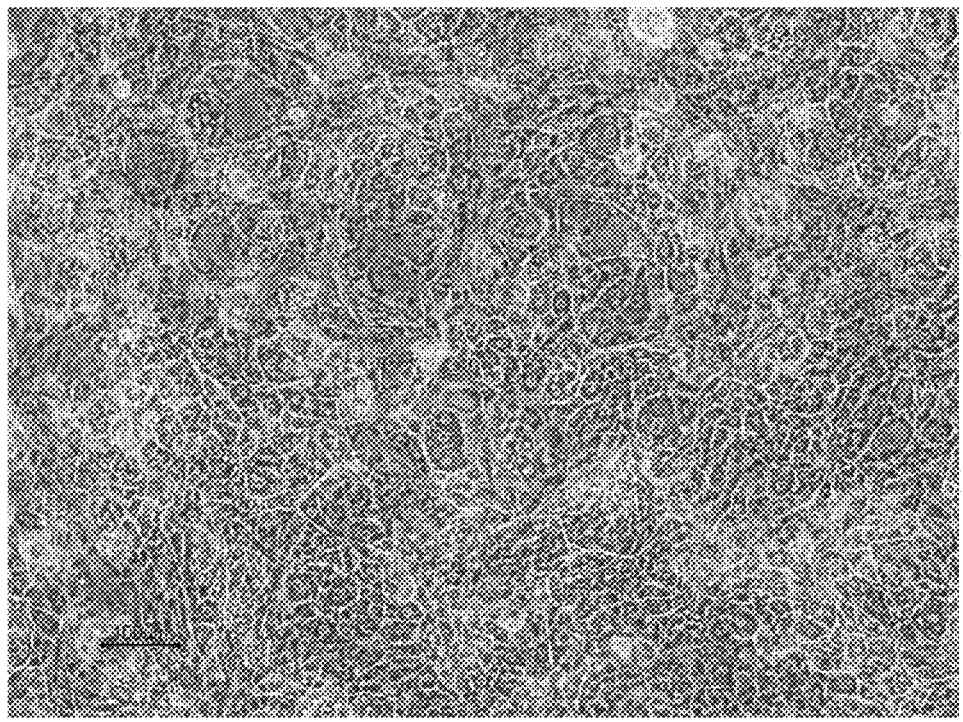

MEF cultured hESC differentiated into hepatocyte-like cells according to example 6 and 11 as outlined in FIG. 2 *ii* and *iv* (presence of BIO from day 3) was compared to hepatocyte-like cells differentiated by example 4 and 8D as outlined in FIG. 2 *i* and *iii* (absence of BIO and with BIO added from day 10-30, respectively) demonstrated purification of hepatocyte-like cells in the cultures treated with BIO from day 3 (example 6 and 11). Morphological observations are illustrated in FIG. 8. Cultures with no or low concentrations (1 µM) of BIO resulted in highly heterogeneous cultures where hardly any hepatocyte-like cells were observed as shown in FIGS. 8A and B. Addition of 5 µM of BIO day 3 resulted in a dramatic cell death to begin with. However, the surviving cells, DE-cells and/or anterior endodermal cells, day 4 were passaged into new wells and a highly purified and homogenous culture of hESC-HEP was appearing as the differentiation process proceeded, see FIG. 8C. An intermediate concentration of BIO (3.5 µM) was tested in cultures from day 3 (Example 11) resulting in more purified hESC-HEP compared to untreated cultures (Example 9), FIGS. 8D and E respectively. In addition, a less dramatic cell death was observed compare to cultures grown in 5 µM BIO from day 3. Thus it appears advantageous to add GSK-3 inhibitors at a later stage of differentiation to avoid massive cell death seen when it is added at day 3. Moreover the resulting purity of the cell populations (FIG. 8, purity table) also suggest that, at least for BIO, addition at a later stage (day 10+) gives greater final purity. Data suggest a role for GSK3 inhibitors in selection of DE-cells and/or anterior endodermal cells, a prerequisite for further differentiation into hepatoblasts and subsequently hepatocyte-like cells. In addition, GSK3 inhibitors at this stage may contribute/stimulate to hepatic induction of the competent endoderm.

Example 19

HDAC Inhibitors Potentiates Wnt-Signalling to Induce and Stimulate Hepatocyte Differentiation FIG. 9 shows data of functional CYP1A activity in hESC-HEP cultures (hepatocyte-like cells) differentiated in a maturation media, such as MMI, supplemented with an HDAC inhibitor, such as Sodium Butyrate (NaB, 1 mM) together with a GSK3 inhibitor, such as BIO (1.4 µM) at day 21-25, following the protocol as described in example 14. Cell line SA002 from mEF cultures was used as starting material.

Those hESC-HEP cultures were compared to parallel hESC-HEP cultures without NaB in the maturation media resulting in increased CYP1A activity in NaB containing cultures. Data suggests a role for HDAC inhibitors, e.g. NaB, to potentiate Wnt-signalling mediated transcription and effect on hepatocyte differentiation.

Example 20

Exposure of GSK3 Inhibitor at Early Hepatic Differentiation Improves Hepatic Gene Expression Profile of hESC-HEP.

hESC-HEP were derived from cell-line SA002 cultures on mEF-layer according to Example 9, FIG. 2, protocol iii (absence of BIO between day 3-10) or Example 11, FIG. 2, protocol iv (presence of 3.5 µM BIO between day 3-10). Total RNA was collected and isolated from the two hES-HEP cultures at day 21, 24, 26 and 28 by using RNA isolation kit from Qiagene. Quantitative reverse transcriptase PCR, QrtPCR, by using Taqman probes, was performed for the following hepatic marker genes: phase I drug metabolizing enzymes; CYP (cytochrome P450) 3A4, 3A5, 3A7, 2C9, phase II drug metabolizing enzymes GSTA1 (glutation-S-transferas A1), UGT2B7 (UDP glucuronosyltransferase 2B7), phase III, transporters; MRP2 (multi-drug residence protein 2), BSEP (bile salt export pump), and general hepatic markers; A1AT (alpha-1 antitrypsin), ALB (albumin) and TAT (tyrosine-amino transferas). All data was normalised to the housekeeping gene CREB. RNA from HepG2 cultures was included and data is presented as fold change of HepG2. BSEP is an exception as HepG2 cells do not express the gene. Thus, BSEP expression is instead presented as fold change of a so called calibrator which contains RNA from different sources.

Data is presented in FIGS. 10A to D and shows that all genes except for CYP3A7 are expressed at higher levels in hESC-HEP exposed to BIO from day 3 than in cultures where BIO was excluded from day 3-10. For CYP3A7 the opposite was observed. As CYP3A7 is a drug metabolizing enzyme which is mainly expressed prenatal and CYP3A4 in the newborn and adult liver, (Cyp 3A5 both pre and post natal and adult) the expression pattern of the CYP3A—family members suggests a role for BIO early in the differentiation protocol to improve hepatic differentiation and contribute to a more maturation hESC-HEP culture by stimulating Wnt signalling. The improved expression levels of the hepatic markers in BIO exposed cultures are supporting the finding that GSK-3 inhibitors are important in early hepatic differentiation of hESC.

Example 21

Improvement of UGT Metabolic Activity in hESC-HEPs Exposed to GSK-3 Inhibition During Early Hepatic Differentiation Metabolic activity of hESC-HEP derived from hESCs cultured in feeder-free conditions (see Examples 12-14) was measured to determine the effect of GSK-3 inhibition during development and maturation by examining the activity of several UDP-glucuronyltransferases (UGTs) (enzymes that participate in the metabolism of many drugs). Activity of these UGTs was tested via several substrates, namely: β-estradiol (UGT1A1, 3-glucuronide), 1-naphthol (UGT1A6), propofol (UGT1A9), and naloxone (UGT2B7). A non-sepcific control (Methylumbelliferone) was also included (see FIG. 12). hESC-HEPs were differentiated essentially according to Example 12, up to day 7. At this point, cells were treated to one of three protocols, either Protocol 1 (day 7-14 VH1 medium, day 14-25 Maturation medium BM2, BIO present only at days 14-25), Protocol 2 (day 7-25 Medium BM2, BIO present only at days 14-25) or Protocol 3 (day 7-14 Medium MMI, day 14-25 Maturation Medium MMII, BIO present days 14-25) with either +/−GSK-3 inhibitor (in this case BIO) at a concentration of 1.4 µM. A clear trend can be seen here, with most of the UGTs having greater activity in cells treated with GSK-3 inhibitor during development, and this trend is seen across all three differentiation protocols. For some UGTs (such as UGT1A1) the increase is much greater than for others, but the overall trend is that exposure of cells to GSK-3 inhibition leads to a more mature, metabolically active phenotype for all of the preferred differentiation methods.

Example 22

Induction of Early and Late Stage Hepatic Markers in hESC-HEPs by Modulation of Wnt-Signalling Using non-BIO GSK-3 Inhibitors at Later Stage Differentiation hESC-HEPs were derived essentially as described in Example 9, FIG. 2*iii*, but with alternative (non_BIO) GSK-3 inhibitors used to show that other GSK-3 inhibitors can be used interchangeably with BIO and can modulate the Wnt-signalling pathway during endoderm to hepatocyte differentiation to induce expression of hepatic marker genes. Furthermore, differentiating cells were exposed to GSK-3 inhibitors only during later (from day 10) stages of differentiation. Three alternative GSK-3 inhibitors were tested alongside BIO to determine effectiveness in inducing hepatic marker expression (SB216763, Kenpaullone and Indirubin-3-O) and results were compiled both for Phase I and Phase II enzymes and hepatic markers, with two negative controls (hESC-HEP not exposed to GSK-3 inhibition during differentiation, and undifferentiated hESC cells). Results are shown in FIG. 12A (Phase I enzyme markers) and FIG. 12B (Phase II enzymes and hepatic markers), and it can be seen that for Phase I enzymes, all GSK-3 substitutes in general seem to induce gene expression above the levels of the negative controls. Indeed, for most of the Phase I enzymes and hepatic markers, Kenpaullone seems to induce higher levels of expression than BIO. Results for Phase II enzymes and hepatic markers are somewhat more variable when different markers and different GSK-3 inhibitors are compared, but again in general it appears that the three alternative compounds tested can be used as feasible substitutes for BIO in modulating the Wnt-signalling pathway and producing mature hepatocyte-like cells. Expression of the housekeeping gene Creb shows little variation across the various samples and protocols. Equivalent results where hiPS cells were used instead of hESC-HEPS are shown in FIG. 14, and again support the finding that BIO can be substituted by other GSK-3 inhibitors.

Example 23

Induction of Early and Late Stage Hepatic Markers in hESC-HEPs by Moudulation of Wnt-Signalling Using Non-810 GSK-3 Inhibitors at Both Mid and Later Stage Differentiation hESC-HEPs were derived essentially as described in Example 11 and FIG. 2iv, but with alternative (non_BIO) GSK-3 inhibitors used to show that other GSK-3 inhibitors can be used interchangeably with BIO and can modulate the Wnt-signalling pathway during endoderm to hepatocyte differentiation to induce expression of hepatic marker genes. Differentiating cells were exposed to GSK-3 inhibitors during both mid (days 3-9) and late (from day 10-23) stages of differentiation. Three alternative GSK-3 inhibitors were tested alongside BIO to determine effectiveness in inducing hepatic marker expression (SB216763, Kenpaullone and Indirubin-3-O) and results were compiled both for Phase I enzymes and Phase II enzymes and hepatic markers, with two negative controls (hESC-HEP not exposed to GSK-3 inhibition during differentiation, and undifferentiated hESC cells). During days 3-9 of differentiation, concentrations of GSK-3 inhibitors used were as follows: BIO 3.5 µM, SB216763 34 nM, Kenpaullone 0.23 µM and Indirubin-3-O 22 nM. For later stage differentiation (days 10-23) concentrations were changed to: BIO 1.5 µM, SB216763 2.5 µM, Kenpaullone 2.5 µM and Indirubin-3-O 2.5 µM Results are shown in FIG. 13A (Phase I enzymes) and FIG. 13B (Phase II enzymes), and it can be seen that for Phase I enzymes, GSK-3 substitutes can in general seem to induce hepatic marker gene expression above the levels of the negative controls and often above the level of that seen in BIO treatment. Indeed, for most of the Phase I enzymes, Kenpaullone seems to induce higher levels of expression than BIO. Results for Phase II enzymes and hepatic markers are somewhat more variable when different markers and different GSK-3 inhibitors are compared, but again in general it appears that the three alternative compounds tested can be used as feasible substitutes for BIO in modulating the Wnt-signalling pathway and producing mature hepatocyte-like cells. It is also apparent that modulation of Wnt-singnalling at mid and late stages by GSK-3 inhibition is comparable to modulation during only late stage. Depending upon the result desired (expression of certain markers over others) then one method may be preferable over the other. Expression levels of the housekeeping gene Creb shows little variation across the various samples and protocols here. Equivalent results where hiPS cells were used instead of hESC-HEPS are shown in FIG. 15, and again support the finding that BIO can be substituted by other GSK-3 inhibitors.

The invention claimed is:

1. A method for directing the differentiation of human definitive endoderm cells into human hepatocyte-like cells, wherein said method comprises:
   i) differentiating human definitive endoderm cells into human hepatoblasts using a differentiation medium containing 0.05-5% DMSO; and
   ii) differentiating said human hepatoblasts obtained in step i) into human hepatocyte-like cells using a differentiation medium containing 0.01-5 µM Dexamethasone, 1-50 ng/ml hepatocyte growth factor (HGF), 1-25 ng/ml Oncostatin M (OsM), 0.05-5% DMSO, and 0.1-10 µM of
   a GSK-3 inhibitor selected from a group consisting of:
   BIO (2'Z,3'£)-6-Bromoindirubin-3'-oxime (GSK3 Inhibitor IX);
   BIO-Acetoxime (2'Z,3'E)-6-Bromoindirubin-3'-acetoxime (GSK3 Inhibitor X);
   (5-Methyl-1H-pyrazol-3-yl)-(2-phenylquinazolin-4-yl) amine (GSK3-Inhibitor XIII);
   Pyridocarbazole-cyclopenadienylruthenium complex (GSK3 Inhibitor XV);
   TDZD-8 4-Benzyl-2-methyl-1,2,4-thiadiazolidine-3,5-dione (GSK3beta Inhibitor I);
   2-Thio(3-iodobenzyl)-5-(1-pyridyl)-[1,3,4]-oxadiazole (GSK3beta Inhibitor II);
   OTDZT 2,4-Dibenzyl-5-oxothiadiazolidine-3-thione (GSK3beta Inhibitor III);
   alpha-4-Dibromoacetophenone (GSK3beta Inhibitor VII);
   AR-AO 14418 N-(4-Methoxybenzyl)-N'-(5-nitro-1,3-thiazol-2-yl)urea (GSK-3beta Inhibitor VIII);
   3-(1-(3-Hydroxypropyl)-1H-pyrrolo[2,3-b]pyridin-3-yl]-4-pyrazin-2-yl-pyrrole-2,5-dione (GSK-3beta Inhibitor XI);
   TWSI 19 pyrrolopyrimidine compound (GSK3beta Inhibitor XII);
   L803 H-KEAPPAPPQSpP-NH2 (SEQ ID NO:1) or its Myristoylated form (GSK3beta Inhibitor XIII);
   2-Chloro-1-(4,5-dibromo-thiophen-2-yl)-ethanone (GSK3beta Inhibitor VI); Aminopyrimidine CHIR99021;
   Kenpaullone (9-Bromo-7,12-dihydro-indolo[3,2-d][1]benzazepin-6(5H)-one;
   SB216763 3-(2,4-Dichlorophenyl)-4-(1-methyl-1H-indol-3-yl)-1H-pyrrole-2,5-dione; and
   Indirubin-3'-monoxime.

2. The method according to claim 1, wherein the differentiation of human definitive endodermal cells into human hepatocyte-like cells is carried out under xeno-free conditions using xeno-free endodermal cells.

3. The method according to claim 1, wherein the differentiation medium used in step ii) is supplemented with a histone deacetylase (HDAC)-inhibitor in addition to said GSK-3 inhibitor.

4. The method according to claim 3, wherein the HDAC-inhibitor is Sodium Butyrate (NaB).

5. The method according to claim 3, wherein the HDAC-inhibitor is Sodium Butyrate (NaB) and the concentration of NaB in the differentiation medium used in step ii) is from 0.1 mM to 10 mM.

6. The method according to claim 3, wherein the HDAC-inhibitor is Sodium Butyrate (NaB) and the concentration of NaB in the differentiation medium used in step ii) is 0.05 mM to 5 mM.

7. The method according to claim 3, wherein the HDAC-inhibitor is Sodium Butyrate (NaB) and the concentration of NaB in the differentiation medium used in step ii) is 1 mM.

8. The method according to claim 1, wherein the concentration of the GSK-3 inhibitor in the differentiation medium used in step ii) is from 1 µM to 5 µM.

9. The method according to claim 1, wherein the GSK-3 inhibitor is BIO (2'Z,3'£)-6-Bromoindirubin-3'-oxime (GSK3 Inhibitor IX).

10. The method according to claim 1, wherein the GSK-3 inhibitor is Kenpaullone (9-Bromo-7,12-dihydro-indolo[3,2-d][1]benzazepin-6(5H)-one.

11. The method according to claim 1, wherein the GSK-3 inhibitor is SB216763 3-(2,4-Dichlorophenyl)-4-(1-methyl-1H-indol-3-yl)-1H-pyrrole-2,5-dione.

12. The method according to claim 1, wherein the GSK-3 inhibitor is Indirubin-3'-monoxime.

* * * * *

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial
<220> FEATURE:
<223> OTHER INFORMATION: Synthetically generated peptide
<220> FEATURE:
<221> NAME/KEY: MOD_RES
<222> LOCATION: (10)..(10)
<223> OTHER INFORMATION: PHOSPHORYLATION
<220> FEATURE:
<221> NAME/KEY: MOD_RES
<222> LOCATION: (11)..(11)
<223> OTHER INFORMATION: AMIDATION

<400> SEQUENCE: 1

Lys Glu Ala Pro Pro Ala Pro Pro Gln Ser Pro
1               5                   10
```